United States Patent [19]
Abreo et al.

[11] Patent Number: 5,948,793
[45] Date of Patent: Sep. 7, 1999

[54] 3-PYRIDYLOXYMETHYL HETEROCYCLIC ETHER COMPOUNDS USEFUL IN CONTROLLING NEUROTRANSMITTER RELEASE

[75] Inventors: Melwyn A. Abreo, Imperial Beach, Calif.; David E. Gunn, Waukegan; Nan-Horng Lin, Mundelein, both of Ill.; David S. Garvey, Waltham, Mass.; Mark W. Holladay, Libertyville; Keith B. Ryther, Round Lake Park, both of Ill.

[73] Assignee: Abbott Laboratories, Abbott Park, Ill.

[21] Appl. No.: 08/474,873

[22] Filed: Jun. 7, 1995

Related U.S. Application Data

[63] Continuation-in-part of application No. 08/391,749, Feb. 21, 1995, abandoned, which is a continuation of application No. 08/129,222, Oct. 4, 1993, abandoned, which is a continuation-in-part of application No. 08/126,481, Sep. 28, 1993, abandoned, which is a continuation-in-part of application No. 07/959,005, Oct. 9, 1992, abandoned.

[51] Int. Cl.⁶ .................. C07D 401/12; A61K 31/55
[52] U.S. Cl. .................. 514/318; 514/340; 514/343; 546/193; 546/268.1; 546/276.4
[58] Field of Search ............. 546/193, 268.1, 546/276.4; 514/318, 340, 343

[56] References Cited

U.S. PATENT DOCUMENTS

| | | | |
|---|---|---|---|
| 4,592,866 | 6/1986 | Cale, Jr. ................. | 260/239.3 |
| 4,643,995 | 2/1987 | Engel et al. ............. | 514/210 |
| 4,705,853 | 11/1987 | Cale ...................... | 540/490 |
| 4,929,625 | 5/1990 | Cliffe et al. ............ | 514/304 |
| 4,946,836 | 8/1990 | Engel et al. ............ | 514/183 |
| 4,956,359 | 9/1990 | Taylor, Jr. et al. ..... | 514/210 |
| 5,037,841 | 8/1991 | Schoehe et al. ........ | 544/315 |
| 5,169,855 | 12/1992 | Cain et al. ............. | 514/319 |

FOREIGN PATENT DOCUMENTS

| | | | |
|---|---|---|---|
| 296560A2 | 12/1988 | European Pat. Off. ...... | C07D 211/26 |
| 9408992 | 8/1993 | WIPO ..................... | C07D 401/12 |
| 9408992 | 4/1994 | WIPO . | |

OTHER PUBLICATIONS

K. Tomioka et al., Stereoselective Reactions XIX. Asymmetric Dihydroxylation of Olefins by Employing Osmium Tetroxide–Chiral Amine Complexes, *Chem. Pharm. Bull.*, 1990, 38:2133–5.

Sullivan, et al. (±)–Epibatidine Elicits a Diversity of In Vitro and In Vivo Effects Mediated by Nicotinic Acetylcholine Receptors,Journ of Pharm and Experimental Therapeutics vol. 271 No. 2 624–631.

Badio, et al., Antinociceptice Effects of the Aklaloid Epibatidine: Further Studies on Involvement of Nicotine Receptors, Drug Development Research 36:46–59 (1995).

Sullivan, et al., Epibatidine: Pharmacological Properties of a Novel Nicotinic Acetylcholine Receptor Agoists and Analgesic Agent, CNS Drug Reviews vol. 2. No. 1 pp. 21–39.

Burger, Medicinal Chemistry, Third Edition Part I.

Sullivan. The Organic Chemistry of Drug Design and Drug Action; pp. 19–21.

*Primary Examiner*—Richard L. Raymond
*Assistant Examiner*—Deepak R. Rao
*Attorney, Agent, or Firm*—Jerry F. Janssen; Monte R. Browder; Michael J. Ward

[57] ABSTRACT

Novel heterocyclic ether compounds of the formula:

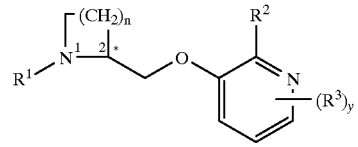

wherein n, *, $R^1$, $R^2$, $R^3$ and y are specifically defined, or pharmaceutically acceptable salts or prodrugs thereof, which are useful in selectively controlling neurotransmitter release; therapeutically-effective pharmaceutical compositions of these compounds; and use of said compositions to selectively control neurotransmitter release in mammals.

8 Claims, No Drawings

3-PYRIDYLOXYMETHYL HETEROCYCLIC ETHER COMPOUNDS USEFUL IN CONTROLLING NEUROTRANSMITTER RELEASE

CROSS-REFERENCE TO RELATED APPLICATIONS

This application is a continuation-in-part application of application Ser. No. 08/391,749, filed Feb. 21, 1995, now abandoned, which was a continuation application of application Ser. No. 08/129,223, filed Oct. 4, 1993, now abandoned, which was a continuation-in-part of application Ser. No. 08/126,481, filed Sep. 28, 1993, now abandoned, which was a continuation-in-part application of Ser. No. 07/959,005, filed Oct. 9, 1992, now abandoned.

TECHNICAL FIELD

This invention relates to 3-pyridyloxymethyl heterocyclic ether compounds which control neurotransmitter release; to pharmaceutical compositions containing these compounds; and to the use of the compositions to control neurotransmitter release in mammals.

BACKGROUND OF THE INVENTION

Dopamine is widely recognized as an important neurotransmitter in the central nervous systems in humans and animals, and itself possesses intrinsic pharmalogical properties. Many aspects of the pharmacology of dopamine have been reviewed by Roth and Elsworth (Biochemical Pharmacology of Midbrain Dopamine Neurons. In: *Psychopharmacology: The fourth generation of progress*, F. E. Bloom and D. J. Kupfer, Eds., Raven Press, N.Y., 1995, pp 227–243). One group of compound studied extensively is that of pharmacologic agents that modify dopamine release or the release of other neurotransmitters.

Control of dopamine or neurotransmitter release is an important utility in-and-of itself. Studies of dopamine and neurotransmitter release have led to the discovery of important pharmacologically active compounds. However, new and selective neurotransmitter controlling agents are still being sought, in the hope that one or more will be useful in as yet poorly controlled disease states or behavior models.

For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention-Deficit Disorder (ADD). Specific agents for treatment of these and related disorders are few in number or non-existent. behavioral disorder Attention-Deficit Disorder (ADD). Specific agents for treatment of these and related disorders are few in number or non-existent.

One means of studying neurotransmitter release is to study the activation of cholinergic channel mediated release (Wonanacott et al., Presynaptic nicotinic autoreceptors and heteroreceptors in the CNS. In: *Effects of Nicotine on Biological Systems II: Advances in Pharmacological Sciences*. P. B. S. Clark et al, Eds., Birkhauser, Basel, 1995, pp. 87–94). The biological effects of acetylcholine, for example, are mediated by distinct specific interactions with different subtypes of cholinergic receptors. The two distinct subfamilies of cholinergic receptors are defined as nicotinic cholinergic receptors and muscarinic cholinergic receptors. (See Taylor, Goodman and Gilman's The Pharmacological Basis of Therapeutics, 8th ed.) The responses of these receptor families are mediated by two entirely different classes of second messenger systems. Nicotinic receptor activation mediates the conductance of specific extracellular ions (e.g. $Na^+$, $K^+$ and $Ca^{++}$) through the neuronal membrane, whereas muscarinic receptors are coupled to intracellular systems that contain complex molecules such as G-proteins and inositol phosphates. Thus, the biological consequences of nicotinic cholinergic channel activation by acetylcholine are distinct from those of muscarinic activation. In an analogous manner, inhibition of nicotinic cholinergic channels result in still other effects distinct and different from those arising from muscarinic receptor inhibition.

In fact, there is reason to expect or suggest that agents that control neurotransmitter release and which bind at the nicotinic cholinergic receptors may show activity in addressing some untreatable disorders of the central nervous system, including those mentioned above. Partial evidence in support of this suggestion is set forth briefly below.

The precise molecular lesions that contribute to the morphological and functional deficits associated with dementia are not fully understood, despite intensive research efforts. However, the most consistent abnormality for Alzheimer's disease, as well as for vascular dementia and cognitive impairment due to organic brain disease related to alcoholism, is the degeneration of the cholinergic system arising from the basal forebrain (BF) to both the cortex and hippocampus (Bigl et al., in *Brain Cholinergic Systems*, M. Steriade and D. Biesold, eds., Oxford University Press, Oxford, 1990, pp. 364–386). In particular, neurochemical evidence from the brains of patients afflicted with Alzheimer's disease has revealed reliable decreases in markers of cholinergic neuronal function (Perry et al., *Br. Med. J.*, 2:1457, 1978; Reisine et al., *Brain Res.*, 159:477, 1978; Coyle et al., *Science*, 219:1184, 1983; and McGeer et al., *Neurology*, 34:741, 1984). While there are a number of other neurotransmitter systems affected by Alzheimer's disease (Davies, *Med. Res. Rev.*, 3:221, 1983), the relative occurrence of such abnormalities is less consistent or the effect is less profound than the decreases in these cholinergic neuronal function markers. More specifically, substantial reductions (30–50%) in nicotinic cholinergic channel receptors have been consistently reported in the brains of patients with Alzheimer's disease or Parkinson's disease (Kellar et al., *Brain Res.*, 436:62, 1987; and Whitehouse et al., *Neurol.*, 38:720, 1988), whereas changes in muscarinic cholinergic receptors are less remarkable and more dependent or receptor subtype.

However, degeneration of the cholinergic neurotransmitter system has also been reported in aged, but otherwise healthy, individuals (for a review, see Giacobini, *J. Neurosci. Res.*, 27:548, 1990). Moreover, aging may cause a decrease in the cholinergic impulses flow from the basal forebrain to the cortex (Aston-Jones et al., *Brain Res.*, 325:271, 1985). Consistent with these findings are pharmacological studies suggesting that cholinergic mechanisms are, at least in part, responsible for the memory disturbances in aged animals and humans not suffering from Alzheimer's disease (Drachman and Leavitt, *Arch. Neurol.*, 30:113, 1974; Bartus et al., *Science*, 217:408, 1982).

Other clinical signs associated with the neurodegenerative process of Alzheimer's disease include decreases in regional cerebral blood flow and cerebral glucose utilization, in regions which largely parallel the areas where cholinergic deficits occur (Ingvar and Risberg, *Exp. Brain Res.*, 3:195, 1962; Ingvar et al., *Aging: Alzheimer's Disease, Senile Dementia and Related Disorders*, Vol. 7, R. Katzman, R. D. Terry, and K. L. Bick, eds., Raven Press, 1978, p. 203; and Dastur, *J. Cerebral Blood Flow & Metabol.*, 5:1, 1985). Recent clinical evidence suggests that this abnormality observed in Alzheimer's disease patients reflects regional nicotinic cholinergic deficits (Prohovnik, *Neurobiol. Aging*, 11:262, 1990). In agreement with this finding, is the discovery that regulation of cerebral blood flow in the frontoparietal cortex in the rat, governed by the basal forebrain, is also dependent upon nicotinic mechanisms (Arneric, *J. Cerebral Blood Flow & Metabol.*, 2 (Suppl. 1): S502, 1989).

Pilot clinical studies suggest that nicotine may be useful for the acute treatment of deficits in attention and information processing associated with Alzheimer's disease (Sahakian et al., *Brit. J. Psych.*, 154:797, 1989; Newhouse et al., *Psychopharmacol.*, 95:171, 1988). It has been shown that both acutely- and chronically-administered nicotine enhances cognitive function in rats (Levin et al., *Behav. Neural Biol.*, 53:269, 1990), an effect that is also observed in aged animals (Cregan et al., *Soc. Neurosci. Abstract*, 15: 2952, 1989). Nicotine is expected to be neuroprotective, because it has been shown that nicotine can prevent presynaptic loss of functional dopaminergic neurons in animal studies with induced brain injuries (Janson et al., *Prog. Brain Res.*, 79:257, 1989; and Owman et al., *Prog. Brain Res.*, 79:267, 1989).

Other situations where beneficial therapeutic outcome may be achieved or improved through administrrtion of nicotine or a cholinergic channel activator, because of neurotransmitter releasing and anxiolytic properties of these agents, include attention-deficit disorder and drug withdrawal.

Attention-deficit disorder (ADD), with or without hyperactivity, is a behavioral disorder characterized by distractibility and impulsiveness. Children with this disorder are handicapped by their inability to concentrate and control their impulsivity, especially in settings requiring sustained attention, for example, in school. Neurochemically, ADD is thought to be the result of a decreased release of dopamine (Oades, R. D., *Prog. Neurobiol.*, 29:365–391, 1987; Rogeness et al., *J. Am. Acad. Child Adolescent* Psychiatry, 31:765–781, 1992; Shenker, A., *Adv. Pediatr.*, 39:337–382, 1992). Dopaminergic stimulation has been shown to be important in further regulating the release of acetylcholine from areas of the brain involved with attentional precessing such as the cerebral cortex and hippocampus (Day, J. and Fibiger, H. C., *Synapse*, 12:281–286, 1992). Nicotine, d-amphetamine and methylphenidate each enhance the release of dopamine and acetylcholine (Day, J. and Fibiger, H. C., *Neuroscience*, 54:643–648, 1993), although by different pharmacological mechanisms (Lefkowitz, R. J., Hoffman, B. B., and Taylor, P., Neurohumoral transmission: The autonomic and somatic motor nervous systems. In: *Goodman and Gilman's, The Pharmacological Basis of Therapeutics*, (eds. A. G. Gilman, T. W. Rall, A. S. Nies, P. Taylor) Pergamon Press, New York, 1990, pp. 244–268.). While a cure for this disorder has not been found, stimulants, such as d-amphetamine and methylphenidate which enhance the release of dopamine and acetylcholine, have been used successfully in management of the behavioral manifestations of ADD. Nicotine, because of its ability to improve concentration and task performance (F. T. Etscorn, U.S. Pat. No. 4,597,961, issued Jul. 1, 1986; and D. M. Warburton and K. Wesnes in *Smoking Behavior*, R. E. Thornton, ed., Churchill-Livingston, Edinburgh, 1978, pp. 19–43) is also potentially useful in treating ADD. Pilot clinical studies using transdermal patches containing nicotine recently have been shown to improve the symptoms of ADD (Levine et al., *Soc. for Research on Nicotine and Tobacco*, Mar. 24–25, P63, 1995). Thus, enhancing the release of dopamine and acetylcholine with other compounds that activate nicotinic cholinergic channels may also have clinical utility in treating the symptoms of ADD, especially, if those compounds have a safer side effect profile compared to nicotine.

Schizophrenia is considered to be the result of overactive dopamine release (Kahn, R. S. and David, K L., New Developments in dopamine and schizophrenia In: *Psychopharmacology: The fourth generation of progress*, op. cit). Thus compounds that inhibit dopamine might be useful in the treatment of this condition. Evidence for the potential benefits of nicotinic cholinergic channel receptor-based therapies in schizophrenia come from the observation that certain nicotinic channel ligands have been shown to be neuroprotective (e.g., Freedman et al., In: *Effects of Nicotine on Biological Systems II, Advances in Pharmacological Sciences*, op. cit., pp.307–312; Martin et al., *Drug Dev. Res.*, 31:135–141, 1994; Akaike et al., *Brain Res* 644:181–187, 1994; Marin et al., *Neuroreport*, 5:1977–1980, 1994). Epidemiologic data indicating increased prevalence of smoking among patients with schizophrenia (>80%), may be an attempt to self-medicate both for palliative and neuroprotective benefits. Moreover, given the cognition-enhancing potential of nicotinic channel modulators, and the ability of (−)-nicotine to normalize sensory-gating impairments, it is possible that such compounds may be useful in treating two major dysfunctional manifestations of schizophrenia.

Parkinsonism is a clinical syndrome with four cardinal features: bradykinesia, muscular rigidity, resting tremor, and abnormalities of posture and gait. Classical investigations have clearly established that the basal ganglia and the nigrostriatal dopamine system as the site of the fundamental neurochemical lesion of the disease (Korczyn, A. D., Parkinson's Disease. In: *Psychopharmacology: The Fourth Generation of Progress*, op. cit., pp. 1479–1484.). Clinical studies have demonstrated the efficacy of restoring dopamine release, or mimic dopamine receptor activation. The therapeutic effects of nicotine in Parkinson's disease were described more than half a century ago (Moll, Brit. Med. J. 1: 1079, 1926), and interest has been renewed more recently (Janson et al., In: *Effects of Nicotine on Biological Systems II, Advances in Pharmacological Sciences*, op. cit., pp. 321–328). In addition, nicotine has been employed as a potential drug in the treatment of another movement disorder, Tourette's disease (McConville et al., *Am. J. Psychiatry*, 148:739, 1991; Silver et al, In: *Effects of Nicotine on Biological Systems II, Advances in Pharmacological Sciences*, op. cit., pp. 293–299.). Development of compounds that provide a more selective and persistent depolarization of cholinergic channel receptors in the brain than nicotine may provide a safer and more effective treatment of Parkinson's disease and related movement disorders.

The nicotine withdrawal syndrome associated with smoking cessation is characterized by craving for nicotine, irritability, frustration or anger, anxiety, difficulty concentrating, restlessness, decreased heart rate and increased appetite and weight gain. Nicotine has, not surprisingly, been found to ease the withdrawal experienced by those attempting to break tobacco dependencies. As early as 1942, Johnston reported (L. Johnston, *Lancet*, 2:742, 1942) that injections of nicotine relieved the withdrawal symptoms experienced by cigarette smokers when they stopped smoking. More recently, in double-blind studies, nicotine was far superior to a placebo in suppressing or preventing the appearance of many of the signs and symptoms of withdrawal (J. R. Hughes et al., *Psychopharmacology*, 83:82–7, 1984; N. G. Schneider et al., *Addictive Behavior*, 2:149–56, 1984; R. J. West et al., *Journal of Addiction*, 79:215–9, 1984; K. O. Fagerstrom in *Nicotine Replacement: a Critical Evaluation*, O. F. Pomperleau and C. S. Pomperleau, eds., Alan R. Liss, Inc., New York, 1988, pp. 109–28; and J. E. Henningfield and D. R. Jasinski, ibid, pp.35–61). Irritability and impatience were shown to have been reduced in at least five independent controlled studies, while anxiety and difficulty concentrating were shown to have been reduced in at least two studies. One approach to alleviating the symptoms of tobacco withdrawal has been to develop more efficient methods of delivering nicotine, itself, for example, in transdermal patches (F. T. Etscorn, U.S. Pat. No. 4,597,961, issued Jul. 1, 1986). The major problem with this approach is the non-selective effect of nicotine and in particular, the stimulant effects of increasing cardiac workload and oxygen demand that nicotine has on the heart. A selective cholinergic channel activator would be expected to be equally efficacious in relieving withdrawal symptoms with fewer cardiovascular liabilities.

Existing cholinergic channel agonists are therapeutically sub-optimal in treating the conditions discussed above. For example, such compounds have unfavorable pharmacokinetics (e.g., arecoline and nicotine), poor potency and lack of selectivity (e.g., (–)-nicotine), poor CNS penetration (e.g., carbachol) or poor oral bioavailability (e.g., nicotine). In addition, other agents have many unwanted central agonist actions, including hypothermia, hypolocomotion and tremor and peripheral side effects, including miosis, lachrymation, defecation and tachycardia (Benowitz et al., in: *Nicotine Psychopharmacology*, S. Wonnacott, M. A. H. Russell, & I. P. Stolermnan, eds., Oxford University Press, Oxford, 1990, pp. 112–157; and M. Davidson, et al., in *Current Research in Alzheimer Theropy*, E. Giacobini and R. Becker, ed.; Taylor & Francis: New York, 1988; pp 333–336).

Various heterocyclic 2-pyrrolidinyloxy-substituted compounds with analgesic and hypotensive activities have been disclosed by Scheffler et al. (U.S. Pat. No. 4,643,995) and Tomioka et al. (*Chem. Pharm. Bull*, 38:2133–5, 1990).

Certain other 2-pyridyloxy-substituted compounds are disclosed inter alia by Engel et al. in U.S. Pat. No. 4,946,836 as having analgesic activity.

Various other compounds having a pyrrolidine or azetidine moiety substituted at the 3-position with a heterocycloxy group have also been disclosed (cf. U.S. Pat. Nos. 4,592,866 to A. D. Cale; 4,705,853 to A. D. Cale; 4,956,359 to Taylor et al.; and 5,037,841 to Schoehe et al. and European patent application EP296560A2, to Sugimoto et al.).

SUMMARY OF THE INVENTION

In accordance with the present invention, it has been found that 3-pyridyloxymethyl heterocyclic ether compounds are selective and potent cholinergic compounds useful in controlling neurotransmitter release.

In accordance with the principle aspect of the present invention there are provided 3-pyridyloxymethyl heterocyclic ether compounds of formula (I)

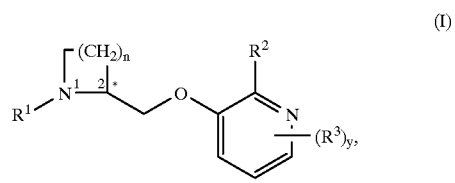

or a pharmaceutically acceptable salt thereof, wherein
the asterisk indicates a chiral center;
n is 1, 2, or 3;
y is 1 or 2;
$R^1$ is H, allyl or $C_1$–$C_6$-alkyl;
$R^2$ is H, F, Cl, or $C_1$–$C_3$-alkyl; and
$R^3$ is independently selected from H, F, Cl, Br or $C_1$–$C_6$-alkyl;
with the provisos that
(a) when $R^2$ is $C_1$–$C_3$-alkyl, then $R^1$ is H, and
(b) when y is 2, then $R^2$ is hydrogen.

Another aspect of the invention comprises therapeutically-effective pharmaceutical compositions containing these compounds.

Still another aspect of this invention comprises the use of said compositions to selectively control neurotransmitter release in mammals.

DETAILED DESCRIPTION OF THE INVENTION

In one embodiment of the instant invention, in the compounds of formula (I) or their pharmaceutically-acceptable salts or prodrugs, the chiral center is of the (S) configuration.

In another embodiment of the instant invention, in the compounds of formula (I) or their pharmaceutically-acceptable salts or prodrugs, the chiral center is of the (R) configuration.

Preferred compounds of the present invention are represented by compounds of formula (I), wherein n is 1 or 2; or a pharmaceutically-acceptable salt or prodrug thereof.

More preferred embodiments of the present invention are represented by compounds of formula (I), wherein:
n is 1;
n is 2 and $R^1$ is H; or
n is 2, $R^1$ is methyl and the compound is of the (S)-configuration;
or a pharmaceutically-acceptable salt or prodrug thereof.
The following novel compounds are representative of the present invention:
3-((1-methyl-2-(R)-pyrrolidinyl)methoxy)pyridine;
3-(2-(R)-pyrrolidinylmethoxy)pyridine;
3-((1-methyl-2-(S)-pyrrolidinyl)methoxy)pyridine;
3-(2-(S)-azetidinylmethoxy)pyridine;
3-((1-methyl-2-(S)-azetidinyl)methoxy)pyridine;
3-(2-(S)-pyrrolidinylmethoxy)pyridine;
5-chloro-3-(2-(S)-pyrrolidinylmethoxy)pyridine;
5-chloro-3-((1-methyl-2-(S)-pyrrolidinyl)methoxy) pyridine;
2-methyl-3-(2-(S)-pyrrolidinylmethoxy)pyridine;
6-methyl-3-(2-(S)-pyrrolidinylmethoxy)pyridine;
6-methyl-3-((1-methyl-2-(S)-pyrrolidinyl)methoxy) pyridine;
4-bromo-3-(2-(S)-pyrrolidinylmethoxy)pyridine;

4-bromo-3-((1-methyl-2-(S)-pyrrolidinyl)methoxy)pyridine;
3-((1-methyl-2-piperidinyl)methoxy)pyridine;
4-methyl-3-(2-(S)-pyrrolidinylmethoxy)pyridine;
5-bromo-3-((1-methyl-2-(S)-pyrrolidinyl)methoxy)pyridine;
2-methyl-3-(2-(S)-azetidinylmethoxy)pyridine;
2-Methyl-3-((1-methyl-2-(S)-azetidinyl)methoxy)pyridine;
5-chloro-3-(2-(R)-pyrrolidinylmethoxy)pyridine;
5-chloro-3-((1-methyl-2-(R)-pyrrolidinyl)methoxy)pyridine;
2-methyl-3-(2-(R)-pyrrolidinylmethoxy)pyridine;
6-methyl-3-((1-methyl-2-(R)-pyrrolidinyl)methoxy)pyridine;
6-methyl-3-(2-(R)-pyrrolidinylmethoxy)pyridine;
3-((1-ethyl-2-(S)-pyrrolidinyl)methoxy)pyridine;
5-chloro-3-(2-(S)-azetidinylmethoxy)pyridine;
6-methyl-3-(2-(S)-azetidinylmethoxy)pyridine;
2-methyl-3-(2-(R)-azetidinylmethoxy)pyridine;
3-((1-methyl-2-(R)-piperidinyl)methoxy)pyridine;
2-chloro-3-(2-(S)-pyrrolidinylmethoxy)pyridine;
3-(2-(S)-pyrrolidinylmethoxy)-6-chloropyridine;
4-methyl-3-((1-methyl-2-(S)-pyrrolidinyl)methoxy)pyridine;
3-((1-methyl-2-(R)-pyrrolidinyl)methoxy)-6-chloropyridine;
3-(2-(S)-azetidinylmethoxy)-6-chloropyridine;
2-methyl-3-(1-methyl-2-(S)-pyrrolidinylmethoxy)pyridine;
6-chloro-3-((1-methyl-2-(S)-pyrrolidinyl)methoxy)pyridine;
5-bromo-3-((1-methyl-2-(R)-pyrrolidinyl)methoxy)pyridine;
3-(2-(R)-pyrrolidinylmethoxy)-6-chloropyridine;
3-((1-methyl-2-(S)-azetidinyl)methoxy)-6-methylpyridine;
3-(2-(R)-azetidinylmethoxy)pyridine;
3-((1-methyl-2-(R)-azetidinyl)methoxy)pyridine;
4-methyl-3-(2-(S)-azetidinylmethoxy)pyridine;
5-bromo-3-(2-(S)-pyrrolidinylmethoxy)pyridine;
3-(2-(S)-azetidinylmethoxy)-5-bromopyridine;
3-((1-methyl-2-(S)-azetidinyl)methoxy)-5-bromopyridine;
5-n-butyl-3-((1-methyl-2-(S)-pyrrolidinyl)methoxy)pyridine;
5-methyl-3-(1-methyl-2-(S)-pyrrolidinylmethoxy)pyridine;
5-ethyl-3-(1-methyl-2-(S)-pyrrolidinylmethoxy)pyridine;
5-n-propyl-3-((1-methyl-2-(S)-pyrrolidinyl)methoxy)pyridine
5-chloro-3-((1-methyl-2-(S)-azetidinyl)methoxy)pyridine;
2-methyl-3-(2-(R)-azetidinylmethoxy)pyridine;
3-((1-methyl-2-(S)-azetidinyl)methoxy)-6-chloropyridine;
5-n-butyl-3-((1-methyl-2-(S)-pyrrolidinyl)methoxy)pyridine;
5-n-propyl-3-((1-methyl-2-(S)-pyrrolidinyl)methoxy)pyridine;
2-methyl-3-(1-methyl-2-(S)-pyrrolidinylmethoxy)pyridine;
5,6-dichloro-3-(2-(S)-azetidinylmethoxy)pyridine; and
5,6-dichloro-3-(1-methyl-2-(S)-azetidinyl)methoxy)pyridine.

or a pharmaceutically-acceptable salt or prodrug thereof.

Representative of the preferred compounds of the invention are:

3-(2-(R)-pyrrolidinylmethoxy)pyridine;
3-((1-methyl-2-(S)-pyrrolidinyl)methoxy)pyridine;
3-(2-(S)-azetidinylmethoxy)pyridine;
3-((1-methyl-2-(S)-azetidinyl)methoxy)pyridine;
3-(2-(S)-pyrrolidinylmethoxy)pyridine;
5-chloro-3-(2-(S)-pyrrolidinylmethoxy)pyridine;
5-chloro-3-((1-methyl-2-(S)-pyrrolidinyl)methoxy)pyridine;
2-methyl-3-(2-(S)-pyrrolidinylmethoxy)pyridine;
6-methyl-3-(2-(S)-pyrrolidinylmethoxy)pyridine;
6-methyl-3-((1-methyl-2-(S)-pyrrolidinyl)methoxy)pyridine;
4-methyl-3-(2-(S)-pyrrolidinylmethoxy)pyridine;
5-bromo-3-((1-methyl-2-(S)-pyrrolidiny)methoxy)pyridine;
2-methyl-3-(2-(S)-azetidinylmethoxy)pyridine;
5-chloro-3-(2-(R)-pyrrolidinylmethoxy)pyridine;
6-methyl-3-(2-(R)-pyrrolidinylmethoxy)pyridine;
3-((1-ethyl-2(S)-pyrrolidinyl)methoxy)pyridine;
5-chloro-3-(2-(S)-azetidinylmethoxy)pyridine;
6-methyl-3-(2-(S)-azetidinylmethoxy)pyridine;
2-methyl-3-(2-(R)-azetidinylmethoxy)pyridine;
3-(2-(S)-pyrrolidinylmethoxy)-6-chloropyridine;
4-methyl-3-((1-methyl-2-(S)-pyrrolidinyl)methoxy)pyridine;
3-((1-methyl-2-(R)-pyrrolidinyl)methoxy)-6-chloropyridine;
3-(2-(S)-azetidinylmethoxy)-6-chloropyridine;
6-chloro-3-((1-methyl-2-(S)-pyrrolidinyl)methoxy)pyridine;
5-bromo-3-((1-methyl-2-(R)-pyrrolidinyl)methoxy)pyridine;
3-(2-(R)-pyrrolidinylmethoxy)-6-chloropyridine;
3-((1-methyl-2-(S)-azetidinyl)methoxy)-6-methylpyridine;
3-(2-(R)-azetidinylmethoxy)pyridine;
3-((1-methyl-2-(R)-azetidinyl)methoxy)pyridine;
5-bromo-3-(2-(S)-pyrrolidinylmethoxy)pyridine;
3-(2-(S)-azetidinylmethoxy)-5-bromopyridine;
3-((1-methyl-2-(S)-azetidinyl)methoxy)-5-bromopyridine;
5-n-butyl-3-((1-methyl-2-(S)-pyrrolidinyl)methoxy)pyridine;
5-methyl-3-(1-methyl-2-(S)-pyrrolidinylmethoxy)pyridine;
5-ethyl-3-(1-methyl-2-(S)-pyrrolidinylmethoxy)pyridine;
5-n-propyl-3-((1-methyl-2-(S)-pyrrolidinyl)methoxy)pyridine;
5-chloro-3-((1-methyl-2-(S)-azetidinyl)methoxy)pyridine;
2-methyl-3-(2-(R)-azetidinylmethoxy)pyridine; and 5,6-dichloro-3-(2-(S)-azetidinylmethoxy)pyridine hydrochloride;

or a pharmaceutically-acceptable salt or prodrug thereof. Representative of the particularly preferred compounds of the invention are:

3-(2-(S)-azetidinylmethoxy)pyridine;
3-((1-methyl-2-S)-azetidinyl)methoxy)pyridine;
2-methyl-3-(2-(S)-azetidinylmethoxy)pyridine;
5-chloro-3-(2-(S)-azetidinylmethoxy)pyridine;
6-methyl-3-(2-(S)-azetidinylmethoxy)pyridine;
3-(2-(S)-azetidinylmethoxy)chloropyridine;
3-(2-(R)-azetidinylmethoxy)pyridine;
3-((1-methyl-2-(R)-azetidinyl)methoxy)pyridine;
3-(2-(S)-azetidinylmethoxy)-5-bromopyridine;
3-((1-methyl-2-(S)-azetidinyl)methoxy)-5-bromopyridine;
5,6-dichloro-3-(2-(S)-azetidinylmethoxy)pyridine.
3-(2-(R)-pyrrolidinylmethoxy)pyridine;
3-(2-(S)-pyrrolidinylmethoxy)pyridine;
5-chloro-3-(2-(S)-pyrrolidinylmethoxy)pyridine;
2-methyl-3-(2-(S)-pyrrolidinylmethoxy)pyridine;
6-methyl-3-(2-(S)-pyrrolidinylmethoxy)pyridine;
5-chloro-3-(2-(R)-pyrrolidinylmethoxy)pyridine;
6-methyl-3-(2-(R)-pyrrolidinylmethoxy)pyridine;
3-(2-(S)-pyrrolidinylmethoxy)-6-chloropyridine;
5-bromo-3-(2-(S)-pyrrolidinylmethoxy)pyridine;
3-((1-methyl-2-(S)-pyrrolidinyl)methoxy)pyridine;
5-chloro-3-(1-methyl-2-(S)-pyrrolidinyl)methoxy)pyridine;
6-methyl-3-((1-methyl-2-(S)-pyrrolidinyl)methoxy)pyridine;
5-bromo-3-((1-methyl-2-(S)-pyrrolidinyl)methoxy)pyridine;
6-chloro3-((1-methyl-2-(S)-pyrrolidinyl)methoxy)pyridine;
5-n-butyl-3-((1-methyl-2-(S)-pyrrolidinyl)methoxy)pyridine;
5-n-propyl-3-((1-methyl-2-(S)-pyrrolidinyl)methoxy)pyridine;
5-methyl-3-(1-methyl-2-(S)-pyrrolidinylmethoxy)pyridine; and
5-ethyl-3-(1-methyl-2-(S)-pyrrolidinylmethoxy)pyridine;

or a pharmaceutically-acceptable salt or prodrug thereof.

A particularly preferred embodiment is the compound, 2-methyl-3-(2-(S)-pyrrolidinylmethoxy)pyridine.

Representative of the compounds of the invention wherein the chiral center is of the (S) configuration are:

3-((1-methyl-2-(S)-pyrrolidinyl)methoxy)pyridine;
3-(2-(S)-azetidinylmethoxy)pyridine;
3-((1-methyl-2-(S)-azetidinyl)methoxy)pyridine;
3-(2-(S)-pyrrolidinylmethoxy)pyridine;
5-chloro-3-(2-(S)-pyrrolidinylmethoxy)pyridine;
5-chloro-3-((1-methyl-2-(S)-pyrrolidinyl)methoxy)pyridine;
2-methyl-3-(2-(S)-pyrrolidinylmethoxy)pyridine;
6-methyl-3-(2-(S)-pyrrolidinylmethoxy)pyridine;
6-methyl-3-((1-methyl-2-(S)-pyrrolidinyl)methoxy)pyridine;
4-bromo-3-(2-(S)-pyrrolidinylmethoxy)pyridine;
4-bromo-3-((1-methyl-2-(S)-pyrrolidinyl)methoxy)pyridine;
4-methyl-3-(2-(S)-pyrrolidinylmethoxy)pyridine;
5-bromo-3-((1-methyl-2-(S)-pyrrolidinyl)methoxy)pyridine;
2-methyl-3-(2-(S)-azetidinylmethoxy)pyridine;
2-Methyl-3-((1-methyl-2-(S)-azetidinyl)methoxy)pyridine;
3-((1-ethyl-2(S)-pyrrolidinyl)methoxy)pyridine;
5-chloro-3-(2-(S)-azetidinylmethoxy)pyridine;
6-methyl-3-(2-(S)-azetidinylmethoxy)pyridine;
2-chloro-3-(2-(S)-pyrrolidinylmethoxy)pyridine;
3-(2-(S)-pyrrolidinylmethoxy)-6-chloropyridine;
4-methyl-3-((1-methyl-2-(S)-pyrrolidinyl)methoxy)pyridine;
3-(2-(S)-azetidinylmethoxy)-6-chloropyridine;
2-methyl-3-(1-methyl-2-(S)-pyrrolidinylmethoxy)pyridine;
6-chloro-3-((1-methyl-2-(S)-pyrrolidinyl)methoxy)pyridine;
3-((1-methyl-2-(S)-azetidinyl)methoxy)-6-methylpyridine;
4-methyl-3-(2-(S)-azetidinylmethoxy)pyridine;
5-bromo-3-(2-(S)-pyrrolidinylmethoxy)pyridine;
3-(2-(S)-azetidinylmethoxy)-5-bromopyridine;
3-((1-methyl-2-(S)-azetidinyl)methoxy)-5-bromopyridine;
5-n-butyl-3-((1-methyl-2-(S)-pyrrolidinyl)methoxy)pyridine;
5-methyl-3-(1-methyl-2-(S)-pyrrolidinylmethoxy)pyridine;
5-ethyl-3-(1-methyl-2-(S)-pyrrolidinylmethoxy)pyridine;
5-n-propyl-3-((1-methyl-2-(S)-pyrrolidinyl)methoxy)pyridine
5-chloro-3-((1-methyl-2-(S)-azetidinyl)methoxy)pyridine;
3-((1-methyl-2-(S)-azetidinyl)methoxy)-6-chloropyridine;
5-n-butyl-3-((1-methyl-2-(S)-pyrrolidinyl)methoxy)pyridine;
5-n-propyl-3-((1-methyl-2-(S)-pyrrolidinyl)methoxy)pyridine;
2-methyl-3-(1-methyl-2-(S)-pyrrolidinylmethoxy)pyridine;
5,6-dichloro-3-(2-(S)-azetidinylmethoxy)pyridine; and
5,6-dichloro-3-(1-methyl-2-(S)-azetidinylmethoxy)pyridine;

or a pharmaceutically-acceptable salt or pidtig thereof.

Representative of the compounds of the invention wherein the chiral center is of the (R) configuration are:

3-((1-methyl-2-(R)-pyrrolidinyl)methoxy)pyridine;
3-(2-(R)-pyrrolidinylmethoxy)pyridine;
5-chloro-3-(2-(R)-pyrrolidinylmethoxy)pyridine;
5-chloro-3-((1-methyl-2-(R)-pyrrolidinyl)methoxy)pyridine;
2-methyl-3-(2-(R)-pyrrolidinylmethoxy)pyridine;
6-methyl-3-((1-methyl-2-(R)-pyrrolidinyl)methoxy)pyridine;
6-methyl-3-(2-(R)-pyrrolidinylmethoxy)pyridine;
2-methyl-3-(2-(R)-azetidinylmethoxy)pyridine;
3-((1-methyl-2-(R)-piperidinyl)methoxy)pyridine;
3-((1-methyl-2-(R)-pyrrolidinyl)methoxy)-6-chloropyridine;

5-bromo-3-((1-methyl-2-(R)-pyrrolidinyl)methoxy) pyridine, 3-(2-(R)-pyrrolidinylmethoxy)-6-chloropyridine;

3-(2-(R)-azetidinylmethoxy)pyridine;

3-((1-methyl-2-(R)-azetidinyl)methoxy)pyridine;

2-methyl-3-(2-(R)-azetidinylmethoxy)pyridine; and or a pharmaceutically-acceptable salt or prodrug thereof.

The present invention is also directed to pharmaceutical compositions comprising a therapeutically-effective amount of a compound of formula (I) and a pharmaceutically-acceptable carrier or diluent.

In yet another aspect of the present invention is provided the use of therapeutically-effective pharmaceutical compositions to selectively control neurotransmitter release in mammals.

Certain compounds of this invention may possess one or more asymmetric centers and may exist in optically active forms. Additional asymmetric centers may be present in a substituent group, such as an alkyl group. Pure cis-isomers and pure trans-isomers, racemic mixtures of the isomers, and mixtures thereof are intended to be within the scope of this invention. In particular, the stereochemistry at the 2-position and the point of attachment of $R^3$, as shown in Formula (I), may independently be either (R) or (S), unless specifically noted otherwise. Chiral forms of certain compounds of this invention are contemplated and are specifically included within the scope of this invention.

As used throughout the specification and appended claims, the following terms have the meanings ascribed to them:

"$C_1$–$C_3$-alkyl" and "$C_1$–$C_6$-alkyl" refer to branched or straight-chain, unsubstituted alkyl groups comprising one-to-three or one-to-six carbon atoms, including, but not limited to, methyl, ethyl, n-propyl, isopropyl, n-butyl, t-butyl, sec-butyl or isobutyl, or additionally, for $C_1$–$C_6$-alkyl, neopentyl or n-hexyl and the like.

The term, "prodrug", refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Deliverm Systems*, Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application*, edited by E. B. Roche, Pergamon Press (1987).

The term, "prodrug ester group", refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term, "administration", of the cholinergic agent or composition, as used herein, refers to systemic use as when taken orally, parenterally, by inhalation spray, by nasal, rectal or buccal routes, or topically as ointments, pastes, creams, lotions, gels, powders, solutions, sprays, inhalants or transdermal patches in dosage form unit formulations containing conventional nontoxic pharmaceutically acceptable carriers, adjuvants and vehicles as desired.

The term "parenteral", as used herein, includes intravenous, intramuscular, intraperitoneal, intrasternal, subcutaneous and intraarticular injection as well as via infusion techniques.

By "pharmaceutically-acceptable", it is meant those salts, amides and esters which are, within the scope of sound medical judgement, suitable for use in contact with the tissues of humans and animals without undue toxicity, irritation, allergic response and the like, and are commensurate with a reasonable benefit/risk ratio, effective for their intended use in the treatment of psychological, neurological, cardiovascular and addictive behavior disorders. Pharmaceutically-acceptable salts are well known in the art. For example, S. M. Berge, et al. describe pharmaceutically-acceptable salts in detail in *J. Pharmaceutical Sciences*, 66: 1–19, 1977. The salts may be prepared in situ during the final isolation and purification of the compounds of Formula (I), or separately by reacting the free base function with a suitable organic acid. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like. Examples of pharmaceutically-acceptable, nontoxic amides of the compounds of Formula I include amides derived from $C_1$–$C_6$-alkyl carboxylic acids wherein the alkyl groups are straight- or branched-chain, aromatic carboxylic acids such as derivatives of benzoic acid and heterocyclic carboxylic acids, including furan-2-carboxylic acid or nicotinic acid. Amides of the compounds of Formula I may be prepared according to conventional methods and include amino acid and polypeptide derivatives of the amines of Formula I.

As used herein, the term, "pharmaceutically-acceptable carriers", means a non-toxic, inert solid, semi-solid or liquid filler, diluent, encapsulating material or formulation auxiliary of any type. Some examples of the materials that may serve as pharmaceutically-acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants may also be present in the composition, according to the judgement of the formulator. Examples of pharmaceutically-acceptable antioxidants include water-soluble antioxidants, such as ascorbic acid, cysteine hydrochloride, sodium bisulfite, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like, By a "therapeutically-effective amount" of the cholinergic channel ligand agent, is meant a sufficient amount of the compound to treat cholinergically-related disorders at a reasonable benefit/risk ratio applicable to obtain a desired therapeutic response. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the tretment; drugs used in combination or coincidentally with the specific compound employed; and like factors well known in the medical arts. Total daily dose of the compounds of this invention administered to a host in single or divided doses may be in amounts as determined by the attending physician, typically, for example, in amounts of from about 0.001 to 100 mg/kg body weight daily and preferably 0.01 to 10 mg/kg/day. Dosage unit compositions may contain such amounts of submultiples thereof to make up the daily dose.

The present invention includes one or more of the compounds of formula (I) prepared and formulated with one or more non-toxic pharmaceutically-acceptable compositions, as described below.

Compositions suitable for parenteral injection may comprise pharmaceutically-acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

If desired, and for more effective distribution, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatin, polyvinylpyrrolidone, sucrose and acacia; (c) humectants, as for example, glycerol; (d) disintegrating agents, as for example, agar—agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar, as well as high molecular weight polyethylene glycols, and the like.

Solid dosage forms such as tablets, dragees, capsules, pills and granules may be prepared with coatings and shells, such as enteric coatings and others well known in this art. They may contain pacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacahth, or mixtures of these substances, and the like.

Compositions for rectal or vaginal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical or transdermal administration of a compound of this invention further include ointments, pastes, creams, lotions, gels, powders, solutions, sprays, inhalants or transdermal patches. Transdermal administration via a transdermal patch is a particularly effective and preferred dosage form of the present invention. The active component is admixed under sterile conditions with a pharmaceutically-acceptable carrier and any needed preservative, buffers or propellants as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulations, eye ointments, powders and solutions are also contemplated as being within the scope of this invention.

The present compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes may be used. The present compositions in liposome form may contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., (1976), p 33 et seq.

In order to reduce unwanted peripherally-mediated side-effects, it is advantageous, but not essential, to incorporate into the composition a peripherally-acting anti-cholinergic such as N-methylscopolamine, N-methylatropine, propantheline, methantheline, or glycopyrrolate.

Compounds of the invention which have one or more asymmetric carbon atoms may exist as the optically-pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof. The terms "R" and "S" used herein are configurations as defined in *IUPAC 1974 Recommendations for Section E, Fundamental Stereochemistry, Pure Appl. Chem.*, 1976, 45: 13–30.

The compounds of the present invention may be synthesized as shown in reaction schemes I and II presented below using the reactions and techniques described in this section. The reactions are performed in a solvent appropriate to the reagents and materials employed are suitable for the transformation being effected. It is understood by those skilled in the art of organic synthesis that the functionality present on the heterocyclic ring and other portions of the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of nitrogen-protecting groups is well known in the art for protecting amino groups against undesirable reactions during a synthetic procedure and many such protecting groups are known, cf, for example, T. W. Greene and P. G. M. Wuts, *Protective Groups in Organic Synthesis*, 2nd edition, John Wiley & Sons, New York (1991).

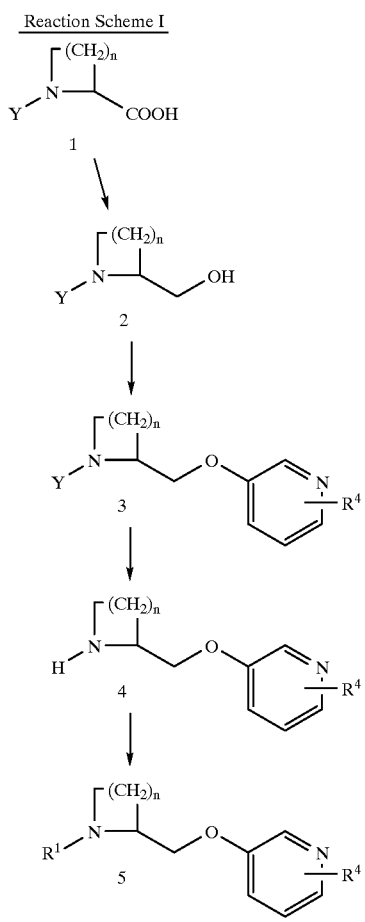

Reaction Scheme I

In accordance with Scheme I, compounds of Formula (I) wherein B is selected from option (ii) are prepared by reacting a 2-carboxyl-substituted azacycloalkyl compound (1), wherein n is as described above, $R^3$ is H and wherein the Y is a $C_1$–$C_3$-alkyl or a suitable protecting group, such as BOC or CBZ, for example, which may subsequently be removed and replaced with H, allyl, or $C_1$–$C_3$-alkyl, is converted to the hydroxymethyl compound of formula (2) with a suitable reducing agent, such as Red-Al®, borane/THF, borane/methyl sulfide or LiAlH$_4$, for example. Compound (2) is reacted with an appropriate 3-hydroxypyridine compound, which is substituted with the appropriate $R^4$ group, wherein $R^4$ is as described above, or is an appropriately protected $R^4$ group, wherein the protecting group may be removed after the coupling reaction, in the presence of triphenylphosphine and DEAD as described by O. Mitsunobu (*Synthesis*, 1981: 1) to form the pyridine compound of formula (3). This compound is then treated with a reagent suitable for removing the N-protecting group, such as trifluoroacetic acid, HCl in glacial acetic acid or HBr in acetic acid, for example, to form the unprotected compound (4). The ring nitrogen is then alkylated, with for example, treatment with alkyl halide in the presence of a base, formaldehyde in formic acid, or with an aldehyde and sodium cyanoborohydride, in an alcohol solvent, such as methanol, ethanol or isopropanol, or by reaction with the appropriate allylating reagent, such as, for example, allyl bromide, to give the desired compound (5), wherein $R^1$ is as described above, which is compound (I), wherein A is selected from option (i) and B is selected from option (ii).

IN VITRO DETERMINATION OF STRIATAL DOPAMINE RELEASE AND NEURONAL NICOTINIC RECEPTOR BINDING POTENCIES AND SELECTIVITY

Several compounds of the present invention were tested for their ability stimulate dopamine release or inhibit nicotine-evoked dopamine release using a striatal dopamine release assay. The protocol for this procedure follows below.

A. Protocol for Determination of Striatal Dopamine Release.

nAChR evoked release of [ring-2,5,6-$^3$H]-dopamine (24.4 Ci/mmol) was measured in superfused rat striatal slices. Striata were dissected from two male Sprague-Dawley rats per experiment and sliced 0.35×0.25 mm by a McIlwain Tissue Chopper (Brinkman Instrument Co., Westbury, N.Y.). After two washes with Krebs-HEPES buffer (137 mM NaCl, 4.7 mM KCl, 1 mM $MgSO_4$, 2.5 mM $CaCl_2$, 1.25 mM $NaH_2PO_4$, 10 mM glucose, 15 mM HEPES-NaOH, pH 7.4, containing 10 μM pargyline and 10 μM ascorbic acid), slices were preincubated for 10 minutes at 37° C. under 95%/5% $O_2/CO_2$. After replacing the buffer, slices were labeled with 100 nM [$^3$H]-dopamine for 25 min in Krebs-HEPES at 37° C. Aliquots of slices were placed in 18 superfusion chambers of a Brandel SP2000 superfusion apparatus (Brandel, Gaithersberg, Md.). Following 47 minutes of washout, slices were exposed to agonist at various concentrations for 4 minutes. Antagonists or inhibitors, when present were introduced 4 minutes prior to and during agonist exposure. Collected fractions were counted in 5 mL of Ecolume. Tissue was recovered from superfusion chambers, solubilized with 1 mL of Solvable™ (DuPont-NEN) and counted in 15 mL of Ecolume. Fractional release of [$^3$H]-dopamine was calculated from radioactivity above baseline as a fraction of total radioactivity. Relative potencies were calculated using the release evoked by 100 nM (−)-nicotine as a standard.

For the purpose of identifying compounds as cholinergic agents which are capable of interacting with cholinergic channel receptors in the brain, a ligand-receptor binding assay was carried out as the initial screen. Compounds of the present invention were effective at interacting with neuronal nicotinic cholinergic receptors as assayed for their ability (compared to (−)-nicotine) to displace radioligand from neuronal nicotinic cholinergic channel receptors labeled with [$^3$H]-cytisine ([$^3$H]-CYT).

The ability of the compounds of the invention to interact with cholinergic channel receptors and thereby to activate or inhibit neurotransmitter release can be demonstrated in vitro using the following protocol.

B. Protocol For Determination of Nicotinic Cholinergic Channel Receptor Binding Potencies of Ligands Binding of [$^3$H]-cytisine ([$^3$H]-CYT) to nicotinic receptors was accomplished using crude synaptic membrane preparations from whole rat brain (Pabreza et al., *Molecular Pharmaol.*, 1990, 39:9). Washed membranes were stored at −80° C. prior to use. Frozen aliquots were slowly thawed and resuspended in 20 volumes of buffer (containing: 120 mM NaCl, 5 mM KCl, 2 mM $MgCl_2$, 2 mM $CaCl_2$ and 50 mM Tris-Cl, pH 7.4 @4° C.). After centrifuging at 20,000×g for 15 minutes, the pellets were resuspended in 30 volumes of buffer. Homogenate (containing 125–150 mg protein) was added to triplicate tubes containing concentrations of test compound and [$^3$H]-CYT (1.25 nM) in a final volume of 500 μL. Samples were incubated for 60 minutes at 4° C., then rapidly filtered through Whatman GF/B filters presoaked in 0.5% polyethylimine using 3×4 mL of ice-cold buffer. The filters are counted in 4 mL of Ecolume® (ICN). Nonspecific binding was determined in the presence of 10 μM (−)-nicotine and values were expressed as a percentage of total binding. $IC_{50}$ values were determined with the RS-1 (BBN) nonlinear least squares curve-fitting program and $IC_{50}$ values were converted to Ki values using the Cheng and Prusoff correction ($Ki=IC_{50}/(1+[ligand]/Kd$ of ligand). Alternately, data were expressed as a percentage of the total specific binding. The results (shown in Tables 1 and 2) suggest that the compounds of the present invention have affinity for the neuronal nicotinic cholinergic channel receptor.

D. Protocols for the Determination of Cholinergic Channel Activation in PC12 Cells.

The cholinergic channel activator properties of Example 9 were investigated in PC12 cells using the whole-cell patch-clamp approach to measure current flow through ligand-gated membrane channels. The electrophysiological approach demonstrates clear agonist activity of the activator, and indicates that this is due to direct activation of cholinergic ligand-gated channels.

Data in Table 1 show that compounds of the present invention bind to high-affinity nicotine receptors and control dopamine release. This finding is in agreement with the results of others who have linked dopamine release to binding at nicotinic receptors (cf., for example, Lippiello and Caldwell, U.S. Pat. No. 5,242,935, issued Sep. 7, 1993; Caldwell and Lippiello, U.S. Pat. No. 5,248,690, issued Sep. 28, 1993; and Wonnacott et al., *Prog. Brain Res.*, 79: 157–163 (1989)).

TABLE 1

Binding to Neuronal Nicotinic Receptors and Control of Dopamine Release

| Example | Receptor Binding Ki (nM) | Dopamine Release relative to Nicotine≠ |
|---|---|---|
| (−)-nicotine | 0.69 | 1.0 |
| 1 | 23 | 0.08* |
| 4 | 0.2 | 1.0* |
| 8 | 33 | 0.55** |
| 9 | 0.05 | 1.0* |
| 10 | 0.25 | 1.0* |
| 14 | 0.14 | 1.0** |
| 16 | 0.6 | 1.0** |
| 17 | 16.7 | 0.7* |
| 18 | 0.28 | 1.0*** |
| 19 | 1.47 | 0.78*** |
| 31 | 0.7 | 0.15* |
| 33 | 0.2 | 0.62** |
| 37 | 0.5 | 0.8* |
| 38 | 13 | 0.6* |
| 46 | 4 | 0.85* |
| 52 | 0.04 | 1.0* |
| 59 | 4.5 | 0.7* |

≠ example concentration: * = 10 μM;  = 1 μM; * = 0.1 μM

Nicotinic binding data of additional compounds of the present invention are given in Table 2.

TABLE 2

Binding to Neuronal Nicotinic Receptors

| Example number | Receptor Binding Ki (nM) |
|---|---|
| (−)-nicotine | 0.69 |
| 2 | 0.17 |
| 3 | 20 |
| 5 | 87 |
| 6 | 6.7 |
| 7 | 0.44 |
| 11 | 110 |

TABLE 2-continued

Binding to Neuronal Nicotinic Receptors

| Example number | Receptor Binding Ki (nM) |
|---|---|
| 12 | 29 |
| 13 | 65 |
| 15 | 0.13 |
| 20 | 341 |
| 21 | 23 |
| 22 | 25 |
| 23 | 78.3 |
| 24 | 4.2 |
| 25 | 14.7 |
| 26 | 76 |
| 27 | 5.8 |
| 28 | 0.23 |
| 29 | 1.3 |
| 30 | 129 |
| 32 | 110 |
| 34 | 11 |
| 35 | 39 |
| 36 | 26 |
| 39 | 0.04 |
| 40 | 0.05 |
| 41 | 9.9 |
| 42 | 342 |
| 43 | 18.6 |
| 44 | 1.8 |
| 45 | 0.075 |
| 47 | 23 |
| 48 | 30 |
| 49 | 66 |
| 50 | 5.6 |
| 51 | 4.5 |
| 53 | 28 |
| 54 | 78 |
| 55 | 0.63 |
| 56 | 9.2 |
| 57 | 17 |
| 58 | 5.3 |
| 60 | 51 |
| 61 | 1.3 |
| 62 | 0.5 |
| 63 | 1.4 |
| 64 | 224 |
| 65 | 0.6 |
| 66 | 4 |
| 67 | 0.2 |
| 68 | 4.5 |
| 69 | 2.1 |
| 70 | 0.6 |
| 71 | 0.1 |
| 72 | 110 |
| 73 | 0.48 |
| 74 | 59 |
| 75 | 0.32 |
| 76 | 12.8 |
| 77 | 0.1 |
| 78 | 5.77 |
| 79 | 42.8 |
| 80 | 1.9 |
| 81 | 9.3 |
| 82 | 72.4 |
| 83 | 73.1 |
| 84 | 2.41 |
| 85 | 16 |
| 86 | 1.43 |
| 87 | 0.11 |
| 88 | 10.4 |
| 89 | 91.2 |
| 90 | 18.4 |
| 91 | 1.47 |
| 92 | 141 |
| 94 | 0.5 |
| 102 | 34.9 |
| 103 | 18.4 |
| 105 | 33.1 |
| 108 | 4.9 |
| 109 | 0.024 |
| 110 | 0.75 |

The following examples, which are provided for illustration and not limitation of the invention, will serve to further illustrate preparation of the novel compounds of the invention and their biological activity. Thin-layer chromatography (TLC) was performed on 0.25 mm E. Merck precoated silica gel plates (60 F-254). Flash chromatography was performed on 200–400 mesh silica gel (E. Merck), while column chromatography was performed on 70–230 mesh silica gel (E. Merck).

The following abbreviations are used: THF for tetrahydrofuran, DMF for N,N-dimethylformamide, $D_2O$ for deuterium oxide, $CDCl_3$ for deuterochloroform, DMSO-$d_6$ for deuterodimethylsuffoxide, BOC for t-butyloxycarbonyl, CBZ for benzyloxycarbonyl, Bz for benzyl, Ms for methanesulfonyl, PAW for pyridine/acetic acid/water (20:6:11), DCC for dicyclohexylcarbodiimide, DIBAL for diisobutylaluminum hydride, DIEA for diisopropylethylamine, DPPA for diphenylphosphoroazidate, dppp for [1,3-bis (diphenylphosphino)propane, EDCI for 1-(3-dimethylaminopropyl)-3-ethylcarbodiimide hydrochloride, EtOH for ethanol, IBCF for isobutyl chloroformate, HOAc for acetic acid, HOBT for 1-hydroxybenzotriazole, LAH for lithium aluminum hydride, $NH_4OAc$ for ammonium acetate, NMM for N-methylmorpholine, TEA for triethylamine.

EXAMPLE 1

3-((1-methyl-2-(R)-pyrrolidinyl)methoxy)pyridine hydrochloride 1a. 3-((1-methyl-2-(R)-pyrrolidinylmethoxy)pyridine To a solution of triphenylphosphine (509 mg, 1.94 mmol) in 10 mL of tetrahydrofuran at room temperature was added diethyl azodicarboxylate (DEAD) (0.35 mL, 1.94 mmol) dropwise with stirring. After stirring at room temperature for 30 minutes, (R)-1-methyl-2-pyrrolidinemethanol (Aldrich Chemical Co., 150 mg, 1.30 mmol) and 3-hydroxypyridine (Aldrich Chemical Co., 185 mg, 1.94 mmol) were added to the reaction mixture. The resultant solution was then stirred at room temperature overnight. After all of the starting material was consumed, the organic solvent was evaporated in vacuo. The residue was purified by column silica gel chromatography eluting with chloroform:methanol (10: 1) to provide 76 mg (21% yield) of the title compound. MS (DCI/$NH_3$) m/e 193 (M+H)$^+$. $^1$H NMR ($CDCl_3$, 300 MHz) δ: 8.32 (t, J=1.5 Hz, 1H), 8.22 (t, J=3 Hz, 1H) 7.24–7.2 (m, 2H), 4.14–4.05 (dd, J=9, 6 Hz, 1H), 4.00–3.93 (dd, J=9, 6 Hz, 1H), 3.24–3.14 (m, 1H), 2.81–2.7 (m, 1H, 2.54 (s, 3H), 2.44–2.31 (m, 1H), 2.14–2.00 (m, 1H, 1.96–1.71 (m, 3H).

1b. 3-((1-methyl-2-(R)-pyrrolidinyl)methoxy)pyridine hydrochloride

The compound from step 1a above (76 mg, 0.4 mmol) was dissolved in ethanol. Hydrochloric acid in diethyl ether was added dropwise to a stirring solution of base at ambient temperature. The resultant white precipitate was then collected by evaporation of solvent and triturated with three portions of diethyl ether. The hygroscopic solid was obtained in 50% yield (53 mg). MS (DCI/$NH_3$) m/e 193

(M+H)+. 1H NMR (D2O, 300 MHz) δ: 8.43 (br s, 1H), 8.33 (d, J=5.6 Hz, 1H), 7.88–7.82 (m, 1H), 7.72 (dd, J=8.50, 5.15 Hz, 1H), 4.59 (dd, J=11, 3 Hz, 1H), 4.42 (dd, J=11.4, 6.2 Hz, 1H), 4.17–4.25 (m, 1H), 4.05–3.9 (m, 1H), 3.82–3.74 (m, 1H), 3.34–3.22 (m, 1H), 3.04 (s, 3H), 2.42–2.36 (m, 1H), 2.26–2.06 (m, 3H). Analysis calculated for $C_{11}H_{16}N_2O.HCl.0.2\ H_2O$: C, 49.15; H, 6.90; N, 10.42; Found: C, 48.90; H, 7.17; N, 10.89. $[\alpha]^{25}_D$=+6.54° (c=1, MeOH).

EXAMPLE 2

3-(2-(R)-pyrrolidinylmethoxy)pyrridine dihydrochloride 2a. 3-(1-t-butoxycarbonyl-2-(R)-pyrrolidinylmethoxy)pyridine To a solution of triphenylphosphine (1.24 g, 4.74 mmol) in 20 mL of tetrahydrofuran at room temperature was added diethyl azodicarboxylate (0.746 mL, 4.74 mmol) dropwise with stirring. After stirring at room temperature for 30 minutes, (R)-1-t-butoxycarbonyl-2-pyrrolidinemethanol (350 mg, 3.16 mmol) and 3-hydroxypyridine (450 mg, 4.74 mmol) were added to the reaction mixture. The resultant solution was then stirred at room temperature overnight. After all of the starting material was consumed, the organic solvent was evaporated in vacuo. The residue was purified by silica gel column chromatography. Elution with chloroform:methanol (10:1) provided 518 mg of the title compound along with substantial amount of reduced DEAD reagent. MS (DCI/NH3) m/e 279 (M+H)+.

2b. 3-(2-(R)-pyrrolidinylmethoxy)pyridine

To a solution of the compound of Example 2a in 2 mL of methylene chloride solution was added 2 mL of trifluoroacetic acid. The resultant solution was stirred at room temperature for 2.5 hour. Evaporation of both solvent and trifluoroacetic acid gave a brown oil which was basified with saturated ammonium hydroxide solution. This oil was purified by silica gel column chromatography. Elution with a mixture of chloroform:methanol:ammonium hydroxide (10:1:0.1) provided the desired product. MS (DCI/NH3) m/e 179 (M+H)+. 1H NMR (D2O, 300 MHz) δ: 8.33 (br s, 1H), 8.22 (m, 1H), 7.22(m, 2H), 3.82–4.03 (m, 2H), 3.50–3.61 (m, 1H), 2.92–3.10(m, 2H), 1.70–2.10 (m, 4H), 1.51–1.66 (m, 1H).

2c. 3-(2-(R)-pyrrolidinylmethoxy)pyridine dihydrochloride

The compound from Example 2b (76 mg, 0.4 mmol) was dissolved in ethanol. Hydrochloric acid in diethyl ether was added dropwise to a stirring solution of base at ambient temperature. The resultant white precipitate was then collected by evaporation of solvent and triturated with three portions of diethyl ether. The hygroscopic solid was obtained in 50% yield (53 mg). MS (DCI/NH3) m/e 179 (M+H)+. 1H NMR (D2O, 300 MHz) δ: 8.43 (br s, 1H), 8.34 (br s 1H), 7.85(dd, J=8.80, 2.90 Hz, 1H), 7.72 (dd, J=8.80, 5.15 Hz, 1H), 4.54 (dd, J=11, 3.3 Hz, 1H), 4.32 (dd, J=10.6, 3.3 Hz, 1H), 4.10–4.19 (m, 1H), 3.42 (t, J=7.5 Hz, 1H), 2.27–2.35 (m, 1H), 2.06–2.21 (m, 2H), 1.90–2.02 (m, 1H). Anal. calc. for $C_{10}H_{14}N_2O.2.4\ HCl$: C, 45.20; H, 6.22; N, 10.54; Found: C, 45.12; H, 6.00; N, 10.33.

EXAMPLE 3

2-((1-methyl-2-(S)-pyrrolidinyl)methoxy)pyrazine fumarate 3a. 2-((1-methyl-2-(S)-pyrrolidinyl)methoxy)pyrazine (S)-(-)-1-Methyl-2-pyrrolidinemethanol (Aldrich Chemical Co., 0.5 g, 4.34 mmol) was dissolved in anhydrous THF and brought to 0° C. NaH ((80% dispersion in mineral oil), 131 g, 4.56 mmol) was added and the reaction mixture was allowed to warm to room temperature with stirring. After 30 minutes 2-chloropyrazine (0.497 g, 4.34 mmol) was added via syringe. The mixture was stirred for 48 hours. The solvent was then evaporated in vacuo and the mixture diluted with chloroform, washed with saturated NaHCO3 and a brine solution. The organic layer was then dried over MgSO4. The resulting crude material was purified by flash chromatography (10% MeOH/CHCl3) to give 0.81 g (97% yield) of the title compound as an oil. TLC $R_f$=0.3 (10% MeOH/CHCl3). MS (DCI/NH3) m/e 194 (M+H)+. 1H NMR (CDCl3, 300 MHz) δ: 8.24 (d, J=1.5 Hz, 1H, 8.11 (d, J=3 Hz, 1H), 8.07 (dd, J=3, 1.5 Hz, 1H), 4.36 (dd, J=9, 6 Hz, 1H), 4.28 (dd, J=9, 6 Hz, 1H), 3.16–3.08 (m, 1H, 2.7–2.58 (m, 1H, 2.47 (s, 3H), 2.34–2.24 (m, 1H, 2.08–1.93 (m, 1H, 1.91–1.67 (m, 3H).

3b. 2-((1-methyl-2-(S)-pyrrolidinyl)methoxy)pyrazine fumarate

The compound of step 3a was dissolved in anhydrous MeOH and brought to 0° C. with stirring. Fumaric acid was dissolved in MeOH with sonication and added dropwise to the base. The mixture was warmed to room temperature with stirring. After 30 minutes the solvent was evaporated in vacuo and the remaining solid was triturated with anhydrous diethyl ether. The resulting white solid was vacuum filtered to yield 0.117 g (50% yield) of product. m.p.=116–118° C. MS (DCI/NH3) m/e 194 (M+H)+. 1H NMR (D2O, 300 MHz) δ: 8.33 (d, J=1.1 Hz, 1H), 8.23–8.21 (m, 2H), 6.65 (br s, 2H), 4.76–4.71 (dd, J=12.5, 3 Hz, 1H), 4.60–4.54 (dd, J=12.5, 6 Hz, 1H, 3.98–3.9 (m, 1H), 3.8–3.72 (m, 1H), 3.3–3.2 (m, 1H), 3.04 (s, 3H), 2.45–2.32 (m, 1H, 2.28–2.01 (m, 3H). Analysis calculated for $C_{10}H_{15}N_3O.C_4H_4O_4$: C, 54.36; H, 6.19; N, 13.58; Found: C, 54.23; H, 6.04; N, 13.58.

EXAMPLE 4

3-((1-methyl-2-(S)-pyrrolidinyl)methoxy)pyridine fumarate 4a. 3-((1-methyl-2-(S)-pyrrolidinyl)methoxy)pyridine (S)-1-Methyl-2-pyridinemethanol was reacted with triphenylphosphine, DEAD and 3-hydroxypyridine according to the procedure outlined in Example 1a The crude product was purified by flash chromatography (2×) using (10% MeOH/CHCl3) to remove the diethyl hydrazine dicarboxylate impurity and give a yellow oil in 31% yield. MS (DCI/NH3) m/e 193 (M+H)+. 1H NMR (CDCl3, 300 MHz) δ: 8.32 (t, J=1.5 Hz, 1H), 8.22 (t, J=3 Hz, 1H), 7.24–7.2 (m, 2H), 4.14–4.05 (dd, J=9, 6 Hz, 1H), 4.00–3.93 (dd, J=9, 6 Hz, 1H), 3.243.14 (m, 1H, 2.81–2.7 (m, 1H), 2.54 (s, 3H), 2.44–2.31 (m, 1H, 2.14–2.00 (m, 1H, 1.96–1.71 (m, 3H).

4b. 3-((1-methyl-2-(S)-pyrrolidinyl)methoxy)pyridine fumarate

The compound of step 4a was dissolved in anhydrous MeOH and brought to 0° C. with stirring. Fumaric acid was dissolved in MeOH with sonication and added dropwise to the solution containing amine. The mixture was warmed to room temperature with stirring. After 30 minutes the solvent was evaporated in vacuo and the remaining solid was vacuum filtered. The solid was then recrystallized with MeOH/Et2O to give the desired product as a white powder (21% yield). m.p.=124–125° C. $[\alpha]^{25}_D$=-3.9° (c=1, MeOH). MS (DCI/NH3) m/e 193 (M+H)+. 1H NMR (D2O, 300 MHz) δ: 8.43 (br s, 1H, 8.33 (d, J=4.5 Hz, 1H), 7.88–7.84 (m, 1H), 7.3 (dd, J=8.82, 5.15 Hz, 1H), 6.58 (s, 2H), 4.59 (dd, J=11, 3 Hz, 1H), 4.42 (dd, J=11, 5.98 Hz, 1H), 4.05–3.9 (m, 1H), 3.82–3.74 (m, 1H, 3.343.22 (m, 1H), 3.05 (s, 3H), 2.47–2.37 (m, 1H), 2.30–2.06 (m, 3H). Analysis calculated for $C_{11}H_{16}N_2O.C_4H_4O_4$: C, 58.43; H, 6.54; N, 9.09; Found: C, 58.32; H, 6.67; N, 8.99.

EXAMPLE 5

2-((1-methyl-2-(R)-pyrrolidinyl)methoxy)-6-chloropyridazine oxalate 5a. 2-((1-methyl-2-(R)-pyrrolidinyl)methoxy)-6-chloropyridazine (R)-1-Methyl-2-pyrrolidinemethanol (300 mg, 2.61 mmol) was dissolved in anhydrous THF and cooled to 0° C. with stirring. NaH (80% dispersion in mineral oil, 0.082 g, 2.9 mmol) was added and the mixture was slowly warmed to room temperature with stirring. After 30 minutes a THF solution of 3,6-dichloropyridazine (0.41 g, 2.74 mmol) was added to the mixture via syringe. The reaction was stirred for 48 hours. The solvent was then evaporated in vacuo and the mixture diluted with chloroform, washed with saturated $NaHCO_3$ and then with brine. The organic layer was dried over $MgSO_4$. The resulting crude material was purified by flash chromatography (10% $MeOH/CHCl_3$) to give 0.25 g (42% yield) of the title compound as a cream colored solid. MS ($DCI/NH_3$) m/e 228 $(M+H)^+$. $[\alpha]^{25}_D = +32°$ (c=1, MeOH).

5b. 2-((1-methyl-2-(R)-pyrrolidinyl)methoxy)-6-chloropyridazine oxalate

The compound of step 5a was dissolved in anhydrous ether and cooled to 0° C. with stirring. Oxalic acid, predissolved in ether, was added dropwise to the solution and mixture warmed to room temperature. After 30 minutes of stirring, the solvent was removed in vacuo and the resulting solid was recrystallized with $MeOH/Et_2O$ to yield 0.28 g (82% of the title compound as a white powder. m.p.= 153–154° C. MS ($DCI/NH_3$) m/e 228 $(M+H)^+$. $^1$H NMR ($D_2O$, 300 MHz) δ: 7.76 (d, J=9 Hz, 1H), 7.36 (d, J=9 Hz, 1H), 4.83 (dd, J=12, 3 Hz, 1H), 4.66 (dd, J=12, 6 Hz, 1H), 4.0–3.92 (m, 1H), 3.8–3.72 (m, 1H), 33–3.21 (m, 1H), 3.04 (s, 3H), 2.46–2.37 (m, 1H), 2.28–2.02 (m, 3H). Analysis calculated for $C_{10}H_{14}N_3OCl \cdot C_2H_2O_4$: C, 45.36; H, 5.08; N, 13.23; Found C, 45.46; H, 5.02, N, 13.26.

EXAMPLE 6

3-(a-methyl-(1-methyl-2-(S)-pyrrolidinyl)methoxy) pyridine hydrochloride

6a. N-(carbobenzyloxy)-a-methyl-2-pyrrolidinemethanol

To a solution of N-carbobenzyloxy-prolinal (1.0 g, 4.28 mmol, see Mori et al., *Tetrahedron*, 1985, 41:5465) in $Et_2O$ (15 mL) at 0° C. was added methyl Grignard (1.4M in THF/toluene; 3.36 mL, 4.71 mmol), and two more 1 mL aliquots of methyl Grignard were added at 5 minute intervals. The reaction mixture was then diluted with $Et_2O$ (100 mL) and washed with 150 mL portions of 5% aq. HCl (1×), and brine (1×), dried ($MgSO_4$), and concentrated to afford the crude product as a clear oil (956 mg). Chromatographic purification (silica, EtOAc/Hex 1:2) afforded the product as a mixture of diastereomers (432 mg, 40% yield). $^1$H-NMR ($CDCl_3$) δ: 7.36 (m, 5H); 5.15 (s, 2H); 4.02 (br s, 1H); 3.86–3.39 (m, 4H); 2.06–1.60 (m, 4H); 1.18, 1.11(two d, 3). MS($DCI/NH_3$) m/e 250 $(M+H)^+$.

6b. a,1-dimethyl-2-(S)-pyrrolidinemethanol

To a solution of the compound of step 6a (224 mg, 0.898 mmol) in $Et_2O$ (6 mL) was added LAH (~50 mg, excess) and the reaction mixture refluxed for 0.5 hours, then stirred at room temperature for 17 hours. The reaction mixture was then quenched with $Na_2SO_4$ decahydrate (~500 mg) followed by EtOAc (6 mL), then filtered and the salts washed with ethanol. The combined washes were combined and concentrated to afford the crude product as a gel (138 mg). $^1$H-NMR ($CDCl_3$) δ: 3.87, 3.72, 3.40, 3.05 (m, 2); 2.47, 2.32 (two s, 3); 2.44–2.33 (m, 1); 1.98–1.84 (m, 1); 1.83–1.63, 1.55–1.45 (m, 4); 1.16, 1.12(two d, 3). MS(DCI/NH3) m/e 130 $(M+H)^+$.

6c. 3-(a-methyl-(1-methyl-2-(S)-pyrrolidinyl)methoxy) pyridine hydrochloride

To a solution of triphenylphosphine (353 mg, 1.34 mmol) in THF (4 mL) at 0° C. was added DEAD (212 mL, 1.34 mmol), and after 3 minutes a solution of the product of Example 6b (116 mg, 0.897 mmol) and 3-hydroxypyridine (94 mg, 0.98 mmol) in THF (5 mL) was added. The reaction mixture was stirred at 0° C. for 6 hours then at room temperature for 15 hours. The reaction mixture was then diluted with $CH_2Cl_2$ (30 mL) and washed with 10-mL portions of 10% aq. NaOH (2×) followed by 10% aq. HCl (3×). The combined acidic aqueous layers were basified to pH 14 and extracted with $CH_2Cl_2$ (3×10 mL), the combined $CH_2Cl_2$ washes dried ($MgSO_4$) and concentrated to afford the crude product. Treatment with 40% KOH (to remove DEAD by-product) followed by chromatographic purification (silica, $EtOAc/EtOH/NH_4OH$ 100:30:0.5) afforded the product as a mixture of diastereomers, which was converted to the hydrochloride salt as a white hygroscopic solid. (9 mg, 4% yield). $^1$H-NMR ($D_2O$) δ: 8.58, 8.47, 8.26, 8.04 (four m, 4), 5.07–4.89 (m, 1); 3.97–3.52 (m, 2); 3.34–3.14 (m, 1); 3.09, 2.93 (two s, 3); 3.07–2.84 (m, 1); 2.53–1.78 (m, 4); 1.50, 1.44 (two d, 3). MS(DCI/NH3) m/e 207 $(M+H)^+$.

EXAMPLE 7

2-(2-(S)-azetidinylmethoxy)pyrazine dihydrochloride 7a. 1-t-butyloxycarbonyl-2-(S)-azetidinecarboxylic acid To an ice cooled solution of 2-(S)-azetidinecarboxylic acid (10.15 g, 100.39 mmol) in 1,4 dioxane:water (300 mL, 1:1) was added di-tert-butyl dicarbonate (28.48 g, 130.51 mmol), followed by 4-methylmorpholine (11.68 g, 115.45 mmol). The reaction mixture continued to stir 18 hours, gradually warming to room temperature. The reaction mixture was then poured into a ice cooled saturated solution of sodium bicarbonate (250 mL) and washed with ethyl acetate (3×250 ml). The aqueous was then acidified with potassium hydrogen sulfate (pH=1) and the product extracted with ethyl acetate (3×300 ml). These extracts were then dried ($Na_2SO_4$), filtered and concentrated in vacuo. The resulting semisolid was carried forward without further purification. MS ($DCI/NH_3$) m/e 202 $(M+H)^+$, 219 $(M+NH_4)^+$. $^1$H NMR ($CDCl_3$, 300 MHz) δ: 10.0 (br s, 1H), 4.81–4.76 (t, J=15 Hz, 1H), 3.99–3.83 (m, 2H), 2.62–2.38 (m, 2H), 1.48 (s, 9H).

7b. 1-t-butyloxycarbonyl-2-(S)-azetidinemethanol

To an ice-cooled solution of the compound of step 7a (9.39 g, 46.72 mmol) in tetrahydrofuran (100 mL) was added borane/THF complex (1 M, 210 mL, 4.5 eq.) under nitrogen. The reaction was gradually warmed to room temperature and stirred for 48 hours, after which a 10% aqueous potassium hydrogen sulfate solution (60 mL) was added gradually, then the volatiles were evaporated in vacuo. The remaining slurry was diluted with ethyl acetate (100 mL), and triturated two additional times. The organic phase was then washed with a saturated solution of sodium hydrogen carbonate (3×75 mL), dried ($MgSO_4$), filtered and concentrated in vacuo, yielding a colorless oil (8.4 g, 96% yield). This material was carried forward without further purification. MS ($DCI/NH_3$) m/e 188 $(M+H)^+$. $^1$H NMR ($CDCl_3$, 300 MHz) δ: 4.49–4.40 (ddd, J=9.0 Hz, J=9.0 Hz, J=3.0 Hz, 1H), 3.95–3.68 (m, 4H), 2.23–2.12 (m, 1H), 1.99–1.87 (m, 1H), 1.46 (s, 9H).

7c. 2-((1-t-butyloxycarbonyl-2-(S)-azetidinyl)methoxy) pyrazine

To an ice cooled solution of the compound of step 7b (941 mg, 5.0 mmol) in tetrahydrofuran (30 mL) under nitrogen, was added sodium hydride (80% dispersion in mineral oil, 180 mg, 7.5 mmol), portionwise. The reaction mixture stirred fifteen minutes followed by the dropwise addition of 2-chloropyrazine (590 mg, 5.1 mmol). The reaction was stirred 24 hours gradually warming to room temperature. Additional sodium hydride (40 mg) was added and stirring at room temperature continued until complete disappearance of starting material by TLC. The reaction mixture was then treated with a 10% aqueous solution of potassium hydrogen sulfate (20 ml) and the volatiles evaporated in vacuo. The mixture was then diluted with ethyl acetate (50 ml) and the organic phase was washed with saturated sodium hydrogen carbonate (2×20 ml). The organic phase was then dried ($MgSO_4$), filtered and concentrated in vacuo. The resultant orange oil (1.37 g) was purified by flash silica gel chromatography (ethyl acetate:hexane=1:1), resulting in product isolated as an oil, in 80% yield (1.07 g). $[\alpha]^{23}_D$=−62.8° (c 1.35, $CHCl_3$). MS ($CI/NH_3$) m/e 266 $(M+H)^+$, 283 $(M+NH_4)^+$. $^1H$ NMR ($CDCl_3$, 300 MHz) δ: 8.28–8.27 (d, J=1.1 Hz, 1H), 8.13–8.12 (d, J=2.58 Hz, 1H), 8.08–8.06 (dd, J=2.58, J=1.5 Hz, 1H), 4.66–4.61 (dd, J=10.83, J=4.6, 1H), 4.58–4.51 (m, 1H), 4.50–4.45 (dd, J=10.83, J=3.13, 1H, 3.92–3.87 (dd, J=8.3, J=6.25, 2H), 2.41–2.29 (m, 1H), 2.26–2.16 (m, 1H), 1.41 (s, 9H).

7d. 2-(2-(S)-azetidinylmethoxy)pyrazine dihydrochloride

The compound of step 7c (335 mg, 1.26 mmol) was stirred in methylene chloride (2 ml) and cooled to 0° C. To this was added trifluoroacetic acid in methylene chloride (3 ml, 1:1). The reaction was stirred 18 hours, gradually warming to room temperature. The mixture was then basified (pH=9) with a saturated solution of sodium hydrogen carbonate and continuously extracted with methylene chloride for 16 hours. The extract was dried ($MgSO_4$), filtered and concentrated in vacuo. The resultant oil was not purified further, but was was dissolved in ethanol (2 mL) and immediately treated with diethyl ether saturated with hydrogen chloride gas. Crystals began to form immediately. Recrystallization from ethanol and diethyl ether yielded pure product (51.2 mg, 0.256 mmol, 80% yield) as the hydrochloride salt. mp (dec) MS ($DCI/NH_3$) m/e 166 $(M+H)^+$, 183 $(M+NH_4)^+$. $^1H$ NMR ($D_2O$, 300 MHz) δ: 8.37 (s, 1H), 8.23 (s, 2H), 4.97–4.92 (m, 1H) 4.74–4.58 (m, 2H), 4.19–4.00 (m, 2H), 2.72–2.62 (dd, J=16.8 Hz, J=8.8 Hz, 2H). Anal. calcd. for $C_8H_{11}N_3O.2.4$ HCl: C, 38.02; H, 5.34; N, 16.63. Found: C, 37.99; H, 5.37; N, 16.60.

EXAMPLE 8

2-((1-methyl-2-(S)-azetidinyl)methoxy)pyrazine dihydrochloride

The compound of Example 7a (102.9 mg, 0.62 mmol) was stirred with excess paraformaldehyde in ethanol (5 mL), on ice and under nitrogen, and the pH adjusted to five with the addition of acetic acid and sodium acetate. The reaction was stirred for 15 minutes and sodium cyanoborohydride (59 mg, 0.936 mmol) was added. A very small amount of bromocresol green was added directly to the reaction mixture as indicator. The reaction was stirred 19 hours, allowed to warm to room temperature, and additional formaldehyde (0.25 mL) and sodium cyanoborohydride (20 mg, 0.32 mmol) was added to push the reaction to completion. The reaction mixture was then acidified (pH=1) with 10% solution of potassium hydrogen sulfate and the volatiles evaporated. The aqueous phase was washed with ethyl acetate (3×10 mL), basified with sodium carbonate (pH=9.5), and products extracted with ethyl acetate (5×15 mL). These extracts were dried ($MgSO_4$), filtered, and concentrated in vacuo. The resultant oil (111.7 mg, 100% yield), was then purified by flash silica gel chromatography (chloroform:methanol:ammonium hydroxide/98:2:0.1), yielding the pure product (60.1 mg, 54% yield), which was dissolved in ethanol and converted to the hydrochloride salt in a similar manner as that of Example 7d, (62.2 mg, 86% yield). mp 161–162° C. (dec). MS ($DCI/NH_3$) m/e 180 $(M+H)^+$. $^1H$ NMR ($D_2O$, 300 MHz) δ: 8.37 (S, 1H), 8.24 (s, 2H), 4.87–4.76 (m, 1H), 4.32–4.23 (ddd, J=10 Hz, J=10 Hz, J=6 Hz, 1H), 4.04–3.95 (dd, J=19.5 Hz, J=9.6 Hz, 1H), 2.97 (s, 3H), 2.70–2.58 (m, 2H). Anal. calcd. for $C_9H_{13}N_3O.2.0$ HCl.0.3. $H_2O$: C, 41.97; H, 6.10; N, 16.32. Found: C, 42.25; H, 5.93; N, 16.02.

EXAMPLE 9

3-(2-(S)-azetidinylmethoxy)pyridine dihydrochloride 9a. 3-((1-t-butyloxycarbonyl-2-(S)-azetidinyl)methoxy) pyridine An ice cooled solution of the compound of Example 7b (2.8 g, 14.97 mmol) in tetrahydrofuran (40 mL) was stirred under a nitrogen atmosphere. To this was added DEAD (3.54 mL, 22.46 mmol) followed by triphenylphosphine (4.78 g, 22.46 mmol) and the mixture was stirred 10 minutes. 3-Hydroxypyridine (2.14 g, 22.46 mmol) was then added to the reaction with additional tetrahydrofuran (40 mL). After 18 hours, additional 3-hydroxypyridine (0.1 g, 1.05 mmol) was added and the reaction stirred 24 hours longer. When all starting azetidine alcohol was consumed, the reaction mixture was concentrated in vacua. The crude mixture was then acidified (pH<2) with a 10% solution of potassium hydrogen sulfate (80 mL), and washed with ethyl acetate (3×75 mL). The aqueous portion was then basified with a saturated solution of potassium carbonate (pH=10) and products extracted with ethyl acetate (4×75 mL). These extracts were dried ($MgSO_4$), filtered and concentrated in vacuo to a red-brown oil (1.84 g, 50% yield). The crude product was purified via flash silica gel chromatography $R_f$=0.19, (ethyl acetate:hexane=2:1), yielding product as a light yellow oil in 25% yield. MS ($DCI/NH_3$) m/e 265 $(M+H)^+$, 282 $(M+NH_4)^+$. $^1H$ NMR ($CDCl_3$) δ: 8.36–8.35 (dd, J=3.7 Hz, J=0.7 Hz, 1H), 8.24–8.22 (dd, J=4.0 Hz, J=1.5 Hz, 1H), 7.25–7.22 (m, 2H), 4.56–4.48 (m, 1H), 4.36–4.31 (dd, J=10 Hz, J=4.9 Hz, 1H), 4.17–4.12 (dd, J=10 Hz, J=2.9 Hz, 1H), 3.92–3.87 (dd, J=8.2 Hz, J=6.8 Hz, 2H), 2.42–2.25 (m, 2H), 1.42 (s, 9H).

9b. 3-(2-(S)-azetidinylmethoxy)pyridine dihydrochloride

To an ice cooled solution of the compound of step 9a (286 mg, 1.08 mmol) in absolute ethanol (4 mL), was added a hydrogen chloride saturated ethanol solution (4 mL), under nitrogen. The reaction mixture was stirred 18 hours while gradually warming to room temperature. The reaction mixture was then concentrated in vacuo, the product dissolved in absolute ethanol and triturated with diethyl ether. Two recrystallizations from ethanol and diethyl ether yielded pure product in 81% yield as a white powder (174 mg, 87 mmol). MS ($DCI/NH_3$) m/e 165 $(M+H)^+$, 182 $(M+NH4)^+$. $^1NMR$ ($D_2O$, 300 MHz) δ: 8.60–8.59 (d, J=2.9 Hz, 1H), 8.48–8.46 (d, J=5.8 Hz, 1H), 8.25–8.21 (ddd, J=9.0 Hz, J=2.6 Hz, J=1.1 Hz, 1H), 5.05–4.97 (m, 1H), 4.59–4.57 (d, J=4.0 Hz, 2H), 4.22–4.05 (m, 2H), 2.77–2.67 (dd, J=16.9 Hz, J=8.45 Hz, 2H). Anal. calcd. for $C_9H_{12}N_2O.2.7$ HCl.0.2 $H_2O$: C, 40.60; H, 5.71; N, 10.52. Found: C, 40.75; H, 5.76; N, 10.51.

EXAMPLE 10

3-((1-methyl-2-(S)-azetidinyl)methoxy)pyridine dihydrochloride

To an ice cooled solution of the compound of Example 9a (550 mg, 1.89 mmol) in methylene chloride (3 ml) under nitrogen, was added trifluoroacetic acid in methylene chloride (5 ml, 1:1). The reaction was stirred 18 hours, gradually warming to room temperature. The reaction mixture was then concentrated in vacuo, brought up in absolute ethanol (5 ml). Parformaldehyde was added, and the acidity adjusted to pH 5 with the addition of acetic acid and sodium acetate. The reaction mixture was stirred for 15 minutes and sodium cyanoborohydride (180 mg, 2.86 mmol) was added. A small amount of bromocresol green was added to the reaction mixture as indicator. The mixture stirred 18 hours after which time the reaction was complete as monitored by TLC. The reaction mixture was then acidified (pH=1) with saturated solution of potassium hydrogen sulfate, and the volatiles evaporated in vacuo. The aqueous phase was then washed with ethyl acetate (3×20 ml), basified (pH=10) with potassium carbonate, and the crude products extracted with ethyl acetate (4×20 ml). The extracts were dried (MgSO$_4$), filtered and concentrated in vacuo (274 mg, 81% yield). The crude product was then purified by flash silica gel chromatography, yielding a colorless oil (147 mg, 44% yield). This oil was dissolved in absolute ethanol (1.5 mL) and treated with hydrogen chloride saturated diethyl ether. After one recrystallization from ethanol and diethyl ether, pure product resulted in the form of fine hygroscopic needles. MS (CI/NH$_3$) m/e 179 (M+H)$^+$, 196 (M+NH$_4$)$^+$. $^1$H NMR (D$_2$O/300 MHz) δ: 8.53 (d, J=2.2Hz, 1H), 8.42–8.41 (d, J=5.5 Hz, 1H), 8.09–8.05 (dd, J=8.8 Hz, J=0.3 Hz, 1H), 7.91–7.86 (dd, J=8.8 Hz, J=5.4 Hz, 1H), 4.90–4.80 (m, 1H), 4.63–4.58 (dd, J=11.8 Hz, J=2.9 Hz, 1H), 4.56–4.50 (dd, J=11.8 Hz, J=5.3 Hz, 1H), 4.34–4.25 (ddd, J=9.9 Hz, J=9.9 Hz, J=5.1, 1H), 4.06–3.97 (dd, J=19.5 Hz, J=9.4 Hz, 1H), 3.00 (s, 3H), 2.77–2.60 (m, 2H). Anal. calc. for C$_{10}$H$_{14}$N$_2$O.2.0 HCl.0.7 H$_2$O: C, 45.54; H, 6.65; N, 10.62. Found: C, 45.38; H, 6.35; N. 10.53.

EXAMPLE 11

2-((1-methyl-2-(S)-pyrrolidinyl)methoxy)thiazole hydrochloride (S)-(−)-1-Methyl-2-pyrrolidine methanol (484 mg, 4.2 mmol) was reacted with NaH ((80% dispersion in mineral oil) 0.164 g 5.46 mmol) and 2-bromothiazole (0.417 g, 4.62 mmol) according to the procedure outlined in Example 3a to afford after column chromatography eluting with (10% MeOH/CHCl$_3$+1% NH$_3$) (616.2 mg, 3.1 mmol, 74% yield) of 2-(1-methyl-2-(S)-pyrrolidinylmethoxy)-thiazole. The pure base was then converted to its hydrochloride salt by treating the amine (109.4 mg, 0.552 mmol) with a saturated solution of HCl in Et$_2$O dropwise with stirring until no more precipitate formation was observed. This afforded 21.2 mg, 0.09 mmol, 16% of the title compound. mp=99° C. [α]$_d^{20}$=+2.86° (c=0.021, MeOH). MS (DCI/NH$_3$) m/e 199 (M+H)$^+$. $^1$H NMR (CD$_3$OD, 300 MHz) δ: 7.18 (d, J=4.04 Hz, 1H), 6.99 (d, J=4.04 Hz, 1H), 4.85 (dd, J=12.50, 3.31 Hz, 1H), 4.65 (dd, J=12.5, 6.62 Hz, 1H), 4.09–3.85 (m, 1H), 3.85–3.65 (m, 1H), 3.03 (br s, 3H), 2.45–2.3 (m, 1H), 2.3–1.95 (m, 3H). Analysis calculated for C$_9$H$_{15}$N$_2$OSCl.0.6 H$_2$O0.1Et$_2$O: C, 44.63; H, 6.85; N, 11.07; Found: C, 44.68; H, 6.46; N, 10.68.

EXAMPLE 12

3-((1-methyl-2-(S)-pyrrolidinyl)methoxy-6-chloropyridazine fumarate 12a. 3-((1-methyl-2-(S)-pyrrolidinyl)methoxy)-6-chloropyridazine (S)-(−)-1-Methyl-2-pyrrolidinemethanol (968 mg, 8.4 mmol) was reacted in a similar fashion as that described for the (R)-isomer of Example 5a to afford 1.31 g (69% yield) of the title compound. [α]$_D^{25}$=−28.3° (c=1.1, MeOH).

12b. 3-((1-methyl-2-(S)-pyrrolidinyl)methoxy)chloropyridazine fumarate

The compound of step 12a (37.3 mg, 0.16 mmol) was reacted with 19 mg of fumaric acid in a process similar to that described in Example 4b to afford 39 mg (70% yield) of the title compound as a white solid, m.p.=155° C. [α]$_D^{20}$=+4.8° (c=1.0, MeOH). MS (DCI/NH$_3$) m/e 228 (M+H)$^+$. $^1$H NMR (D$_2$O, 300 MHz) δ: 7.6 (d, J=9.19 Hz, 1H), 7.37 (d, J=9.19 Hz, 1H), 6.64 (s, 2H), 4.82 (dd, J=12.14, 3.1 Hz, 1H), 4.66 (dd, J=12.13, 5.88 Hz, 1H), 4.0–3.92 (m, 1H), 3.8–3.72 (m, 1H), 3.3–3.21 (m, 1H), 3.04 (s, 3H), 2.46–2.36 (m, 1H), 2.27–2.02 (m,3H). Analysis calculated for C$_{14}$H$_{18}$N$_3$O$_5$Cl: C, 48.91; H, 5.27; N, 12.22; Found: C, 48.86; H. 4.87; N, 11.98.

EXAMPLE 13

6-chloro-3-((1-methyl-2(S)-azetidinyl)methoxy) pyridazine oxalate 13a. 3-((1-BOC-2(S)-azetidinyl)methoxy)chloro-pyridazine The compound from Example 7b (3.18 g, 17.0 mmol), sodium hydride (80% dispersion in mineral oil, 510 mg, 17.0 mmol), and 3,6-dichloropyridazine (3.8 g, 25.5 mmol) were combined in a similar manner as that described in Example 7c. The crude product was purified by flash chromatography on silica gel using EtOAc/hexane (1:6 to 1:4) as the elutant to give 3.87 g of a viscous oil, which solidified in the refrigerator (76% yield). TLC R$_f$=0.58 (EtOAc/hexane 1:1). mp.=50–54° C. MS (CI) m/e 300 (M+H)$^+$. $^1$H NMR (DMSO-d$_6$, 300 MHz) δ: 7.73 (d, J=9.2 Hz, 1H), 7.31 (d, J=9.2 Hz, 1H), 4.72 (dd, J=11.0 Hz, 4.6 Hz, 1H), 4.59 (dd, J=11.0 Hz, 3.7 Hz, 1H), 4.56–4.50 (m, 1H), 3.79 (t, J=7.6 Hz, 2H), 2.40–2.38 (m, 1H), 2.20–2.09 (m, 1H), 1.36 (s, 9H).

13b. 6-chloro-3-((1-methyl-2(S)-azetidinyl)methoxy) pyridazine

The compound from step 13a (805 mg, 2.68 mmol) was treated in a similar fashion as that described under Example 7d. The crude was subject to flash chromatography on silica gel with 10% MeOH in CHCl$_3$ to 0.5% NH$_4$OH in 10% MeOH in CHCl$_3$ used as the elutant to give 352 mg of a yellow oil (66% yield). MS (CI) m/e 200 (M+H)$^+$. The amine deprotected material (330 mg, 1.66 mmol) was then subjected to reductive amination conditions previously described in Example 8. The crude product was purified by flash chromatography on silica gel using 2% MeOH in CHCl$_3$ to 5% MeOH in CHCl$_3$ as the elutant to give 125 mg of a clear oil (35% yield). MS (CI) m/e 214 (M+H)$^+$. $^1$H NMR (CDCl$_3$, 300 MHz) δ: 7.36 (d, J=9.2 Hz, 1H), 7.02 (d, J=9.2 Hz, 1H, 4.54 (dd, J=11.6 Hz, 3.8 Hz, 1H), 4.47 (dd, J=11.6 Hz, 5.7 Hz, 1H, 3.48–3.39 (m, 2H), 2.89–2.81 (m, 1H), 2.38 (s, 3H), 2.17–2.03 (m, 2H).

13c. 6-chloro-3-((1-methyl-2(S)-azetidinyl)methoxy) pyridazine oxalate

The compound of step 13b (120 mg, 0.56 mmol) was dissolved in 8 mL of diethyl ether and cooled to 0° C. Oxalic acid (55.5 mg, 0.62 mmol) in 1 mL of diethyl ether was added dropwise to the reaction vessel, and the reaction was stirred for 30 minutes. The solvent was then removed in vacuo and the remaining white solid recrystallized out of hot methanol to give 128 mg of the title compound (75% yield). mp=165–167° C. [α]$_D^{23}$=−26.7° (c 0.75, H$_2$O). MS (CI) m/e 214 (M+H)$^+$. $^1$H NMR (D$_2$O, 300 MHz) δ: 7.78 (d, J=9.2 Hz, 1H, 7.40 (d, J=9.2 Hz, 1H, 4.89–4.73 (m, 3H), 4.32–4.22 (m, 1H), 4.05–3.94 (m, 1H), 2.97 (s, 3H), 2.73–2.60 (m, 2H). Anal Calc for C$_{11}$H$_{14}$ClN$_3$O$_5$: C, 43.50; H, 4.65; N, 13.84. Found: C, 43.59; H, 4.50; N, 13.65.

EXAMPLE 14

3-(2-(S)-pyrrolidinylmethoxy)pyridine fumarate 14a. 3-((1-t-butoxycarbonyl-2-(S)-pyrrolidinyl)methoxy)pyridine To a solution of triphenylphosphine (1.97 g, 7.5 mmol) in 30 mL of tetrahydrofuran at room temperature was added diethyl azodicarboxylate (DEAD) (1.13 mL, 7.5 mmol) dropwise with stirring. After stirring at room temperature for 30 minutes, (S)-1-t-butoxycarbonyl-2-pyrrolidinemethanol (from Example 15a below, 1 g, 5.0 mmol) and 3-hydroxypyridine (713 mg, 7.5 mmol) were added to the reaction mixture. The resultant solution was stirred at room temperature for 16 hr. After all the starting material was consumed, the organic solvent was evaporated in vacuo. The residue was purified by silica gel column chromatography. Elution with chloroform:methanol (10:1) provided 2 g of the title compound. MS (DCI/NH3) m/e 279 (M+H)$^+$.

14b. 3-(2-(S)-pyrrolidinylmethoxy)pyridine

To a solution of the compound of step 14a in 12 mL of methylene chloride solution was added 12 mL of trifluoroacetic acid. The resultant solution was stirred at room temperature for 3 hr. Evaporation of both solvent and trifluoroacetic acid gave a brown oil which was basified with saturated ammonium hydroxide solution. This oil was purified by silica gel column chromatography. Elution with a mixture of chloroform:methanol: ammonium hydroxide (10:1:0.1) provided the desired product. MS (DCI/NH$_3$) m/e 179 (M+H)$^+$. $^1$H NMR (D$_2$O, 300 MHz) δ: 8.33 (br s, 1H, 8.22 (m, 1H), 7.22(m, 2H), 3.82–4.03 (m, 2H), 3.50–3.61 (m, 1H), 2.92–3.10 (m, 2H), 1.70–2.10 (m, 4H), 1.51–1.66 (m, 1H).

14c. 3-(2-(R)-pyrrolidinylmethoxy)pyridine fumarate

The compound of step 14b (281 mg, 1.57 mmol) was dissolved in anhydrous MeOH and brought to 0° C. with stirring. Fumaric acid was dissolved in MeOH with sonication and added dropwise to the base. The mixture was warmed to room temperature with stirring. After 30 minutes the solvent was evaporated in vacuo, and the remaining solid was triturated with anhydrous diethyl ether. The product was obtained as a hygroscopic solid in 47% yield (218 mg). MS (DCI/NH$_3$) m/e: 179 (M+H)$^+$. $^1$H NMR (D$_2$O, 300 MHz) δ: 8.38 (m, 1H), 8.30 (m 1H), 7.76–7.72 (m, 1H), 7.72–7.62 (m, 1H), 6.57 (s, 2H), 4.60–4.50 (m, 1H), 4.35–4.25 (m, 1H), 4.10–4.08 (m, 1H), 3.42 (t, J=7.5 Hz, 2H), 2.37–2.23 (m, 1H), 2.23–2.06 (m, 2H), 2.06–1.98 (m, 1H). Anal calc. for C$_{10}$H$_{14}$N$_2$O.C$_2$H$_4$O$_2$.0.9 H$_2$O: C, 54.15; H, 6.2; N, 9.02; Found: C, 54.48; H, 6.02; N, 8.67.

EXAMPLE 15

5-chloro-3-(2-(S)-pyrrolidinylmethoxy)pyridine dihydrochloride 15a. (S)-1-t-Butoxycarbonyl-2-pyrrolidinemethanol N-t-BOC-proline (Sigma Chemical Co., 12.97 g, 60.02 mmol) was dissolved in anhydrous THF and brought to 0° C. with stirring. Borane/THF complex was added dropwise via syringe over a 10 minute period. The reaction mixture was stirred at room temperature for 1 hour, then the reaction was quenched slowly with saturated NaHCO$_3$ and stirred for an additional hour. The solvent was removed in vacuo, and the residue was diluted with H$_2$O. The desired compound was extracted from the aqueous phase with Et$_2$O (3x). The organic layer was then washed with brine (2x) dried (MgSO$_4$) and evaporated. The resulting material was carried on without further purification.

15b. 5-chloro-3-((1-t-butoxycarbonyl-2-(S)-pyrrolidinyl)methoxy)pyridine (S)-1-t-Butoxycarbonyl-2-pyrrolidinemethanol (1.75 g, 8.71 mmol, prepared as in Example 15a) and 5-chloro-3-pyridinol (1.69 g, 13.10 mmol, Aldrich Chemical Co.). were allowed to react in the presence of triphenylphosphine and DEAD as described in Example 2a. The crude product was purified by chromatography over silica gel eluted with hexane/EtOAc to provide 1.49 g (60%) of the title compound as a pale yellow oil. TLC R$_f$ 0.75 (1:1 EtOAc/Hex). MS (DCI/NH$_3$) m/e 313 (M+H)$^+$ with $^{35}$Cl and m/e 315 (M+H)$_+$ with $^{37}$Cl.

15c. 5-chloro-3-(2-(S)-pyrrolidinylmethoxy)pyridine

The compound of step 15b (0.440 g, 1.41 mmol) was treated with trifluoroacetic acid in CH$_2$Cl$_2$ as described in Example 2b, then saturated K$_2$CO$_3$ was added and the aqueous phase was extracted with CH$_2$Cl$_2$ (3x). The organic layer was dried (MgSO$_4$) and evaporated, and the crude product was purified by chromatography over silica gel eluted with CHCl$_3$/MeOH/NH$_4$OH/to give 0.299 g (100%) of the title compound as a pale yellow oil. MS (DCI/NH$_3$) m/e: 213 (M+H)$^+$ with $^{35}$Cl and 215 (M+H)$^+$ with $^{37}$Cl. $^1$H NMR (CDCl$_3$, 300 MHz) δ: 8.22 (d, J=2.6 Hz, 2H), 8.19 (d, J=2.2 Hz, 1H), 7.22 (t, J=2.50 Hz, 1H), 3.97 (dd, J=9, 5 Hz, 1H), 3.90 (dd, J=9, 7 Hz, 1H), 3.60–3.51 (m, 1H), 3.08–2.95 (m, 2H), 2.32 (br s, 1H), 2.03–1.74 (m, 3H), 1.62–1.51 (m, 1H). [α]$_D$$^{25}$=+13.94° (c=1.04, MeOH).

15d. 5-chloro-3-(2-(S)-pyrrolidinylmethoxy)pyridine dihydrochloride

The compound of step 15c was treated with HCl and isolated as described in Example 1b to afford a cream colored powder. mp 183–186° C. MS (DCI/NH$_3$) m/e: 213 (M+H)$^+$ with $^{35}$Cl and 215 (M+H)$^+$ with $^{37}$Cl. $^1$H NMR (D$_2$O, 300 MHz) δ: 8.23 (m, 2H), 7.60 (t, J=2.20 Hz, 1H), 4.47 (dd, J=10.60, 3.70 Hz, 1H), 4.25 (dd, J=10.60, 8 Hz, 1H), 4.14–4.10 (m, 1H), 3.44–3.39 (t, J=7 Hz, 2H), 2.32–2.23 (m, 1H), 2.19–2.07 (m, 2H), 2.01–1.92 (m, 1H). Anal. Calc. for C$_{10}$H$_{13}$N$_2$OCl.2.00 HCl: C, 42.06; H, 5.29; N, 9.81; Found C, 42.47; H, 5.34; N, 9.90. [α]$_D$$^{25}$=+10.10° (c=1, MeOH).

EXAMPLE 16

5-chloro-3-((1-methyl-2-(S)-pyrrolidinyl)methoxy)pyridine dihydrochloride 16a. 5-chloro-3-((1-methyl-2-(S)-pyrrolidinyl)methoxy)pyridine To 5-chloro-3-((1-t-butoxycarbonyl-2-(S)-pyrrolidinyl)methoxy)pyridine (0.600 g, 1.92 mmol), from Example 15b, was added a solution of formic acid/formaldehyde (1:2, 3 mL). The mixture was heated at reflux for 3 hours, then basified with sat. K$_2$CO$_3$. The aqueous phase was extracted with CH$_2$Cl$_2$ (3x) then the organic layer was dried (MgSO$_4$) and concentrated. The crude product was purified by chromatography over silica gel eluted with CHCl3/MeOH to afford 0.274 g (63%) of the title compound as a pale yellow oil. TLC R$_f$=0.23 (10%MeOH/CHCl$_3$). MS (DCI/NH$_3$) m/e: 227 (M+H)$^+$ with $^{35}$Cl and 229 (M+H)$^+$ with $^{37}$Cl. $^1$H NMR (CDCl$_3$, 300 MHz) δ: 8.22 (d, J=2.6 Hz, 1H), 8.19 (d, J=2.2 Hz, 1H), 7.22 (t, J=2 Hz, 1H), 4.00 (dd, J=9, 5.50 Hz, 1H), 3.92 (dd, J=9, 5.20 Hz, 1H), 3.14–3.08 (m, 1H), 2.69–2.64 (m, 1H), 2.47 (s, 3H), 2.36–2.27 (m, 1H), 2.07–1.97 (m, 1H), 1.88–1.69 (m, 3H).

16b. 5-chloro-3-(1-methyl-(S)-pyrrolidinylmethoxpy)pridine dihydrochloride

The compound of step 16a was treated with HCl and isolated as described in Example 1b to give a white powder. mp=200° C. (dec). MS (DCI/NH$_3$) m/e: 227 (M+H)$^+$ with $^{35}$Cl and 229 (M+H)$^+$ with $^{37}$Cl. $^1$H NMR (D$_2$O, 300 Hz) δ: 8.25–8.24 (m, 2H), 7.63–7.61 (m, 1H), 7.62 (t, J=2.3 Hz), 4.53 (dd, J=11, 3 Hz, 1H, 4.36 (dd, J=9, 6 Hz, 1H), 3.94 (m, 1H), 3.76 (m, 1H), 3.17–3.10 (m, 1H), 3.04 (s, 3H), 2.44–2.35 (m, 1H), 2.25–2.02 (m, 3H). Anal. Calc. for $C_{11}H_{15}N_2OCl.2.00$ HCl: C, 44.10; H, 5.72; N, 9.35; Found C, 44.07; H, 5.69; N, 9.35. $[\alpha]_D^{25}=-5.60°$ (c=1, MeOH).

EXAMPLE 17

2-methyl-3-(2-(S)-pyrrolidinylmethoxy)pyridine dihydrochloride 17a. 2-methyl-3-((1-t-butoxycarbonyl-2-(S)-pyrrolidinyl)methoxy)pyridine To a solution of triphenylphosphine (3.83 g, 14.6 mmol) in 40 mL of anhydrous THF at 0° C. was added diethyl azodicarboxylate (2.30 mL, 14.6 mmol) dropwise. The mixture was stirred at 0° C. for 30 minutes, then brought to room temperature. (S)-1-t-Butoxycarbonyl-2-pyrrolidinemethanol (1.96 g, 9.75 mmol, Aldrich Chemical Co.) and 2-methyl-3-hydroxypyridine (Aldrich Chemical Co., 1.60 g, 14.6 mmol) were added to the reaction vessel, and the mixture was stirred for 16 hours. Solvent was removed in vacuo, and the residue was diluted with hexane and sonicated for 30 minutes. The resulting precipitate was filtered and washed with hexane. The hexane was removed in vacuo. The residue was purified by silica gel flash chromatography (ethyl acetate) to give 1.42 g (50% yield) of the title compound as a pale yellow oil. TLC $R_f$=0.50 (EtOAc). MS (DCI/NH$_3$) m/e: 293 (M+H)$^+$.

17b. 2-methyl-3-(2-(S)-pyrrolidinylmethoxy)pyridine

To a solution of the compound of step 17a (0.407 g, 1.39 mmol) in 2 mL of methylene chloride at 0° C. was added 2 mL of trifluoroacetic acid. The reaction was stirred at this temperature for 40 minutes. The temperature was raised to room temperature, and the reaction was stirred for an additional 30 minutes. Once the starting material was consumed, saturated K$_2$CO$_3$ was added and the product was extracted from the aqueous phase with CH$_2$Cl$_2$ (3×). The organic layer was then dried over MgSO$_4$. The resulting crude material was purified by silica gel flash chromatography using a gradient from 100% CHCl$_3$ to 10% MeOH/CHCl$_3$ and finally 1%NH$_4$OH/10%MeOH/CHCl$_3$ to give 0.236 g (88%) of the title compound as a pale yellow oil. MS (DCI/NH$_3$) m/e: 193 (M+H)$^+$. $^1$H NMR (CDCl$_3$, 300 MHz) δ: 8.07 (t, J=3 Hz, 1H), 7.07 (m, 2H), 3.95–3.85 (m, 2H), 3.60–3.55 (m, 1H), 3.10–2.97 (m, 2H), 2.48 (s, 3H), 2.23 (br s, 1H), 2.04–1.93 (m, 1H), 1.90–1.78 (m, 2H), 1.67–1.58 (m, 1H).

17c. 2-methyl-3-(2-(S)-pyrrolidinylmethoxy)pyridine dihydrochloride

The free base from step 17b was dissolved in diethyl ether and brought to 0° C. with stirring. The solution was treated with diethyl ether saturated with hydrogen chloride gas. The solvent was removed in vacuo. The resulting salt was triturated with diethyl ether (2×) and dried under vacuum to give a beige powder. mp.>240° C., and decomposition occurs at 250° C. and higher. MS (DCI/NH$_3$) m/e: 193 (M+H)$^+$. $^1$H NMR (D$_2$O,300 MHz) δ: 8.17 (d, J=5.5 Hz, 1H), 7.86 (d, J=7.5 Hz, 1H), 7.67 (dd, J=8.50, 5.50 Hz, 1H), 4.58 (dd, J=11, 3 Hz,1H, 4.34 (dd, J=11, 8 Hz, 1H), 4.25–4.19 (m, 1H), 3.46–3.42 (m, 2H), 2.62 (s, 3H), 2.36–2.28 (m, 1H), 2.22–196 (m, 3H). Anal. Calc. for $C_{11}H_{16}N_2O.2.00$ HCl: C, 48.82; H, 6.84; N, 10.56; Found C, 49.60; H, 6.88; N, 10.44. $[\alpha]_D^{25}=+21.40°$ (c=1, MeOH).

EXAMPLE 18

6-methyl-3-(2-(S)-pyrrolidinylmethoxy)pyridine dihydrochloride 18a. 6-methyl-3-((1-t-butoxycarbonyl-2-(S)-pyrrolidinyl)methoxy)pyridine To a solution of triphenylphosphine (3.83 g, 14.60 mmol) in 40 mL of anhydrous THF at 0° C. was added diethyl azodicarboxylate (2.3 mL, 14.60 mmol) dropwise. The mixture was stirred at 0° C. for 30 minutes, then brought to room temperature. (S)-1-t-Butoxycarbonyl-2-pyrrolidinemethanol (1.96 g, 9.75 mmol, Aldrich Chemical Co.) and 6-methyl-3-pyridinol (Aldrich Chemical Co., 1.60 g, 14.60 mmol) were added to the reaction vessel, and the mixture was stirred for 16 hours. Solvent was removed in vacuo, and the residue was diluted with hexane and sonicated for 30 minutes. The resulting precipitate was filtered and washed with hexane. The hexane was removed in vacuo. The residue was purified by silica gel flash chromatography using a gradient from 100% hexane to a 1:1 solution of ethyl acetatelh exane (100%Hex, 10% EtOAc/Hex, 20%EtOAc/Hex, 1:1EtOAc/Hex) to give 1.61 g (57% ) of the title compound as a pale yellow oil. TLC Rf=0.42 (1:1 EtOAc/Hex). MS (DCI/NH3) m/e: 293 (M+H)$^+$.

18b. 6-methyl-3-(2-(S)-pyrrolidinylmethoxy)pyridine

To a solution of the compound of step 18a above (0.320 g, 1.09 mmol) in 2 mL of methylene chloride at 0° C. was added 2 mL of trifluoroacetic acid. The reaction was stirred at this temperature for 30 minutes. The temperature was raised to room temperature, and the reaction was stirred for an additional 30 minutes. Once the starting material was consumed, saturated K$_2$CO$_3$ was added, and the product was extracted from the aqueous phase with CH$_2$Cl$_2$ (3×). The organic layer was then dried over MgSO$_4$. The resulting crude material was purified by silica gel flash chromatography using a gradient from 100% CHCl$_3$ to 10% MeOH/CHCl$_3$ and finally 1% NH4OH/10%MeOH/CHCl$_3$ to give 0.200 g (95%) of the title compound as a pale yellow oil. MS (DCI/NH$_3$) m/e: 193 (M+H)$^+$. $^1$H NMR (CDCl$_3$, 300 Mz) δ: 8.20 (d, J=3 Hz, 1H), 7.12 (dd, J=8.50, 3 Hz, 1H), 7.05 (d, J=8.50 Hz, 1H), 3.94 (dd, J=9, 5 Hz, 1H), 3.87 (dd, J=9, 7 Hz, 1H, 3.57–3.48 (m, 1H), 3.07–2.92 (m, 2H), 2.48 (s, 3H), 2.18 (br s, 1H), 2.01–1.89 (m, 1H), 1.88–1.71 (m, 2H), 1.62–1.51 (m, 1H). $[\alpha]_D^{25}=+11.40°$ (c=1, MeOH).

18c. 6-methyl-3-(2-(S)-pyrrolidinylmethoxy)pyridine dihydrochloride

The free base from step 18b was dissolved in diethyl ether and brought to 0° C. with stirring. The solution was treated with diethyl ether saturated with hydrogen chloride gas. The solvent was removed in vacuo. The resulting salt was triturated with diethyl ether (2×) and dried under vacuum to give a beige powder. mp.>100° C. (dec). MS (DCI/NH$_3$) m/e: 193 (M+H)$^+$. $^1$H NMR (D$_2$O, 300 MHz) δ: 8.27 (d, J=3 Hz, 1H), 7.81 (dd, J=9, 3 Hz, 1H), 7.59 (d, J=9 Hz, 1H), 4.51 (dd, 10.50, 3.50 Hz, 1H), 4.31 (dd, 10.50, 7.50 Hz, 1H), 4.19–4.12 (m, 1H), 3.43 (d, J=7 Hz, 2H), 2.60 (s, 3H), 2.33–2.24 (m, 1H), 2.20–1.92 (m, 3H). Anal. Calc. for $C_{11}H_{16}N_2O.2.00.HCl$: C, 49.82; H, 6.84; N, 10.56; Found C, 49.78; H, 6.53; N, 10.26. $[\alpha]_D^{25}=+10.00°$ (c=1, MeOH).

EXAMPLE 19

6-methyl-3-((1-methyl-2-(S)-pyrrolidinyl)methoxy) pyridine dihydrochloride 19a. 6-methyl-3-((1-methyl-2-(S)-pyrrolidinyl)methoxy) pyridine To 3 mL of a solution of formic acid/formaldehyde (1:2) was added the compound from Example 19a (0.600 g, 2.05 mmol). The mixture was brought to a gentle reflux and stirred at this temperature (80° C.) for 3 hours. The reaction was basified with sat. $K_2CO_3$. The desired compound was extracted from the aqueous phase with $CH_2Cl_2$ (3×). The organic layer was dried over $MgSO_4$ The resulting crude material was purified by silica gel flash chromatography using a gradient from 100% chloroform to 10% methanol/chloroform (5% increments) to give 0.403 g (95%) of the title compound as a clear colorless oil. TLC Rf=0.17 (10% MeOH/CHCl3). MS (DCI/NH3) m/e 207 (M+H)$^+$. $^1$H NMR (CDCl$_3$, 300 MHz) δ: 8.21 (d, J=3 Hz, 1H), 7.13 (dd, J=8.50, 3 Hz, 1H), 7.05 (d, J=8.50 Hz, 1H), 4.06 (dd, J=9, 5.50 Hz, 1H), 3.93 (dd, J=9, 5.50 Hz, 1H), 3.19–3.14 (m, 1H), 2.74–2.69 (m, 1H), 2.52 (s, 3H), 2.48 (s, 3H), 237–2.31 (m, 1H), 2.08–1.99 (m, 1H), 1.89–1.74 (m, 3H).

19b. 6-methyl-3-((1-methyl-2-(S)-pyrrolidinyl)methoxy)pyridine dihydrochloride

The free base from step 19a was dissolved in diethyl ether and brought to 0° C. with stirring. This solution was treated with diethyl ether saturated with hydrogen chloride gas. The solvent was removed in vacuo. The resulting salt was triturated with diethyl ether (2×) and dried under vacuum to give a white powder. m.p.=213–216° C. MS (DCI/NH$_3$) m/e: 207 (M+H)$^+$. $^1$H NMR (D$_2$O, 300 MHz) δ: 8.28 (d, J=3 Hz, 1H), 7.79 (dd, J=9, 3 Hz, 1H), 7.58 (d, J=9 Hz, 1H), 4.56 (dd, J=11, 3 Hz, 1H), 4.39 (dd, J=11, 6 Hz, 1H), 3.95 (br s, 1H), 3.77 (br s, 1H), 3.28 (br s, 1H), 3.04 (s, 3H), 2.59 (s, 3H), 2.42–2.37 (m, 1H), 2.25–2.08 (m, 3H). Anal. Calc. for $C_{12}H_{18}N_2O.2.00$ HCl: C, 51.62; H, 7.22; N, 10.03; Found C, 51.49; H, 7.36; N, 9.96. $[\alpha]_D^{25}$=–6.40° (c=1, MeOH).

EXAMPLE 20

4-bromo-3-(2-(S)-pyrrolidinylmethoxy)pyridine dihydrochloride 20a. 3-pyridyl diethylcarbamate To a refluxing solution of 3-pyridinol (9.7 g, 0.10 mol) and triethylamine (17.0 mL, 0.12 mol) in anhydrous benzene (300 mL) was slowly added a solution of N,N-dimethylcarbamyl chloride (14.4 mL, 0.11 mol) in anhydrous benzene (50 mL). After heating at reflux for 12 hours, the resultant mixture was filtered, and the salt was washed with benzene (3×10 mL). The filtrate was concentrated and distilled under reduced pressure to provide 18.4 g (95% yield) of the title compound as a light yellow oil (lit.: bp 91–93° C./3.5 mmHg, Millner, O. E, Jr.; Stanley, J. W; Purcell, W. P. *J. Med. Chem.* 1974, 17, 13). TLC R$_f$ 0.57 (10:1 CHCl$_3$/MeOH). MS (DCI/NH$_3$) m/e 212 (M+NH$_4$)$^+$, 195 (M+H)$^+$. $^1$H NMR (CDCl$_3$, 300 MHz) δ: 8.44 (d, J=0.9 Hz, 1H, ArH), 8.43 (dd, J=4.8, 1.8 Hz, 1H, ArH), 7.53 (ddd, J=7.5, 1.8, 0.9 Hz, 1H, ArH), 7.30 (dd, J=7.5, 4.8 Hz, 1H, ArH), 3.43 (q, J=7.2 Hz, 2H, NCH$_2$), 3.40 (q, J=7.2 Hz, 2H, NCH$_2$), 1.27 (t, J=7.2 Hz, 3H, CH$_3$), 1.21 (t, J=7.2 Hz, 3H, CH$_3$).

20b. 4-bromo-3-pyridyl diethylcarbamate

To a cooled (–78° C.) solution of TMEDA (787 mg, 6.6 mmol) in anhydrous THF (15 mL) was slowly added sec-butyl lithium (1.30 M, 5.08 mL, 6.6 mmol), and the resultant solution was stirred at –78° C. for 10 minutes. 3-Pyridyl diethylcarbamate (1.16 g, 6.0 mmol, from step 20a) in THF (3 mL) was slowly added, and the mixture was stirred at –78° C. for 30 minutes. 1,2-Dibromoethane (0.575 mL, 6.6 mmol) was then added, and the mixture was stirred for an additional 2 hours. Brine (1 mL) was added and the mixture was slowly warmed up to room temperature. The organic layer was decanted, and the residue was washed with ethyl acetate (3×5 mL). The combined organic layers were dried (Na$_2$SO$_4$) and concentrated under reduced pressure. The crude product was purified by flash chromatography on silica gel eluting with hexane/EtOAc (1:1 and 1:2) to provide 1.25 g (76% yield) of the title compound. TLC R$_f$ 0.48 (1:2 hexane/EtOAc). MS (DCI/NH$_3$) m/e 290 with $^{79}$Br and 292 (M+NH$_4$)$^+$ with $^{81}$Br, 273 with $^{79}$Br and 275 (M+H)$^+$ with $^{81}$Br. $^1$H NMR (CDCl$_3$, 300 MHz) δ: 8.47 (s, 1H, ArH), 8.27 (d, J=7.2 Hz, 1H, ArH), 7.16 (d, J=7.2 Hz, 1H, ArH), 3.52 (q, J=7.5 Hz, 2H, NCH$_2$), 3.41 (q, J=7.5 Hz, 2H, NCH$_2$), 1.33 (t, J=7.5 Hz, 3H, CH$_3$), 1.24 (t, J=7.5 Hz, 3H, CH$_3$).

20c. 4bromo-3-pyridinol

To a solution of 4-bromo-3-pyridyl diethylcarbamate (1.24 g, 4.50 mmol) in methanol (10 mL) was added sodium methoxide in methanol (2.04 g, 9.40 mmol), and the resultant mixture was refluxed for 1.5 hours. After removal of MeOH, EtOAc (15 mL) and water (1 mL) were added, the pH was then adjusted to 9 using 20% H$_2$SO$_4$. The organic layer was decanted, and the residue washed with EtOAc (3×5 mL). The combined organic layers were dried (Na$_2$SO$_4$) and concentrated. The crude product was purified by flash chromatography on silica gel eluting with hexane/EtOAc (1:1 and 1:2) to provide 691 mg (89% yield) of the title compound. TLC R$_f$ 0.38 (1:2 hexane/EtOAc). MS (DCI/NH$_3$) m/e 174 with $^{79}$Br and 176 (M+H)$^+$ with $^{81}$Br. $^1$H NMR (CDCl$_3$, 300 MHz) δ: 8.43 (d, J=1.5Hz, 1H, ArH), 8.02 (d, J=7.2 Hz, 1H, ArH), 7.54 (dd, J=7.2, 1.5 Hz, 1H, ArH).

20d. 4-bromo-3-(2-(S)-pyrrolidinylmethoxy)pyridine (S)-1-t-Butoxycarbonyl-2-pyrrolidinemethanol (792 mg, 3.94 mmol), 4-bromo-3-pyridinol (685 mg, 3.94 mmol), DEAD (485 uL, 4.33 mmol) and PPh3 (1.14 g, 4.33 mmol) were allowed to react as described in Example 2a. The crude product was directly treated with trifluoroacetic acid (5 mL) at room temperature for 3 hours. The trifluoroacetic acid was removed under reduced pressure, and water (8 mL) was added. The mixture was extracted with EtOAc (2×20 mL), and the resultant aqueous layer was basified with excess solid sodium bicarbonate. The resultant slurry was washed extensively with EtOAc (4×10 mL). The combined organic layers were dried (Na$_2$SO$_4$) and evaporated. The crude product was purified by flash chromatography on silica gel eluting with CHCl$_3$/MeOH/NH$_4$OH (10:1.5:0.02 and 10:1.5:0.1) to provide 371 mg (37% yield from 4-bromo-3-pyridinol) of the title compound. TLC R$_f$ 0.16 (10:1:0.02 CHCl$_3$/MeOH/NH$_4$OH). MS (DCI/NH$_3$) m/e 257 with $^{79}$Br and 259 (M+H)$^+$ with $^{81}$Br. $^1$H NMR (CDCl$_3$, 300 MHz) δ: 8.25 (s, 1H, ArH), 8.08 (d, J=6.6 Hz, 1H, ArH), 7.48 (d, J=6.6 Hz, 1H, ArH), 4.28 (dd, J=4.8, 10.2 Hz, 1H, OCHH), 4.17 (dd, J=6.3, 10.2 Hz, 1H, OCHH), 3.90–3.80 (m, 1H, NCH), 3.30–3.14 (m, 2H, NCH$_2$), 2.18–1.80 (m, 4H, 2CH$_2$).

20e. 4-bromo-3-(2-(S)-pyrrolidinylmethoxy)pyridine dihydrochloride

The compound of step 20d (140 mg) was treated with HCl and isolated as described in Example 1b to afford 120 mg (67% yield) of the title compound as a light yellow powder. mp 191–193° C. MS (DCI/NH$_3$) m/e 257 with $^{79}$Br and 259 (M+H)$^+$ with $^{81}$Br. $^1$H NMR (D$_2$O, 300 MHz) δ: 8.28 (s, 1H, ArH), 8.09 (d, J=5.2 Hz, 1H, ArH), 7.77 (d, J=5.2 Hz, 1H, ArH), 4.61 (dd, J=3.3, 10.7 Hz, 1H, OCHH), 4.36 (dd, J=7.4, 10.7 Hz, 1H, OCHH), 4.24–4.16 (m, 1H, NCH), 3.52–3.37 (m, 2H, NCH$_2$), 2.38–1.98 (m, 4H, 2CH$_2$). Anal. Calc. for $C_{10}H_{15}SN_2OCl_2Br$: C, 36.39; H, 4.58; N, 8.49. Found: C, 36.00; H, 4.24; N, 8.38.

EXAMPLE 21

4-bromo-3-((1-methyl-2-(S)-pyrrolidinyl)methoxy) pyridine dihydrochloride 21a. 4-bromo-3-((1-methyl-2-(S)-pyrrolidinyl)methoxy) pyridine (74)

The compound of Example 20d above (225 mg) was treated with formic acid and formaldehyde and isolated as described in Example 16a to afford 40 mg (18% yield) of the title compound. TLC $R_f$ 0.37 (10:1CHCl$_3$/MeOH). MS (DCI/NH$_3$) m/e 271 with $^{79}$Br and 273 (M+H)$^+$ with $^{81}$Br. $^1$H NMR (CDCl$_3$, 300 MHz) δ: 8.24 (s, 1H, ArH), 8.07 (d, J=6.3 Hz, 1H, ArH), 7.48 (d, J=6.3 Hz, 1H, ArH), 4.34–4.03 (m, 3H), 3.35–2.80 (m, 2H), 2.14 (s, 3H, CH$_3$), 2.35–1.70 (m, 4H, 2CH$_2$).

21b. 4-bromo-3-(1-methyl-2-(S)-pyrrolidinylmethoxy) pyridine dihdrochloride

The compound of step 21a (35 mg) was treated with HCl and isolated as described in Example 1b to afford 43 mg (96% yield) of the title compound as a light yellow powder. mp 191–193° C. MS (DCI/NH$_3$) m/e 271 with $^{79}$Br and 273 (M+H)$^+$ with $^{81}$Br. $^1$H NMR (D$_3$O, 300 MHz) δ: 8.32 (s, 1H, ArH), 8.14 (d, J=5.3 Hz, 1H, ArH), 7.87 (d, J=5.3 Hz, 1H, ArH), 4.69 (dd, J=3.3, 11.4 Hz, 1H, OCHH), 4.42 (dd, J=7.0, 11.4 Hz, 1H, OCHH), 4.08–3.98 (m, 1H, NCH), 3.83–3.76 (m, 1H, NCH), 3.32–3.22 (m, 1H, NCH), 3.14 (s, 3H, NCH$_3$), 2.44–2.02 (m, 4H, 2CH$_2$). Anal. Calc. for C$_{11}$H$_{17}$N$_2$OCl$_2$Br.0.10 Et$_2$O: C, 38.96; H, 5.16; N, 7.93. Found: C, 39.22; H, 4.94; N, 8.28.

EXAMPLE 22

3-((cis-1,5-dimethyl-2-(S)-pyrrolidinyl)methoxy) pyridine dihydrochloride 22a. 3-((5-oxo-2-(S)-pyrrolidinyl)methoxy)pyridine To a solution of triphenylphosphine (52.46 g, 0.20 mol) in 400 mL of anhydrous THF at 0° C. was added diethyl azodicarboxylate (31.49 mL, 0.20 mol) dropwise. The mixture was stirred at 0° C. for 30 minutes, then brought to room temperature. (S)-5-(Hydroxymethyl)-2-pyrrolidinone (Aldrich Chemical Co., 15.19 g, 0.13 mol) and 3-hydroxypyridine (19.02 g, 0.20 mol) were added to the reaction vessel, and stirred for 16 hours. Solvent was removed in vacuo. The residue was diluted with CH$_2$Cl$_2$ and washed with 1N NaOH. After a brine wash (2×), the organic layer was dried over MgSO$_4$. The residue was purified by silica gel flash chromatography using a gradient from 100% CHCl$_3$ to 10% MeOH/CHCl$_3$ (purification system was run twice), then recrystallized with ethyl acetate to give 4.0 g (16%) of the title compound as a white powder, mp.= 121–122° C. TLC $R_f$=0.3 1 (10%MeOH/CHCl$_3$). MS (DCI/ NH$_3$) m/e: 193 (M+H)$^+$ and 210 (M+NH$_4$)$^+$. $^1$H NMR (CDCl$_3$, 300 MHz) δ: 8.32–8.30 (m, 1H), 8.27 (dd, J=4.40, 1.50 Hz, 1H), 7.25–7.16 (m, 2H), 6.17 (br s, 1H), 4.14–4.08 (m, 1H), 4.05 (dd, J=8.80, 3.70 Hz, 1H), 3.89 (dd, J=8.80, 7.70 Hz, 1H), 2.49–2.23 (m, 3H), 1.99–1.87 (m, 1H). Anal. Calc. for C$_{10}$H$_{12}$N$_2$O$_2$: C, 62.49; H, 6.29; N, 14.57; Found C, 62.53; H, 6.25; N, 14.71.

22b. 3-((1-methyl-5-oxo-2-(S)-pyrrolidinyl)methoxy) pyridine

To a solution of the compound from step 22a above (0.100 g, 0.52 mmol) in anhydrous THF at 0° C. was added NaH (80% dispersion, 0.02 g, 0.83 mmol) was added, and the reaction mixture was stirred for 20 minutes at this temperature. The reaction was then warmed to room temperature, and iodomethane (0.06 mL, 0.89 mmol) was added via syringe. After starting material was consumed, NaHCO$_3$ was added to the reaction followed by CH$_2$Cl$_2$. The desired compound was extracted from the aqueous phase, and the organic layer was subjected to a brine wash (2×). The organic layer was dried over MgSO$_4$. The residue was purified by silica gel flash chromatography (5% MeOH/ CHCl$_3$) to give 0.107 g (100%) of the title compound as a white powder. mp.=73–74° C. MS (DCI/NH$_3$) m/e: 207 (M+H)$^+$ and 224 (M+NH$_4$)$^+$. $^1$H NMR (CDCl$_3$, 300 MHz) δ: 8.33–8.28 (m, 2H), 7.24–7.18 (m, 2H), 4.14 (dd, J=9.50, 4 Hz, 1H), 4.04 (dd, J=9.50, 4.40 Hz, 1H), 3.95–3.89 (m, 1H), 2.92 (s, 3H), 2.55–2.50 (m, 1H), 2.45–2.21 (m, 2H), 2.02–1.94 (m, 1H). Anal. Calc. for C$_{11}$H$_{14}$N$_2$O$_2$: C, 64.06; H, 8.84; N, 13.58; Found C, 64.07; H, 6.67; N, 13.67. $[\alpha]^{25}_D$=+37.30° (c=1.03, MeOH).

22c. 3-((cis-1,5-dimethyl-2-(S)-pyrrolidinyl)methoxy pyridine

To a solution of the compound of step 22b above (0.400 g, 1.94 mmol) in anhydrous THF at 0° C. was added MethylMgCl (Aldrich Chemical Co., 3M solution in THF, 1.94 mL, 5.80 mmol). An immediate precipitate formed in the reaction, but the reaction was stirred at this temperature for 2 hours. The reaction was then brought to room temperature and sonicated for 30 minutes followed by stirring for an hour. After the starting material was consumed the reaction was quenched with MeOH. Bromocresol green indicator was added followed by enough 2N HCl/MeOH to turn the color of the reaction mixture yellow (acidic pH). Sodium cyanoborohydride (0.182 g, 2.92 mmol) was added to the reaction and the mixture was stirred for an additional 3 hours (adding 2N HCl/MeOH to maintain the pH). Saturated K$_2$CO$_3$ was added to the reaction mixture slowly. After the aqueous phase tested basic, CH$_2$Cl$_2$ was added to extract the desired material. The organic layer was then washed with a brine solution (2×) and dried over MgSO$_4$. The resulting material was purified by silica gel flash chromatography (10%MeOH/CHCl$_3$) to give 0.170 g (42.5%) of the cis-5'-methyl compound and 0.057 g (14%) of the trans-5'-compound (the data for the cis compound given). MS (DCI/NH$_3$) m/e: 207 (M+H)$^+$. $^1$H NMR (CDCl$_3$, 300 MHz) δ: 8.32 (m, 1H), 8.20 (t, J=3 Hz, 1H, 7.20–7.18 (m, 2H), 4.05 (dd, J=9.20, 5.50 Hz, 1H), 3.89 (dd, J=9.20, 6.25 Hz, 1H), 2.80–2.75 (m, 1H), 2.41 (s, 3H), 2.40–2.37 (m, 1H), 2.01–1.87 (m, 2H), 1.65–1.61 (m, 1H), 1.47–1.44 (m, 1H), 1.13 (d, J=6.25 Hz, 3H).

22d. 3-((cis-1,5-dimethyl-2-(S)-pyrrolidinyl)methoxy) pyridine dihydrochloride

The free base from step 22c above was dissolved in diethyl ether and brought to 0° C. with stirring. The solution was treated with diethyl ether saturated with hydrogen chloride gas. The solvent was removed in vacuo. The resulting salt was triturated with diethyl ether (2×) and dried under vacuum to give a white powder. MS (DCI/NH$_3$) m/e: 207 (M+H)$^+$. $^1$H NMR (D$_2$O, 300 MHz) δ: 8.41 (br s, 1H), 8.31 (d, J=4.40 Hz, 1H), 7.81–7.77 (m, 1H), 7.66 (dd, J=8.80, 5.10 Hz, 1H), 4.57 (dd, J=11.40, 3 Hz, 1H), 4.44 (dd, J=8.80, 5.90 Hz, 1H), 4.03–3.96 (m, 1H, 3.61–3.53 (m, 1H), 3.03 (s, 3H), 2.43–2.30 (m, 2H), 2.14–2.03 (m, 1H), 1.92–1.81 (m, 1H), 1.47 (d, J=6.6 Hz, 3H). Anal. Calc. for C$_{12}$H$_{18}$N$_2$O.2.20 HCl: C, 50.31; H, 7.11; N, 9.78; Found C, 50.07; H, 7.10; N, 9.77. $[\alpha]_D^{25}$=+8.60° (c=1, MeOH).

EXAMPLE 23

3-((trans-1-methyl-hydroxy-2(S)-pyrrolidinyl) methoxy)pyridine dihydrochloride 23a. 3-((trans-1-methyl-4-hydroxy-5-oxo-2(S)-pyrrolidinyl) methoxy)pyridine A sample of the compound (1.0 g, 5.6 mmol) from Example 22b was dissolved in 25 mL of THF and cooled to −78° C. Lithium diisopropyl amide (LDA) solution (1.5 M in hexane, 7.5 mL, 11.2 mmol) was added, and the solution was stirred at −78° C. for 30 min. Next a solution of 1.17 g (5.12 mmol) of (+)-(camphorsulfonyl)oxaziridine in 24 mL of THF was added. After stirring at −78° C. for 1 h, the reaction mixture was gradually warmed to room temperature and stirred for an additional 2 hours. The reaction was then quenched by addition of methanol. The resultant mixture was stirred for 15 min, and the solvent was removed. The residue was subjected to flash chromatography on silica gel using chloroform:methanol (10:1) as eluant. The title compound was isolated as aa oil (0.76 g, 69% yield). MS m/e: 223 (M+H)$^+$, 240 (M+NH$_4$)$^{+'}$. $^1$H NMR (CDCl$_3$, 300 MHz) δ: 8.37–8.26 (m, 2H), 7.31–7.16 (m, 2H), 4.59 (t, J=7.5 Hz, 1H,), 4.18 (dd, J=4.5, 9 Hz, 1H), 4.04 (dd, J=4.5, 9 Hz, 1H), 3.96–3.88 (m, 1H), 2.96 (s, 3H), 2.52–2.42 (m, 1H), 2.21–1.98 (m, 1H).

23b. 3-((trans-1-methyl-hydroxy-2(S)-pyrrolidinyl) methoxy)pyridine

To the compound of step 23a (275 mg, 1.24 mmol) in 5 mL of THF was added, under nitrogen and dropwise over a period of 5 minutes, 2.5 mL (2.48 mmol) of a 1 M solution of borane in THF. After stirring under reflux for 3 hours, methanol was added dropwise, and the reaction was stirred for an additional 15 minutes. The solvent was then removed in vacuo, affording a white solid borane complex. This solid was dissolved in anhydrous ethanol. Cesium fluoride (0.286 g, 2.48 mmol) was added, and the resultant solution was stirred under reflux for 16 hr. Evaporation of the solvent provided a white solid which was purified on a silica gel column, eluting with chloroform:methanol (10:1) to give 220 mg of the desired alcohol as an oil in 85% yield. TLC R$_f$=0.38 (10:1CHCl$_3$: MeOH). MS m/e: 209 (M+H)$^+$. $^1$H NMR (CDCl$_3$, 300 MHz) δ: 8.35–8.33 (m, 1H), 8.25–8.21 (m, 1H), 7.24–7.20 (m, 2H), 4.54–4.44 (m, 1H), 4.08–3.97 (m, 2H), 3.52–3.44 (m, 1H), 3.08–2.99 (m, 1H), 2.51 (s, 3H), 2.43–2.33 (m, 1H), 2.14–1.97 (m, 2H).

23c. 3-((trans-1-methyl-4-hydroxy-2(S)-pyrrolidinyl) methoxy)pyridine dihydrochloride A solution of HCl in ether was added dropwise to a stirred solution of compound 23b (220 mg, 1.05 mmol) in diethyl ether at room temperature. The resultant white precipitate was then collected by centrifugation and triturated with three portions of diethyl ether. The hygroscopic solid was obtained in 59% yield (174 mg). mp 145–147° C. MS m/e (DCI/NH$_3$): 209 (M+H)$^+$, 226 (M+NH$_4$)$^+$. $^1$H NMR (D$_2$O, 300 MHz) δ: 8.42 (d, J=2.6 Hz, 1H), 8.32 (d, J=4.4 Hz, 1H), 7.77–7.85 (m, 1H), 7.66 (dd, J=5.1, 8.4 Hz, 1H), 4.64 (dd, J=4.6, 11.0 Hz, 1H), 4.44 (dd, J=5.9, 11.4 Hz, 1H), 4.34–4.21 (m, 1H), 4.04–3.89 (m, 1H, 3.20–3.11 (m, 1H), 3.34–3.03 (m, 1H), 3.15 (s, 3H), 2.38–2.34 (m, 2H). Anal. Calc. for C$_{11}$H$_{16}$N$_2$O$_2$.1.9 HCl.0.1H$_2$O: C, 47.30; H, 6.53; N, 10.01. Found: C, 47.63; H, 6.42; N, 9.68. [α]$_D$=+2.2° (c 0.41, MeOH).

EXAMPLE 24

3-((trans-1,4-dimethyl-2(S)-pyrrolidinyl)methoxy) pyridine dihydrochloride 24a. 3-((trans-1,4-dimethyl-5-oxo-2(S)-pyrrolidinyl) methoxy) pyridine A sample of lactam (0.17 g, 0.83 mmol) from Example 22b was dissolved in 5 mL of THF and cooled to −78° C. Lithium diisopropyl amide (LDA) solution (1.5 M in hexane, 1.11 mL, 1.66 mmol) was added, and the solution was stirred at 0° C. for 30 min. After cooling to −78° C., MeI (0.1 mL, 1.66 mmol) was added, and the resultant solution was stirred at −78° C. for 3 hours. The reaction was then quenched by addition of saturated ammonium chloride aqueous solution. The resultant mixture was stirred for 15 min, and the aqueous layer was extracted with ethyl acetate. The combined organic layers were then dried over anhydrous magnesium sulfate. Filtration and concentration under vacuum provided a yellow oil, which was subjected to flash chromatography on silica gel using chloroform: methanol (10:1) as eluant. The title compound was isolated as an oil (0.13 g, 75% yield). TLC R$_f$=0.10 (100:1CHCl$_3$: MeOH). MS m/e: 221 (M+H)$^+$, 238 (M+NH$_4$)$^+$. $^1$H NMR (CDCl$_3$, 300 MHz) δ: 8.37–8.22 (m, 2H), 7.35–7.23 (m, 2H), 4.09 (ddd, J=4.5, 9.0, 15 Hz, 2H,), 3.89–3.81 (m, 1H), 2.93 (s, 3H), 2.73–2.60 (m, 1H), 2.29–2.20 (m, 1H),1.23 (d, J=8 Hz, 3H).

24b. 3-((trans-1,4-dimethyl-2(S)-pyrrolidinyl)methoxy) pyridine

To the compound of step 24a (130 mg, 0.63 mmol) in 4 mL of THF was added, under nitrogen and dropwise over a period of 5 minutes, 1.25 mL (1.25 mmol) of a 1 M solution of borane in THF. After stirring under reflux for 2 hours, methanol was added dropwise and the reaction was stirred for an additional 15 minutes. The solvent was then removed in vacuo, affording a white solid borane complex. This solid was dissolved in anhydrous ethanol. Cesium fluoride (0.218 g, 1.89 mmol) was added, and the resultant solution was stirred under reflux for 16 hr. Evaporation of the solvent provided a white solid which was purified on a silica gel column, eluting with chloroform:methanol (10:1) to give 59 mg of the desired methyl compound as an oil in 46% yield. TLC R$_f$=0.16 (10:1CHCl$_3$: MeOH). MS m/e: 207 (M+H)$^+$. $^1$H NMR (CDCl$_3$, 300 MHz) δ: 8.34 (brs, 1H), 8.26–8.18 (m, 1H), 7.25–7.18 (m, 2H), 4.20–4.02 (m, 1H), 4.02–3.90 (m, 1H), 3.33–3.21 (m, 1H), 3.00–2.80 (m, 1H), 2.54 (s, 3H), 2.45–2.30 (m, 1H), 2.12–1.91 (m, 2H), 1.74.1.54 (m, 1H), 1.06 (d, J=8.0 Hz).

24c. 3-((trans-1,4-dimethyl-2(S)-pyrrolidinyl)methoxy) pyridine dihydrochloride

A solution of HCl in ether was added dropwise to a stirred solution of compound 24b (55 mg, 0.27 mmol) in diethyl ether at room temperature. The resultant white precipitate was then collected by centrifugation and triturated with three portions of diethyl ether. The hygroscopic solid was obtained in 56% yield (42 mg). mp 223–225° C. MS m/e (DCI/NH$_3$): 207 (M+H$^+$). $^1$H NMR (DMSO-d$_6$, 300 MHz) δ: 8.65 (d, J=2.9 Hz, 1H), 8.46 (d, J=5.9 Hz, 1H), 8.00 (dd, J=2.3, 8.7 Hz, 1H), 7.81 (dd, J=5.2, 8.7 Hz, 1H), 4.60 (dd, J=8.1, 11.0 Hz, 1H), 4.49 (dd, J=3.5, 10.4 Hz, 1H), 4.04–3.95 (m, 1H), 3.64–3.58 (m, 1H), 2.92 (s, 3H), 2.80–2.74 (m, 1H), 2.45–2.40 (m, 1H), 2.04–1.98 (m, 1H), 1.95–1.89 (m, 1H), 1.07 (d, J=6.9 Hz, 3H). Anal. Calc. for C$_{12}$H$_{18}$N$_2$O.2.0 HCl: C, 51.62; H, 7.22; N, 10.03. Found: C, 51.84; H, 7.36; N, 9.90. [α]$_D$=−2.3° (c=0.32, MeOH).

EXAMPLE 25

3-((trans-1-methyl-4-ethhl-2(S)-pyrrolidinyl) methoxy)pyridine dihydrochloride 25a. 3-((trans-1-methyl-4-ethyl-5-oxo-2(S)-pyrrolidinyl) methoxy)pyridine A sample of lactam (0.195 g, 0.94 mmol) from Example 22b was dissolved in 3 mL of THF and cooled to −78° C. Lithium diisopropyl amide (LDA) solution (1.5 M in hexane, 0.94 mL, 1.42 mmol) was added and the solution was stirred at −78° C. for 30 min. EtI (0.113 mL, 1.42 mmol) was then added and the resultant solution was stirred at −78° C. for 3 hours and gradually warmed to room temperature. The reaction was quenched by addition of saturated ammonium chloride aqueous solution. The resultant mixture was stirred for 15 min and the aqueous layer was extracted with ethyl acetate. The combined organic layers were then dried over anhydrous magnesium sulfate. Filtration and concentration under reduced pressure provided a yellow oil which was subjected to flash chromatography on silica gel using chloroform:methanol (10.1) as eluanl The title compound was isolated as an oil (0.216 g, 98% yield). TLC $R_f$=0.42 (10:1 CHCl$_3$:MeOH). MS m/e: 235 (M+H)$^+$. $^1$H NMR (CDCl$_3$, 300 MHz) δ: 8.35–8.29 (m, 1H), 8.30–8.25 (m, 1H), 7.25–7.16 (m, 2H), 4.18–4.00 (m 2H), 3.89–3.75 (m, 1H), 2.94 (s, 3H), 2.62–2.48 (m, 1H), 2.23–2.12 (m, 1H), 2.00–1.80 (m, 2H), 1.70–1.30 (m, 2H), 0.98 (t, J=7.5 Hz, 3H).

25b. 3-((trans-1-methyl-4-ethyl-2(S)-pyrrolidinyl)methoxy)pyridine

To the compound of step 25a (230 mg, 0.63 mmol) in 2 mL of THF was added under nitrogen and dropwise over a period of 5 minutes 2.95 mL (2.95 mmol) of a 1 M solution of borane in THF. After stirring under reflux for 3 hours, methanol was added dropwise and the reaction stirred for an additional 15 minutes. The solvent was then removed in vacuo, affording a white solid borane complex. This solid was dissolved in anhydrous ethanol. Cesium fluoride (0.335 g, 2.95 mmol) was added, and the resultant solution was stirred under reflux overnight. Evaporation of the solvent provided a white solid which was purified on a silica gel column, eluting with chloroform:methanol (10:1) to give 104 mg of the desired methyl compound as an oil in 48% yield. TLC $R_f$=0.14 (10:1CHCl$_3$: MeOH). MS m/e: 221 (M+H)$^+$. $^1$H NMR (CDCl$_3$, 300 MHz) δ: 8.35–8.31 (m, 1H), 8.24–8.19 (m, 1H), 7.24–7.18 (m, 2H), 4.08–3.86 (m, 2H), 3.25–3.15 (m, 1H), 2.80–2.66 (m, 1H), 2.47 (s, 3H), 2.20–2.04 (m, 1H), 1.99 (dd, J=9.0, 9.6 Hz, 1H), 1.95–1.85 (m, 1H), 1.72–1.57 (m, 2H), 1.48–1.31 (m, 2H), 0.92 (t, J=8.0 Hz).

25c. 3-((trans-1-methyl-4-ethyl-2(S)-pyrrolidinyl)methoxy)pyridine dihydrochloride A solution of hydrochloride in ether was added dropwise to a stirred solution of compound 25b (55 mg, 0.27 mmol) in diethyl ether at room temperature. The resultant white precipitate was then collected by centrifugation and triturated with three portions of diethyl ether. The hygroscopic solid was obtained in 56% yield (42 mg). mp 219–220° C. MS m/e (DCI/NH3): 221 (M+H$^+$). $^1$H NMR (D$_2$O, 300 MHz) δ: 8.45 (d, J=2.6 Hz, 1H), 8.36 (d, J=5.1 Hz, 1H), 7.91 (m, 1H), 7.76 (dd, J=5.2, 8.8 Hz, 1H), 4.59 (dd, J=2.9, 11.0 Hz, 1H), 4.43 (dd, J=5.9, 11.0 Hz, 1H), 4.04–3.95 (m, 1H), 4.08–4.00 (m, 1H), 3.83 (dd, J=6.6, 11.0 Hz), 3.05 (s, 3H), 2.95 (t, J=11.0 Hz, 1H), 2.45–2.00 (m, 2H), 2.14–2.03 (m, 1H), 1.60–1.45 (m, 2H), 0.94 (t, J=7.4 Hz, 3H). Anal, Calcd. for C$_{13}$H$_{20}$N$_2$O.1.9 HCl: C, 53.92; H, 7.62; N, 9.67. Found: C, 54.00; H, 7.59; N, 9.35. [α]$_D$=−1.9° (c 0.37, MeOH).

EXAMPLE 26

3-((1-methyl-2-piperidinyl)methoxy)pyridine oxalate salt

1-Methyl-2-piperidinemethanol (0.857 g, 6.65 mmol) was allowed to react with 3-bromopyridine (0.67 mL, 6.98), cuprous bromide (0.257 g, 1.33 mmol), triphenylphosphine (0.698 g, 2.66 mmol) and potassium carbonate (0.919 g, 6.65 mmol). The reaction mixture was heated to 90° C. and stirred for 120 hr, then cooled to 25° C., acidified with HCl (1.5 M; 35 mL) and washed with ethyl acetate (4×50 mL). The aqueous layer was basified with saturated aqueous potassium carbonate, and the product was extracted with chloroform (6×100 mL), dried (MgSO$_4$) and concentrated in vacuo to an oil. The crude product was purified to yield the free base of the title compound after chromatography on silica gel (CHCl$_3$/MeOH/NH$_4$OH 1500:30:3). The amine was dissolved in EtOH (1 mL) and treated with oxalic acid (ca. 65 mg) to yield after recrystallization (EtOH/Et$_2$O) the title compound (0.088 g, 4%) as a hygroscopic white solid. MS (DCI/NH$_3$) m/e: 207 (M+H)$^+$. $^1$H NMR (D$_2$O, 300 MHz) δ: 8.46 (d, J=2.9 Hz, 1H), 8.37 (dd, J=5.2, 1.1 Hz, 1H), 7.94 (ddd, J=8.8, 2.9, 1.1 Hz, 1H), 7.80 (dd, J=8.8, 5.9 Hz, 1H), 4.69 (dd, J=11.2, 3.1 Hz, 1H), 4.35 (dd, J=11.2, 2.0 Hz, 1H), 3.56 (m, 2H), 3.18 (dt, J=12.7, 3.0 Hz, 1H), 2.93 (s, 3H), 2.05–1.65 (m, 6H). Anal. calcd for C$_{14}$H$_{20}$N$_2$O$_5$.0.4 C$_2$H$_2$O$_4$: C, 53.49; H, 6.31; N, 8.43. Found: C, 53.39; H, 6.09; N, 8.19.

EXAMPLE 27

4-methyl-3-(2-(S)-pyrrolidinylmethoxy)pyridine dihydrochloride 27a. 4-methyl-3-pyridyl diethylcarbamate To the cooled (−78° C.) solution of TMEDA (516.5 mg, 4.40 mmol) in anhydrous THF (10 mL) was slowly added sec-butyl lithium (1.3 M, 3.38 mL, 4.40 mmol), and the resultant solution was stirred at −78° C. for 10 minutes. 3-Pyridyl diethylcarbamate (776 mg, 4.0 mmol) in THF (3 mL) was slowly added, and the mixture was stirred at −78° C. for 30 minutes. Iodomethane (275.4 μL, 4.40 mmol) was then added, and the mixture was stirred for two hours. Brine (1 mL) was added, and the mixture was slowly warmed up to room temperature. The organic layer was decanted, and the residue washed with ethyl acetate (3×5 mL). The combined organic layers were dried (Na$_2$SO$_4$) and concentrated. The crude product was purified by chromatography on silica gel eluting with hexane/EtOAc (1:2 and 0:1) to provide 765 mg (92% yield) of the title compound. TLC R$_f$ 0.28 (1:2 hexane/EtOAc). MS (DCI/NH$_3$) m/e 209 (M+H)$^+$. $^1$H NMR (CDCl$_3$, 300 MHz) δ: 8.34 (s, 1H, ArH), 8.32 (d, J=6.9 Hz, 1H, ArH), 7.16 (d, J=6.9 Hz, 1H, ArH), 3.48 (q, J=7.5 Hz, 2H, NCH$_2$), 3.41 (q, J=7.5 Hz, 2H, NCH$_2$), 1.28 (t, J=7.5 Hz, 3H, CH$_3$), 1.22 (t, J=7.5 Hz, 3H, CH$_3$).

27b. 4-methyl-3-pyridinol

To the solution of 4-methyl-3-pyridyl diethylcarbamate (760 mg, 3.65 mmol) in methanol (10 mL) was added sodium methoxide (623 mg, 11.0 mmol), and the resultant mixture was refluxed for 20 hours. Methanol was evaporated, EtOAc (15 mL) and water (1 mL) were added, pH was adjusted to 9 using 20% yield H$_2$SO$_4$. Organic layer was decanted and the residue washed with EtOAc (3×5 mL). The combined organic layers were dried (Na$_2$SO$_4$) and concentrated. The crude product was purified by flash chromatography on silica gel eluting with CHCl$_3$/MeOH (20:1 and 10:1) to provide 325 mg (82% yield) of the title compound. TLC R$_f$ 0.30 (10:1 CHCl$_3$/MeOH). MS (DCI/NH$_3$) m/e 110 (M+H)$^+$. $^1$H NMR (CDCl$_3$, 300 MHz) δ: 8.24 (s, 1H, ArH), 7.98 (d, J=7.2 Hz, 1H, ArH), 7.16 (d, J=7.2 Hz, 1H, ArH).

27c. 4-methyl-3-(2-(S)-pyrrolidinylmethoxy)pyridine (S)-1-t-Butoxycarbonyl-2-pyrrolidinemethanol (590 mg, 2.94 mmol), 4-methyl-3-pyridinol (320 mg, 2.94 mmol), DEAD (509 uL, 3.23 mmol) and PPh3 (848 mg, 3.23 mmol) in THF (100 mL) were allowed to react as described in Example 2a. Solvent was removed, and the residue was chromatographed with CHCl$_3$/MeOH (10:1) to provide 1.8 g of the crude mixture. This material was immediately treated with trifluoroacetic acid (2.0 mL) at room temperature for 3 hours, and excess trifluoroacetic acid was removed under reduced pressure. Water (3 mL) and EtOAc (20 mL) were added, and the mixture was stirred for 5 minutes. The organic layer was decanted, and the residue washed with EtOAc (3×10 mL). The combined organic layers were dried (Na$_2$SO$_4$) and evaporated. The crude product was purified by flash chromatography on silica gel eluting with CHCl$_3$/MeOH/NH$_4$OH (10:1:0.02 and 10:1.5:0.1) to provide 52 mg (14% yield from 4-methyl-3-pyridinol) of the title compound. TLC R$_f$ 0.18 (10:1:0.02 CHCl$_3$/MeOH/NH$_4$OH). MS (DCI/NH$_3$) m/e 193 (M+H)$^+$. $^1$H NMR (CDCl$_3$, 300 MHz) δ: 8.16 (s, 1H, ArH), 8.12 (d, J=6.9 Hz, 1H, ArH), 7.07 (d, J=6.9 Hz, 1H, ArH), 4.12–4.00 (m, 2H, OCH$_2$), 3.75–3.63 (m, 1H, NCH), 3.18–3.02 (m, 2H, NCH$_2$), 2.24 (s, 3H, NCH$_3$), 2.08–1.64 (m, 4H, 2CH$_2$).

27d. 4-Methyl-3-(2-(S)pyrrolidinylmethoxy)pyridine dihydrochloride

The compound of step 27c was trated with HCl and isolated as described in Example 1b to afford a cream colored powder. MS (DCI/NH$_3$) m/e 193 (M+H)$^+$. $^1$H NMR (D$_2$O, 300 MHz) d: 8.34 (s, 1H, ArH), 8.33 (d, J=5.5 Hz, 1H, ArH), 7.82 (d, J=5.5 Hz, 1H, ArH), 4.60 (dd, J=3.3, 10.3 Hz, 1H, OCHH), 4.37 (dd, J=7.4, 10.3 Hz, 1H, OCHH), 4.25–4.17 (m, 1H, NCH), 3.44 (t, J=7.4 Hz, 2H, NCH$_3$), 2.50 (s, 3H, NCH$_3$), 2.40–1.98 (m, 4H, 2CH$_2$). Anal. Calc. for C$_{11}$H$_{18}$N$_2$OCl$_2$.0.30 HCl: C, 47.85; H, 6.76; N, 10.21. Found: C, 48.01; H, 6.44; N, 10.19.

EXAMPLE 28

5-bromo-3-((1-methyl-2-(S)-pyrrolidinyl)methoxy)pyridine dihydrochloride 28a. 5-bromo-3-((1-methyl-2-(S)-pyrrolidinyl)methoxy)pyridine (S)-1-Methyl-2-pyrrolidinemethanol (4.96 g, 40.0 mmol) was carefully added to the suspension of sodium hydride (1.32 g, 80% yield, 44.0 mmol) in anhydrous DMF (100 mL). After stirring at room temperature for 0.5 hour, 3,5-dibromopyridine (4.83 g, 20.0 mmol) was added, and the reacting mixture was stirred at 50° C. for 4 hours. Another 5.0 mL of water was added, and the solvents were removed under reduced pressure. Again, water (5.0 mL) was added, and the slurry was washed extensively with EtOAc (4×40 mL). The combined organic layers were dried (Na$_2$SO$_4$) and concentrated. The crude product was purified by flash chromatography on silica gel eluting with CHCl$_3$/MeOH (10:1) to provide 4.50 g (83% yield) of the title compound. TLC R$_f$ 0.33 (10:1 CHCl$_3$/MeOH). MS (DCI/NH$_3$) m/e 271 with $^{79}$Br and 273 (M+H)$^+$ with $^{81}$Br. $^1$H NMR (CDCl$_3$, 300 MHz) δ: 8.37 (d, J=1.8 Hz, 1H, ArH), 8.26 (d, J=2.7 Hz, 1H, ArH), 7.39 (dd, J=1.8, 2.7 Hz, 1H, ArH), 4.01 (dd, J=3.3, 11.1 Hz, 1H, OCHH), 3.93 (dd, J=6.9, 11.1 Hz, 1H, OCHH), 3.20–3.10 (m, 1H, NCH), 2.76–2.64 (m, 1H, NCH), 2.49 (s, 3H, NCH$_3$), 2.40–2.28 (m, 1H, NH), 2.44–2.00 (m, 4H, 2CH$_2$).

28b. 5-bromo-3-((1-methyl-2-(S)-pyrrolidinyl)methoxy)pyridine dihydrochloride

The compound of step 28a (190 mg) was treated with HCl and isolated as described in Example 1b to afford 170 mg (71% yield) of the title compound as a light yellow powder. mp 223–225° C. MS (DCI/NH$_3$) m/e 271 with $^{79}$Br and 273 (M+H)$^+$ with $^{81}$Br. $^1$H NMR (CDCl$_3$, 300 MHz) d: 8.42 (d, J=1.5 Hz, 1H, ArH), 8.35 (d, J=2.7 Hz, 1H, ArH), 7.93 (dd, J=1.5, 2.7 Hz, 1H, ArH), 4.55 (dd, J=3.0, 11.4 Hz, 1H, OCHH), 4.38 (dd, J=6.3, 11.4 Hz, 1H, OCHH), 3.98–3.86 (m, 1H, NCH), 3.80–3.72 (m, 1H, NCH), 3.30–3.20 (m, 1H, NCH), 3.03 (s, 3H, NCH$_3$), 2.44–2.00 (m, 4H, 2CH$_2$). Anal. Calc. for C$_{12}$H$_{16}$N$_2$OClF$_3$.0.10 Et$_2$O: C, 38.96; H, 5.16; N, 7.93. Found: C, 39.05; H, 4.80; N, 8.27.

EXAMPLE 29

2-methyl-3-(2-(S)-azetidinylmethoxy)pyridine dihydrochloride 29a. 2-methyl-3-((1-t-Butoxycarbonyl-2-(S)-azetidinyl)methoxy)pyridine An ice-cooled solution of 1-t-butoxycarbonyl-2-(S)-azetidinemethanol (from Example 7b, 0.623 g, 3.33 mmol) was allowed to react with 2-methyl- 3-hydroxypyridine (0.399 g, 3.66 mmol) under the conditions of Example 2a to yield the title compound (0.511 g, 55%). MS (DCI/NH$_3$) m/e: 279 (M+H)$^+$. $^1$H NMR (CDCl$_3$, 300 MHz) δ: 8.10 (dd, J=4.4, 1.5 Hz, 1H), 7.15–7.06 (m, 2H), 4.54–4.53 (m, 1H), 4.35–4.34 (m, 1H), 4.07 (dd, J=10.3, 2.6 Hz, 1H), 3.96–3.88 (m, 2H), 2.51 (s, 3H), 2.42–2.31 (m, 2H), 1.40 (s, 9H).

29b. 2-methyl-3-(2-(S)-azetidinylmethoxy)pyridine dihydrochloride

The compound from step 29a (0.181 g, 0.65 mmol) was treated with saturated ethanolic HCl (5 mL). After 4 hr, the volatiles were removed in vacuo, and the dihydrochloride was recrystallized (EtOH/Et$_2$O) to yield the title compound (0.157 g, 96% yield) as a white solid. mp 153–154° C. MS (DCI/NH$_3$) m/e: 179 (M+H)$^+$. $^1$H NMR (D$_2$O, 300 MHz) d: 8.21–8.19 (d, J=5.5 Hz, 1H), 7.94 (d, J=8.4 Hz, 1H), 7.74 (dd, J=5.5, 3.1 Hz, 1H), 5.04–4.93 (m, 1H), 4.61–4.50 (m, 2H), 4.21–4.08 (m, 2H), 2.78–2.65 (m, 2H), 2.69 (s, 3H). Anal. calc. for C$_{10}$H$_{16}$Cl$_2$N$_2$O.0.8H$_2$O: C, 45.23; H, 6.68; N, 10.55. Found: C, 45.15; H, 6.85; N, 10.51. [α]$^D_{23}$+7.27° (c=0.11 in MeOH).

EXAMPLE 30

2-Methyl-3-((1-methyl-2-(S)-azetidinyl)methoxy)pyridine dihydrochloride

A 252.1 mg sample of 2-methyl-3-((1-t-Butoxycarbonyl-2-(S)-azetidinyl)methoxy)pyridine, from Example 29a above, was stirred with 2 mL of formic acid and 4 mL of formaldehyde at 90° C. for 26 hours. The solvent was removed under vacuum, and the residue was dissolved in 10% KHSO4. This solution was washed with ethyl acetate, made basic with aqueous K2CO3 solution, then extracted with chloroform. The extract was dried over MgSO4 and filtered, then the solvent was removed. The residue was chromatographed on silica gel, and the product was converted to the salt by treatment with ethanolic HCl. MS (DCI/NH$_3$) m/e: 193 (M+H)$^+$. $^1$H NMR (D$_2$O, 300 Mz) δ: 2.62–2.74 (m, 2H), 2.66 (s, 3H), 3.03 (s, 3H), 4.03 (q, 1H), 434 (q, 1H), 4.58–4.65 (m, 2H), 4.87–4.90 (m, 1H), 7.68 (m, 1H), 7.85 (d, 1H), 8.18 (dt, 1H). Anal. calc. for C$_{11}$H$_{18}$Cl$_2$N$_2$O.1.8H$_2$O: C, 44.39; H, 7.32; N, 9.41. Found: C, 44.55; H, 7.69; N, 9.32.

EXAMPLE 31

3-(1-methyl-2-(S)-pyrrolidinylmethoxy)quinoline hydrochloride

To (S)-1-methyl-2-pyrrolidinylmethanol (1.07 mL, 9.0 mmol) and 3-bromoquinoline (1.46 mL, 10.8 mmol) was added triphenylphosphine (472 mg, 1.8 mmol), CuBr (129 mg, 0.9 mmol) and K$_2$CO$_3$ (1.19 g, 9 mmol), and the reaction mixture was heated to 100° C. for 16 hours. The reaction mixture was then quenched with 10% aq. HCl, and the aqueous layer was washed with methylene chloride (4×15 mL). The aqueous layer was adjusted to approx. pH 14 with K$_2$CO$_3$ (solid) and extracted with methylene chloride (2×30 mL). The organic extracts were dried (MgSO$_4$) and concentrated to afford the crude product as an oil.

Chromatographic purification (silica, MeOH/CHCl³) afforded the product as a free base (571 mg, 26%), which was converted to the hydrochloride salt in a manner similar to Example 1b, using ether instead of ethanol. MS(DCl/NH3) m/e: 243 (M+H)$^+$; $^1$H-NMR (D$_2$O) δ: 8.79 (d, 1H), 8.14 (d, 1H), 8.09–8.0 (m, 2H), 7.86–7.73 (m, 2H), 4.67 (dd, 1H), 4.50 (dd, 1H), 4.02 (m, 1H), 3.80 (m, 1H), 3.30 (m, 1H), 3.10 (s, 3H), 2.53–2.38 (m, 1H), 2.30–2.09 (m, 2H). Anal. Calc for C$_{15}$H$_{18}$N$_2$O.2HCl: C, 57.15; H, 6.39; N, 8.89; Found: C, 57.14; H, 6.35; N, 8.90.

EXAMPLE 32

4-(1-methyl-2-(S)-pyrrolidinylmethoxy)isoquinoline hydrochloride

To (S)-1-methyl-2-pyrrolidinyl methanol (1.07 mL, 9.0 mmol) and 4-bromoisoquinoline (2.24 g, 10.8 mmol) was added triphenylphosphine (472 mg, 1.8 mmol), CuBr (129 mg, 0.9 mmol) and K$_2$CO$_3$ (1.19 g, 9 mmol), and the reaction mixture was heated to 100° C. for 16 hours. The reaction mixture was then quenched with 10% aq. HCl and the aqueous layer was washed with methylene chloride (4×15 mL). The aqueous layer was then adjusted to approx. pH 14 with K$_2$CO$_3$ (solid) and extracted with methylene chloride (2×30 mL). The organic extracts were dried (MgSO$_4$) and concentrated to afford the crude product as an oil. Chromatographic purification (silica, MeOH/CHCl$_3$) gave the product as a free base (216 mg, 10%), which was converted to the hydrochloride salt in a manner similar to Example 1b, using ether instead of ethanol. MS(DCl/NH$_3$) m/e: 243 (M+H)$^+$; $^1$H-NMR (D$_2$O) δ: 9.33 (s, 1H), 8.50–8.42 (m, 2H), 8.25–8.18 (m, 2H), 8.11–8.03 (m, 1H), 4.96–4.72 (m, 2H; partially buried under H$_2$O peak), 4.16 (m, 1H), 3.84 (m, 1H), 3.25 (m, 1H), 3.17 (s, 3H), 2.57–2.46 (m, 1H), 2.36–2.16 (m, 2H). Anal. Calc for C$_{15}$H$_{18}$N$_2$O.0.5 H$_2$O.2HCl: C, 55.56; H, 6.53; N, 8.64; Found: C, 55.63; H, 6.28; N, 8.50.

EXAMPLE 33

5-chloro-3-(2-(R)-pyrrolidinylmethoxy)pyridine dihydrochloride 33a. (R)-1-t-butoxycarbonyl-2-pyrrolidinemethanol N-t-BOC-(R)-proline was treated as in Example 15a. The resulting material was carried on without any further purification.

33b. 5chloro-3-(N-t-butoxycarbonyl-2-(R)-pyrrolidinylmethoxy)pyridine

Starting with the material from step 33a, and following the procedure of Example 15b, the title compound was prepared. TLC R$_f$ 0.75 (1:1 EtOAc/Hex). MS (DCI/NH$_3$) m/e: 313 (M+H)$^+$ with $^{35}$Cl and m/e: 315 (M+H)$^+$ with $^{37}$Cl.

33c. 5-chloro-3-(2-(R)-pyrrolidinylmethoxy)pyridine dihydrochloride

The product of Example 33b was treated according to the procedures of Examples 2b and 1b to give the title product. The MS and $^1$H NMR (D$_2$O, 300 MHz) were similar to Example 15d. Anal. Calc. for C$_{10}$H$_{13}$N$_2$OCl.2.00 HCl: C, 42.06; H, 5.29; N, 9.81; Found C, 42.91; H, 5.44; N, 9.86. [α]$^{25}$$_D$=−11.15° (c=1, MeOH).

EXAMPLE 34

5-chloro-3-((1-methyl-2-(R)-pyrrolidinyl)methoxy) pyridine dihydrochloride 34a. 5-chloro-3-((1-methyl-2-(R)-pyrrolidinyl)methoxy) pyridine Following the procedure of Example 16a, replacing the 5-chloro-3-(N-t-butoxycarbonyl-2-S)-pyrrolidinylmethoxy) pyridine thereof with 5-chloro-3-(N-t-butoxycarbonyl-2-(R)-pyrrolidinylmethoxy)pyridine (prepared from the (R)-isomer of the starting material following the procedure of Example 15a), the tide compound was prepared. TLC R$_f$=0.23 (10% MeOH/CHCl$_3$). MS and $^1$H NMR (CDCl$_3$, 300 MHz) are similar to 16a.

34b. 5-chloro-3-((1-methyl-(R)-pyrrolidinyl)methoxy) pyridine dihydrochloride

The compound of step 34a was treated with HCl as described in Example 1b and the title compound was isolated as a white powder. MS and $^1$H NMR (D$_2$O, 300 Hz) are similar to 16b. Anal. Calc for C$_{11}$H$_{15}$N$_2$OCl.2.00 HCl: C, 44.10; H, 5.20; N, 9.35; Found C, 43.98; H, 5.81; N, 9.33. [α]$^{25}$$_D$=+5.59° (c=1, MeOH).

EXAMPLE 35

2-methyl-3-(2-(R)-pyrrolidinylmethoxy)pyridine dihydrochloride 35a. 2-methyl-3-(2-(R)-pyrrolidinylmethoxy)pyridine Replacing (S)-1-t-butoxycarbonyl-2-pyrrolidinemethanol of Example 15 with (R)-1-t-butoxycarbonyl-2-pyrrolidinemethanol (Aldrich Chemical Co.), and following the procedure of steps 15a and 15b, the title compound was prepared. The MS and $^1$H NMR spectra were similar to compound 15a.

35b. 2-methyl-3-(2-(R)-pyrrolidinylmethoxy)pyridine dihydrochloride

The compound of step 35a was treated with HCl and isolated as described in Example 1b to give a white powder. MS and $^1$H NMR (D$_2$O, 300 Hz) are similar to 17b. Anal. Calc for C$_{11}$H$_{16}$N$_2$O.2.00 HCl: C, 48.82; H, 6.84; N, 10.56; Found C, 49.55; H, 6.95; N, 10.52. [α]$^{25}$$_D$=−27.01° (c=1, MeOH).

EXAMPLE 36

6-methyl-3-((1-methyl-2-(R)-pyrrolidinyl)methoxy) pyridine dihydrochloride 36a. 6-methyl-3-((1-t-butoxycarbonyl-2-(R)-pyrrolidinyl) methoxy)pyridine Replacing the 6-methyl-3-(1-t-butoxycarbonyl-2-(S)-pyrrolidinylmethoxy)pyridine of Example 18b with 6-methyl-3-(1-t-butoxycarbonyl-2-(R)-pyrrolidinylmethoxy)pyridine (prepared from (R)-1-t-butoxycarbonyl-2-pyrrolidinemethanol (Aldrich Chemical Co.) by the procedure described in step 18a), the title compound was prepared by a procedure similar to that of step 18b. TLC Rf=0.42 (1:1 ethyl acetate/hexane).

36b. 6-methyl-3-((1-methyl-2-(R)-prrolidinyl)methoxy) pyridine

The title compound was prepared from the compound of step 36a in a manner similar to compound 18b TLC R$_f$=0.17 (10%MeOH/CHCl$_3$). MS (DCI/NH$_3$) and $^1$H NMR (CDCl$_3$, 300 MHz) are similar to the compound of step 18b.

36c. 6-methyl-3-((1-methyl-2-(R)-pyrrolidinyl)methoxy) pyridine dihydrochloride

The compound of step 36b was treated with HCl as described in Example 1b, and the title compound was isolated as a white powder. The MS and $^1$H NMR spectra were similar to the compound of 18c. Anal. Calc for $C_{12}H_{18}N_2O.2.00$ HCl: C, 51.62; H, 7.22; N,10.03; Found C, 51.36; H, 7.53; N, 9.93. $[\alpha]^{25}_D=^{30}$ 6.22° (c=1, MeOH).

EXAMPLE 37

6-methyl-3-(2-(R)-pyrrolidinylmethoxy)pyridine dihydrochloride

The compound of Example 35a was treated according to the procedures described in Examples 17a and 17b to give the title compound as a white powder. The MS and $^1$H NMR spectra were similar to the compound of 17b. Analysis calculated for $C_{11}H_{16}N_2O.2.00$ HCl: C, 49.82; H, 6.84; N, 10.56; Found C, 49.89; H, 6.59; N, 10.33. $[\alpha]^{25}_D=^-10.47°$ (c=1, MeOH).

EXAMPLE 38

3-((1-ethyl-2(S)-pyrrolidinyl)methoxy)pyridine dihydrochloride 38a. 3-((1-ethyl-2-oxo-5-(S)-pyrrolidinyl)methoxy)pyridine To a solution of the compound from Example 22a (1.50 g, 7.8 mmol) in anhydrous THF at 0° C. was added NaH (60% yield dispersion, 0.625 g, 15.6 mmol) was added, and the reaction mixture was stirred for 20 minutes at this temperature. The reaction was then warmed to room temperature, and iodoethane (1.25 mL, 15.6 mmol) was added via syringe. After starting material was consumed, $NaHCO_3$ was added to the reaction followed by $CHCl_3$. The desired compound was extracted from the aqueous phase, and the organic layer was subjected to a brine wash (2x). The organic layer was dried over $MgSO_4$. The residue was purified by silica gel flash chromatography (5% yield MeOH/$CHCl_3$) to give 0.23 g (13% yield) of the title compound as an oil. MS (DCI/$NH_3$) m/e 221 (M+H)$^+$ and 238 (M+$NH_{4+}$)$^+$. $^1$H NMR ($CDCl_3$, 300 MHz) δ: 8.39–8.33 (m, 1H), 8.33–8.28 (m, 1H), 7.39–7.34 (m, 2H), 4.20–4.00 (m, 3H), 3.78–3.64 (m, 1H), 3.22–3.07 (m, 1H), 2.63–2.49 (m, 1H), 2.47–2.23 (m, 2H), 2.06–1.91 (m, 1H).

38b. 3-((1-ethyl-2-(S)-pyrrolidinyl)methoxy)pyridine

To the compound of step 38a (222 mg, 1.01 mmol) in 3 mL of THF was added, under nitrogen and dropwise over a period of 5 minutes, 3.03 mL (3.03 mmol) of a 1 M solution of borane in THF. After stirring under reflux for 3 hours, methanol was added dropwise, and the reaction was stirred for an additional 30 minutes. The solvent was removed in vacuo, affording a white solid borane complex. This solid was dissolved in anhydrous ethanol. Cesium fluoride (0.347 g, 3.03 mmol) was added, and the resultant solution was stirred under reflux for 16 hr. Evaporation of the solvent provided a white solid which was purified on a silica gel column, eluting with chloroform:methanol (10:1) to give 162 mg of the desired methyl compound as an oil in 78% yield. MS (DCI/$NH_3$) m/e 207 (M+H)$^+$. $^1$H NMR ($CDCl_3$, 300 MHz) δ: 8.36–8.31 (m, 1H), 8.28–8.21 (m, 1H), 7.26–7.20 (m, 2H), 4.30–4.10 (m 1H), 4.02–3.90 (m, 1H), 3.43–3.23 (m, 1H), 3.20–2.90 (m, 1H), 2.68–2.28 (m, 2H), 2.16–1.76 (m, 2H), 1.72–1.44 (m, 1H).

38c. 3-((1-ethyl-2-(S)-pyrrolidinyl)methoxy)pyridine dihydrochloride

The free base from step 38b was dissolved in diethyl ether and brought to 0° C. with stirring. The solution was treated with diethyl ether saturated with HCl. The solvent was removed in vacuo. The resulting salt was triturated with diethyl ether (2x) and dried under vacuumwto give a white powder. MS (DCI/$NH_3$) m/e207 (M+H)$^+$. $^1$H NMR ($D_2O$, 300 MHz) δ: 8.49 (d, J=3.0 Hz, 1H), 8.39 (dd, J=1.0,5.1 Hz, 1H), 8.02 (m, 1H), 7.85 (dd, J=8.70, 5.40 Hz, 1H), 4.61 (dd, J=11.0, 3.3 Hz, 1H), 4.44 (dd, J=11.0, 6.6 Hz, 1H), 4.10–4.01 (m, 1H), 3.79–3.72 (m, 1H), 3.65–3.51 (m, 2H), 3.32–3.18 (m, 2H), 2.44–2.33 (m, 1H), 2.27–2.05 (m, 2H), 1.37 (t, J=7.5 Hz, 3H). Anal. Calc. for $C_{12}H_{18}N_2O.2.0$ HCl: C, 51.57; H, 7.16; N, 10.02; Found C, 51.43; H, 7.39; N, 9.96. $[\alpha]_D=-1.5°$ (c 0.46, MeOH).

EXAMPLE 39

5-chloro-3-(2-(S)-azetidinylmethoxy)pyridine dihydrochloride 39a. 5-chloro-3-(N-t-butoxycarbonyl-2-(S)-azetidinylmethoxy)pyridine An ice-cooled solution of the compound from Example 7b (0.242 g, 1.20 mmol) was allowed to react with 3-chloro-5-hydroxypyridine (0.187 g, 1.40 mmol) under the conditions of Example 2a, except that DEAD was replaced with di-t-butylazodicarbonate, to yield the title compound (0.137 g, 88%) after purification on silica gel (ethyl acetate/hexane 2:1). MS (DCI/$NH_3$) m/e: 299 (M+H)$^+$. $^1$H NMR ($CDCl_3$, 300 MHz) δ: 8.25 (d, J=1.38 Hz, 1H), 8.21 (br. s, 1H), 7.29 (t, J=2.2 Hz, 1H), 4.53–4.51 (m, 1H), 4.34–4.33 (m, 1H), 4.13 (dd, J=10.3, 2.9 Hz, 1H), 3.91–3.86 (m, 2H), 2.51 (s, 3H), 2.38–2.29 (m, 2H), 1.43 (s, 9H).

39b. 5-chloro-3-(2-(S)-azetidinylmethoxy)pyridine dihydrochloride

The compound from step 39a (0.130 g, 0.44 mmol) was treated with saturated ethanolic HCl (5 mL) for 16 hr. The volatiles were removed in vacuo, and the dihydrochloride was recrystallized (EtOH/$Et_2O$) to yield the title compound (0.094 g, 80%) as a white solid. mp 158–157° C. MS (DCI/$NH_3$) m/e: 199 (M+H)$^+$, 216 (M+$NH_4$)$^+$. $^1$H NMR ($D_2O$, 300 MHz) d: 8.41 (d, J=5.1 Hz, 1H), 8.39 (d, J=4.4 Hz, 1H), 7.94 (t, J=2.1 Hz, 1H), 5.01–4.93 (m, 1H), 4.50 (d, J=4.0 Hz, 2H), 4.20–4.03 (m, 2H), 2.69 (q, J=8.45 Hz, 2H). Anal. calc. for $C_9H_{13}Cl_3N_2O.0.5H_2O$: C, 38.53; H, 5.03; N, 9.98 Found: C, 38.51; H, 5.16 N, 9.96. $[\alpha]_D^{23}=-3.23°$ (c=0.16 in MeOH).

EXAMPLE 40

6-methyl-3-(2(S)-azetidinylmethoxy)pyridine dihydrochloride 40a. 6-methyl-3-(N-t-Butoxycarbonyl-2-(S)-azetidinylmethoxy)pyridine An ice cooled solution of the compound from Example 7b (0.232 g, 1.24 mmol) was allowed to react with 3-hydroxy-2-methylpyridine (Aldrich, 0.142 g, 130 mmol) under the conditions of Example 2a, except that DEAD was replaced with di-t-butylazodicarbonate to yield the title compound (0.123 g, 36%) after purification on silica gel (ethyl acetate/hexane 2:1). MS (DCI/$NH_3$) m/e: 279 (M+H)$^+$. $^1$H NMR ($CDCl_3$,300 MHz) δ: 8.23–8.22 (d, J=2.6 Hz, 1H), 7.20 (dd, J=8.5, 3.0 Hz, 1H), 7.08 (d, J=8.5 Hz, 1H), 4.51–4.49 (m, 1H), 4.30–4.28 (m, 1H), 4.13 (dd, J=9.9 ,2.9 Hz, 1H), 3.89 (t, J=7.75 Hz, 2H), 2.51 (s, 3H), 2.37–2.28 (m, 2H), 1.41 (s, 9H).

40b. 6-methyl-3-(2-(S)-azetidinylmethoxy)pyridine dihydrochloride

The compound from step 40a (0.123 g, 0.44 mmol) was treated with saturated ethanolic HCl (5 mL) for 18 hr. The volatiles were removed in vacuo, and the dihydiochloride was washed with $Et_2O$ (3×20 mL), evaporated to dryness and recrystallized (EtOHlEt$_2$O) to yield the title compound (0.074 g, 63%) as a white solid. mp 141–144° C. MS (DCI/NH$_3$) m/e: 179 (M+H)$^+$. $^1$H NMR (D2O, 300 MHz) δ: 8.33 (d, J=2.9 Hz, 1H), 7.89 (dd, J=9.0, 2.8 Hz, 1H), 7.64 (d J=8.8 Hz, 1H), 5.01–4.93 (m, 1H), 4.48 (d, J=4.4 Hz, 2H), 4.21–4.04 (m, 2H), 2.70 (q, J=8.5 Hz, 2H), 2.62 (s, 3H). Anal. calc. for $C_{10}H_{16}Cl_2N_2O.1.0H_2O$: C, 44.62; H, 6.74; N, 10.41. Found: C, 44.55; H, 7.02; N, 10.50. $[\alpha]^D_{24}$ $_{-7.89}$° (c=0.19 in MeOH).

EXAMPLE 41

2-methyl-3-(2-(R)-azetidinylmethoxy)pyridine dihydrochloride 41a. 1-t-butoxycarbonyl-2-(R)-hydroxymethylazetidine An ice cooled solution of 2-(R)-azetidine carboxylic acid (0.400 g, 3.96 mmol, preparation as described by Miyoshi et al., *Chemistry Lett.*, 1973: 5) was allowed to react under the conditions described in Example 7a to yield the protected acid (0.237 g, 30%) which was used without further purification. This crude product was allowed to reaction under the conditions described in Example 7b to yield the title compound, which was used without further purification. MS (CDI/NH$_3$) m/e: 188 (M+H)$^+$, 205 (M+NH$_4$)$^+$. $^1$H NMR (CDCl$_3$, 300 MHz) d: 4.46–4.42 (m, 1H), 3.92–3.69 (m, 2H), 2.21–2.12 (m, 2H), 1.99–1.87 (m, 2H).

41b. 2-methyl-3-(N-t-butoxycarbonyl-2-(R)-azetidinylmethoxy)pyridine

An ice cooled solution of the compound from step 41a (0.151 g, 0.81 mmol) was allowed to react with 2-methyl-3-hydroxypyridine (0.092 g, 0.85 mmol) under the conditions of Example 2a, except that DEAD was replaced by di-t-butyl azodicarbonate, to yield the title compound (0.125 g, 55%). MS (DCI/NH$_3$) m/e: 279 (M+H)$^+$. $^1$H NMR (CDCl$_3$, 300 MHz) δ: 8.11 (dd J=4.6, 1.3 Hz, 1H), 7.20–7.10 (m, 2H), 4.54–4.53 (m, 1H), 4.36–4.35 (m, 1H), 4.09 (dd, J=10.0, 2.6 Hz, 1H), 3.95–3.88 (m, 2H), 2.55 (s, 3H), 2.42–2.30 (m, 2H), 1.40 (s, 9H).

41c. 2-methyl-3-(2-(R)-azetidinylmethoxy)pyridine dihydrochioride

The compound from step 41b (0.121 g, 0.435 mmol) was treated with saturated ethanolic HCl (5 mL). After 16 hr, the volatiles were removed in vacuo, and the dihydrochloride was recrystallized (EtOH/Et$_2$O) to yield the title compound (0.098 g, 90%) as a hygroscopic oil. MS (DCI/NH$_3$) m/e: 179 (M+H)$^+$. $^1$H NMR (D$_2$O, 300 MHz) δ: 8.16 (d, J=5.5 Hz, 1H), 7.79 (d, J=8.5 Hz, 1H), 7.62 (dd, J=8.5, 5.5 Hz, 1H), 5.00 (m, 1H), 4.57–4.47 (m, 2H), 4.24–4.12 (m, 2H), 2.78–2.71 (m, 2H). Anal. calc. for $C_{10}H_{16}ClN_2O.0.5H_2O$: C, 46.17 H, 6.59 N, 10.77. Found: C, 45.93; H, 6.61 N, 10.63. $[\alpha]_D^{23}$ –5.85° (c=0.21 in MeOH).

EXAMPLE 42

3-((1-methyl-2-(R)-piperidinyl)methoxy)pyridine dihydrochloride 42a. (R)-N-(t-butyloxycarbonyl)pipecolinic acid A 10.44 g (80.9 mmol) sample of (R)-pipecolinic acid, previously resolved according to Hemingway, R. J., *J. Pharm. Pharmac.*, 20, 87–91, (1968), was dissolved in 70 mL of dioxane and 40 mL of H$_2$O, and 40 mL of 1M K$_2$CO$_3$ and 39 mL of di-t-butyldicarbonate were added. The reaction was stirred at room temperature for 16 hr, then an additional 10 mL of di-t-butyldicarbonate and 40 mL of 1M K$_2$CO$_3$ were added and the reaction continued for another 24 hr. The solvents were removed on a rotary evaporator, 10% citric acid solution was added to the residue, and the mixture was extracted with CHCl$_3$. The extract was dried over MgSO$_4$, filtered and concentrated to give the title product as a white solid. MS: 247 (M+NH$_4$)$^+$, 230 (M+H)$^+$, 191 (M-C$_4$H$_8$+NH$_4$)$^+$.

42b. 1-methyl-2-(R)-hydroxymethylpiperidine

To the compound from step 42a (1.06 g, 4.63 mmol) in anhydrous THF (10 mL) under N2 at 0° C. was added LiAlH$_4$ (1M in diethyl ether; 15 mL). The reaction was stirred for 16 hr, and additional LiAlH$_4$ (8 mL) was added. The reaction was quenched by the addition of sodium sulfate decahydrate (60 mg), filtered through celite and washed with THF. The combined organics were concentrated in vacuo to yield the title compound as an oil (0.552 g, 93%). This material was carried forward without further purification. MS (CDI/NH$_3$) m/e: 130 (M+H)$^+$. 1H NMR (CDCL$_3$, 300 MHz) δ: 3.86 (dd, 1H), 3.41 (dd, 1H), 2.88 (m, 1H), 2.32 (s, 3H), 2.18 (m, 2H), 1.98 (m, 1H), 1.76 (m, 1H), 1.62 (m, 2H), 1.51 (m, 1H), 1.29 (m, 1H).

42c. 3-((1-methyl-2-(R)-piperidinyl)methoxy)pyridine dihydrochloride

The compound from step 42b (553 mg, 4.28 mmol) was allowed to react with 3-bromopyridine (0.43 mL, 4.50 mmol), cuprous bromide (0.165 g, 0.86 mmol), triphenylphosphine (0.449 g, 1.7 mmol) and potassium carbonate (0.592 g, 4.28 mmol). The reaction mixture was heated to 90° C. and stirred for 120 hr, then cooled to 25° C., acidified with HCl (1.5 M; 35 mL) and washed with ethyl acetate (4×50 mL). The aqueous layer was basified with saturated aqueous potassium carbonate, and the product was extracted with chloroform (6×50 mL), dried (MgSO$_4$) and concentrated in vacuo to an oil. The crude product was purified by chromatography on silica gel (CH$_2$Cl$_2$/EtOAc/MeO/HNH$_4$OH 50:50:4:1) to yield the free base of the title compound (0.048 g). The amine was treated as in example 1b to yield the title compound as a hygroscopic semisolid (0.024 g, 2%). MS (DCI/NH$_3$) m/e: 207 (M+H)$^+$. $^1$H NMR (D$_2$O, 300 MHz) δ: 8.37–8.29 (m, 2H), 7.66 (dd, J=8.45, 1.5 Hz, 1H), 7.59–7.57 (m, 1H), 4.63 (dt, J=14.5, 2.4 Hz, 2H), 4.8 (dd, J=11.9, 1.8 Hz, 1H), 3.58–3.53 (m, 2H), 3.20 (m, 1H), 2.93 (s, 3H), 2.05–1.60 (m, 5H). Anal. calc. for $C_{12}H_{20}Cl_2N_2O.2.0\,H_2O$: C, 45.72; H, 7.67; N, 8.89. Found: C, 45.82; H, 7.93; N, 8.84. $[\alpha]_D^{23}$ –1.14° (c=0.71 in MeOH).

EXAMPLE 43

2-chloro-3-(2-(S)-pyrrolidinylmethoxy)pyridine dihydrochloride 43a. 2-chloro-3-(2-(S)-pyrrolidinylmethoxy)pyridine (S)-1-t-Butoxycarbonyl-2-pyrrolidinemethanol (2.01 g, 10.0 mmol, prepared in Example 15a) and 5chloro-3-pyridinol (1.454 g, 11.0 mmol, Aldrich Chemical Co.). were allowed to react in the presence of triphenylphosphine and DEAD as described in Example 2a. The crude product was hydrolyzed with 10% HCl at room temperature for 0.5 hours. The solution was made basic with NaHCO3, then extracted with ethyl acetate. After removal of the solvent, the residue was purified by chromatography over silica gel to give 166.5 mg of the title product. MS (DCI/NH$_3$) m/e: 213 (M+H)$^+$ and 215 (M+H)$^+$. $^1$H NMR (CDCl$_3$, 300 MHz) δ: 7.99 (d, J=5.1 Hz, 1H), 7.25 (d, J=8.5 Hz, 1H), 7.20 (dd, J=5.1, 8.5 Hz), 1H), 4.08–4.01 (m, 1H), 4.40–3.94 (m, 1H), 3.69–3.58 (m, 1H), 3.15–2.98 (m, 2H), 2.07–1.61 (m, 4H).

43b. 2-chloro-3-(2-(S)-pyrrolidinylmethoxy)pyridine dihydrochloride

The compound from step 43a was treated with HCl and the product isolated as described in Example 1b, affording 155 mg of the title compound. mp 203–205° C. MS (DCI/NH$_3$) m/e: 213 (M+H)$^+$ and 215 (M+H)$^+$. $^1$H NMR (D$_2$O, 300 MHz) d: 8.00 (d, J=5.1 Hz, 1H), 7.56 (d, J=8.5 Hz, 1H), 7.43 (dd, J=5.1 Hz, 1H), 4.58–4.50 (m, 1H), 4.32–4.24 (m, 1H), 4.24–4.12 (m, 1H), 3.51–3.37 (m, 2H), 2.37–1.95 (m, 4H). Anal. Calc. for C$_{10}$H$_{13}$N$_2$OCl.2.00 HCl: C, 42.06; H, 5.29; N, 9.81; Found C, 42.28; H, 4.95; N, 10.02. [α]$_D^{25}$=+18.3° (c=1.01, MeOH).

EXAMPLE 44

3-(1-methyl-2-(S)-pyrrolidinylmethoxy)-5-trifluoromethylpyridine dihydrochloride 44a. 3-(1-methyl-2-(S)-pyrrolidinylmethoxy)-5-trifluoromethylpyridine (S)-(–)-1-Methyl-2-pyrrolidinemethanol (Aldrich Chemical Co., 0.5 g, 4.34 mmol) was reacted with 3-chloro-5-trifluoromethylpyridine according to the method of Example 3, except using DMF in place of THF as solvent and reducing reaction time to less than 2 hours. The solvent was removed, the residue dissolved in ethyl acetate, and the product purified by chromatography over silica gel to give 170 mg of the title compound. MS (DCI/NH$_3$) m/e: 261 (M+H)$^+$. $^1$H NMR (CDCl$_3$, 300 MHz) δ: 8.50 (d, J=0.6 Hz, 1H), 8.49 (d, J=3.0 Hz, 1H), 7.41 (dd, J=0.6 Hz, 1H), 8.49 (d, J=3.0 Hz, 1H), 7.41 (dd, J=0.6, 3.0 Hz, 1H), 4.12–3.96 (m, 2H), 3.21–3.10 (m, 1H), 2.80–2.65 (m, 1H), 2.51 (s, 3H), 2.44 (m, 1H), 2.14–1.73 (m, 4H).

44b. 3-(1-methyl-2-(S)-pyrrolidinylmethoxy)-5-trifluoromethylpyridine dihydrochloride The compound from step 43a was treated with HCl and the product isolated as described in Example 1b, affording the title compound. mp 243–246° C. MS (DCI/NH$_3$) m/e: 261 (M+H)$^+$. $^1$H NMR (D$_2$O, 300 MHz) δ: 8.58 (d, J=0.6 Hz, 1H), 8.55 (d, J=3.0 Hz, 1H), 7.82 (dd, J=0.6, 3.0 Hz, 1H), 4.60 (dd, J=11, 2.9 Hz, 1H), 4.43 (dd, J=10.6, 6.2 Hz, 1H), 4.05–3.93 (m, 1H), 3.82–3.72 (m, 1H), 3.37–3.22 (m, 1H), 3.06 (s, 3H), 2.49–2.05 (m, 4H). Anal. Calc. for C$_{12}$H$_{16}$N$_2$OF$_3$Cl.0.50 H$_2$O: C, 45.76; H, 5.28; N, 8.89; Found C, 45.51; H, 5.25; N, 9.16. [α]$_D^{25}$=–1.1° (c=0.57, MeOH).

EXAMPLE 45

3-(2-(S)-pyrrolidinylmethoxy)-6-chloropyridine dihydrochloride 45a. 3-(1-t-butoxycarbonyl-2-(S)-pyrrolidinylmethoxy)-6-chloropyidine A sample of (S)-1-t-butoxycarbonyl-2-pyrrolidinemethanol (1.12 g, 5.568 mmol, prepared as in Example 15a above) and 600 mg (4.64 mmol) of 2-chloro-5-hydroxypyridine were reacted with triphenylphosphine and DEAD (5.88 mmol each) in 20 mL of THF according to the procedure of Example 14.a MS (DCI/NH$_3$) m/e: 313/315 (M+H)$^+$. $^1$H NMR (CDCl$_3$, 300 MHz) δ: 8.09 (dd, J=2.1, 2.1 Hz, 1H), 7.24–7.19 (m, 2H), 4.234.05 (m, 2H), 4.03–3.83 (m, 1H), 3.45–3.31 (m, 1H), 2.08–1.84 (m, 4H), 1.47 (s, 9H).

45b. 3-(2-(S)-pyrrolidinylmethoxy)-6-chloropyridine

The compound from step 45a was treated with TFA as in Example 14b to afford 140 mg of the title compound. MS (DCI/NH$_3$) m/e: 213/215 (M+H)$^+$ and 230/232 (M+NH$_4$)$^+$. $^1$H NMR (CDCl$_3$, 300 MHz) δ: 8.06 (d, J=3.0 Hz, 1H), 7.28 (dd, J=8.8, 3.0 Hz, 1H), 7.23 (d, J=8.8 Hz, 1H), 4.14–4.10 (m, 2H), 3.83–3.73 (m, 1H), 3.22–3.15 (m, 2H), 2.20–1.75 (m, 4H).

45c. 3-(2-(S)-pyrrolidinylmethoxy)-6-chloropyridine dihydrochloride

The compound from step 45b was treated with HCl in ether according to Example 14c to afford the title compound. mp 136–138° C. MS (DCI/NH$_3$) m/e: 213/215 (M+H)$^+$ and 230/232 (M+NH$_4$)$^+$. $^1$H NMR (D$_2$O, 300 MHz) δ: 8.13 (d, J=3.0 Hz, 1H), 7.52 (dd, J=8.8, 3.0 Hz, 1H), 7.45 (d, J=8.8 Hz, 1H), 4.46 (dd, J=11.0, 3.0 Hz, 1H), 4.24 (dd, J=11.0, 5.8 Hz, 1H), 4.17–4.06 (m, 1H), 3.46–3.27 (m, 2H), 2.35–1.90 (m, 4H). Anal. Calc. for C$_{10}$H$_{15}$N$_2$OCl$_3$: C, 42.06; H, 5.29; N, 9.81; Found C, 42.30; H, 4.96; N, 9.98. [α]$_D^{25}$=+12.7° (c=0.60, MeOH).

EXAMPLE 46

4-methyl-3-((1-methyl-2-(S)-pyrrolidinyl)methoxy) pyridine dihydrochloride 46a. 4-methyl-3-((1-methyl-2-(S)-pyrrolidinyl)methoxy) pyridine To a 330 mg sample of 4-methyl-3-(2-(S)-pyrrolidinylmethoxy)pyridine (from Example 27 above) was added a solution of formic acid/formaldehyde (1:2, 2 mL). The mixture was heated at reflux for 5 hours, and the volatiles were removed by evaporation. The residue was dissolved in 1 mL of 20% NaOH. The solution was extracted with CH$_2$Cl$_2$ (3×), then the organic layer was dried (Na$_2$SO$_4$) and concentrated. The crude product was purified by chromatography over silica gel to afford 295 mg of the title compound. MS (DCI/NH$_3$) m/e: 207 (M+H)$^+$. $^1$H NMR (CDCl$_3$, 300 MHz) δ: 8.17 (s, 1H), 8.12 (d, J=5.5 Hz, 1H), 7.06 (d, J=5.5 Hz, 1H), 4.07 (dd, J=3.3, 10.6 Hz, 1H), 3.98 (dd, J=7.4, 10.6 Hz, 1H), 3.15–3.08 (m, 1H), 2.76–2.68 (m, 1H), 2.53 (s, 3H), 2.38–2.25 (m, 1H), 2.26 (s, 3H), 2.12–1.67 (m, 4H).

46a. 4-methyl-3-((1-methyl-2-(S)-pyrrolidinyl)methoxy) pyridine dihydrochloride

The compound from step 46b was treated with HCl in ether according to Example 14c to afford the title compound. mp 217–219° C. MS (DCI/NH$_3$) m/e: 207 (M+H)$^+$. $^1$H NMR (D₂O, 300 MHz) δ: 8.34 (s, 1H), 8.32 (d, J=5.5 Hz, 1H), 7.76 (d, J=5.5 Hz, 1H), 4.65 (dd, J=3.3, 10.6 Hz, 1H), 4.44 (dd, J=7.4, 10.6 Hz, 1H), 4.08–4.00 (m, 1H), 3.83–3.77 (m, 1H), 3.33–3.22 (m, 1H), 3.10 (s, 3H), 2.49 (s, 3H), 2.50–2.06 (m, 4H). Anal. Calc. for $C_{12}H_{20}N_2OCl_2$: C, 51.62; H, 7.22; N, 10.03; Found C, 51.60; H, 7.02; N, 9.74. $[\alpha]_D^{25}$=+6.3° (c=1.80, MeOH).

EXAMPLE 47

34 (trans-4-methoxy-1-methyl-2-(S)-pyrrolidinyl) methoxy)pyridine dihydrochloride 47a. 3-((trans-1-Methyl-4-methoxy-5-oxo-2(S)-pyrrolidinyl)methoxy)pyridine A 250 mg (1.13 mmol) sample of 3-(trans-1-methylt-4-hydroxy-5-oxo-2(S)-pyrrolidinylmethoxy)pyridine (from Example 23a) was dissolved in 5 mL of anhydrous THF and brought to 0° C. NaH ((80% dispersion in mineral oil), 90 mg, 2.26 mmol) was added and the reaction mixture was allowed to warm to room temperature with stirring. After stirring at room temperature for 30 minutes methyl iodide (0.178 mL) and tetrabutylammonium iodide were added, and the reaction mixture was stirred for 16 hours. The reaction was quenched by the addition of water, and the mixture was extracted with chloroform. The extract was dried over $MgSO_4$, filtered and concentrated. The solvent was removed, and the residue was purified by column chromatography on silica gel, eluting with 10:1 chloroform-:methanol to afford 242 mg of the title compound.

47b. 3-((4-methoxy-1-methyl-2-(S)-pyrrolidinyl)methoxy)pyridine

To the compound from step 47a above, dissolved in 4 mL of THF, was added 3.39 mL of $BH_3$ and the mixture was heated at reflux for 2 hours. Methanol was added to the reaction mixture and evaporated The residue was dissolved in anhydrous ethanol. Cesium fluoride was added, and the resultant solution was stirred under reflux for 16 hr. Evaporation of the solvent provided a white solid which was purified on a silica gel column. MS ($DCI/NH_3$) m/e: 223 (M+H)⁺. ¹H NMR (CDCl₃, 300 MHz) δ: 8.34 (m, 1H), 8.23 (t, J=3 Hz, 1H), 7.22 (m, 1H), 3.93–4.10 (m, 3H), 3.44–3.54 (m, 1H), 3.32 (s, 3H), 3.03–2.87 (m, 1H), 2.51 (s, 3H), 2.44–2.33 (m, 1H), 2.11–1.92 (m, 2H).

47c. 3-((4-methoxy-1-methyl-2-(S)-pyrrolidinyl)methoxy) pyndine dihydrochloride

The compound from step 47b was treated with HCl in ether according to Example 14c to afford the title compound. MS ($DCI/NH_3$) m/e: 223 (M+H)⁺. ¹H NMR (D₂O, 300 MHz) δ: 8.61 (m, 1H), 8.43 (d, 1H, J=5.32 Hz), 7.91 (m, 1H), 7.74 dd, 1H, J=5.34, 8.1 Hz), 4.61–4.53 (m, 2H), 4.14 (m, 1H), 3.98 (m, 1H), 3.81 (m, 1H), 3.30 (s, 3H), 3.22 (m, 1H), 2.96 (s, 3H), 2.37 (m, 1H), 2.01 (m, 1H). Anal. Calc. for $C_{12}H_{20}N_2O_2Cl_2$: C, 48.82; H, 6.82; N, 9.49; Found C, 48.56; H, 6.88; N, 9.43.

EXAMPLE 48

3-((cis-4-hydroxymethyl-1-methyl-2-(S)-pyrrolidinyl)methoxy)pyridine dihydrochloride 48a. 3-(1-methyl-4-hydroxymetyl-oxo-2(S)-pyrrolidinylmethoxy)pyridine A 4.12 g (20 mmol) sample of 3-((1-methyl-5-oxo-2-(S)-pyrrolidinyl)methoxy)pyridine, from Example 22b above, was dissolved in 50 mL of dry THF and cooled to −78° C. To this solution was added 14.67 mL (22 mmol) of LDA, and the mixture was stirred for 1 hour. The temperature of the reaction mixture was warmed to −20° C. to −10° C., and 4 g (200 mmol) of paraformaldehyde was added. The reaction was stirred at this temperature for 3 hours. The reaction was quenched by addition of H₂O, and the mixture was taken to dryness. The residue was repeatedly triturated with ethyl acetate to dissolve the product. The solvent was removed, and the residue was purified on a silica gel column, eluting with 100:) to 100: 10 CHCl₃:methanol, to afford 2.90 g of the title compound.

48b. 3-((4hydroxymethyl-1-methyl-2-(S)-pyrrolidinyl) methoxy)pyridine

A 401 mg (2 mmol) sample of 3-(1-methyl4-hydroxymethyl-5-oxo-2(S)-pyrrolidinylmethoxy)pyridine, from step 48a above, was dissolved in 6 mL of THF and 6 mL of 1M $B_2H_6$ was added. The reaction mixture was heated at reflux for 2 hours, then stirred at room temperature for 15 minutes after methanol was added. The solvent was removed under pressure, and the residue was dissolved in 4 mL of ethanol. The this solution was added 251 mg of CsF, and the reaction mixture was heated at reflux for 16 hours. The solvent was removed, and the residue was purified on a column of silica gel, eluting with 100:5 to 10:1 chloroform:methanol 78 mg of a mixture of cis and trans product. cis compound: MS ($DCI/NH_3$) m/e: 223 (M+H)⁺. ¹H NMR (CDCl₃, 300 MHz) δ: 8.32 (m, 1H), 8.23 (t, 1H, J=3 Hz), 7.21 (m, 1H), 4.16–3.94 (m, 2H), 3.77–3.54 (m, 2H), 3.09–3.01 (m, 1H), 2.88–2.64 (m, 1H), 2.58–2.47 (m, 1H), 2.46 (m, 1H), 2.46 (s, 1H), 2.38–2.29 (m, 1H), 1.98–1.81 (m, 1H). trans compound: MS ($DCI/NH_3$) m/e: 223 (M+H)⁺. ¹H NMR (CDCl₃, 300 MHz) d: 8.33 (m, 1H), 8.23 (m, 1H), 7.23 (m, 1H), 4.20–3.96 (m, 2H), 3.74–3.59 (m, 2H), 3.42–3.26 (m, 1H), 2.97–2.83 (m, 1H), 2.54 (s, 1H), 2.48–2.23 (m, 1H), 2.04–1.80 (m, 1H).

48c. 3-((cis-4-hydroxymethyl-1-methyl-2-(S)-pyrrolidinyl) methoxy)pyridine dihydrochloride The cis-compound from step 48b was treated with HCl in ether according to Example 14c to afford the title compound. MS ($DCI/NH_3$) m/e: 223 (M+H)⁺. ¹H NMR (D₂O, 300 MHz) δ: 8.49 (d, 1H, J=3 Hz), 8.39 (dd, 1H, J=1, 5 Hz), 8.0 (m, 1H), 7.82 (dd, 1H, J=5, 8 Hz), 4.68–4.60 (m, 1H), 4.54–4.43 (m, 1H), 4.10–3.95 (m, 1H), 3.76–3.60 (m, 2H), 3.50–3.40 (m, 1H), 3.40 (s, 3H), 2.90–2.77 (m, 1H), 2.60–2.46 (m, 1H), 2.35–2.13 (m, 1H, 1.98–1.85 (m, 1H). Anal. Calc. for $C_{12}H_{20}N_2O_2Cl_2$: C, 48.82; H, 6.82; N, 9.49; Found C, 48.82; H, 6.68; N, 9.26.

EXAMPLE 49

3-((4-methoxymethyl-1-methyl-2-(S)-pyrrolidinyl) methoxy)pyridine dihydrochloride 49a. 3-((4-methoxymethyl-1-methyl-5-oxo-2-(S)-pyrrolidinyl)methoxy)-pyridine A 327 mg (139 mmol) sample of 3-(1-methyl-4-hydroxymethyl-5-oxo-2(S)-pyrrolidinylmethoxy)pyridine, prepared as in Example 48a above, was dissolved in 13 mL of anhydrous THF, 111 mg (2.77 mmol) of NaH was added, and the mixture was stirred for 30 minutes at room temperature. To this solution was added 258 mL (4.17 mmol) of methyl iodide and 256 mg of tetrabutylammonium iodide, and the reaction was stirred at room temperature for 2 hours.

The reaction was quenched by the addition of water, and the mixture was extracted with chloroform. The extract was dried over $MgSO_4$, filtered and concentrated. The solvent was removed, and the residue was purified by column chromatography on silica gel, eluting with 10:1 chloroform:methanol to give 314 mg of the title compound. MS (DCI/$NH_3$) m/e: 251 (M+H)$^+$. $^1$H NMR (CDCl$_3$, 300 MHz) δ: 8.37–8.25 (m, 2H), 7.35–7.25 (m, 2H), 4.18–4.0 (m, 2H), 3.99–3.84 (m, 1H), 3.73–3.58 (m, 2H), 3.37 (s, 2H), 3.36 (s, 1H), 3.05 (s, 1H), 2.95 (s, 1H), 2.94 (s, 1H), 2.90–2.63 (m, 1H), 2.49–2.24 (m, 2H).

49b. 3-((4-methoxymethyl-1-methyl-2-(S)-pyrrolidinyl)methoxy)pyridine

The compound from step 49a (314 mg) was dissolved in 3 mL of THF, 11.5 mL of BH$_3$ was added, and the mixture was heated at reflux for 2 hours. The reaction was quenched by addition of methanol, and the mixture was stirred for 30 minutes. The solvent was removed, and the solvent was removed, and the residue was purified by column chromatography on silica gel, eluting with 20:1 chloroform:methanol. The purified intermediate was dissolved in 4 mL of THF, 125 mg of BH$_3$ and 123 mg of CsF were added, and the reaction was heated at reflux for 2 hours. The solvent was removed, and the residue was purified by column chromatography on silica gel, eluting with 1:10 chloroform:methanol to give 69 mg of the title compound. MS (DCI/NH$_3$) m/e: 236 (M+H)$^+$. $^1$H NMR (CDCl$_3$, 300 MHz) δ: 8.32 (m, 1H, 8.23 (t, J=3 Hz, 1H), 7.25–7.20 (m, 2H), 4.18–3.95 (m, 2H), 3.30–3.48 (m, 3H), 3.36 (s, 3H), 3.13–3.03 (m, 1H), 2.7–2.40 (m, 4H), 2.33–2.16 (m, 1H), 2.06–1.81 (m, 2H).

49c. 3-((4-methoxmethyl-1-methyl-2-(S)-pyrrolidinyl)methoxy)pyridine dihydrochloride The compound from step 49b was treated with HCl in ether according to Example 14c to afford the title compound. mp 158–160° C. MS (DCI/NH$_3$) m/e: 237 (M+H)$^+$. $^1$H NMR (D$_2$O, 300 MHz) δ: 8.51 (d, 1H, J=2.9 Hz), 8.41 (d, 1H, J=5.0 Hz), 8.05 (m, 1H), 7.87 (dd, 1H, J=5.2, 8.5 Hz), 4.64 (dd, 1H, J=2.9, 11 Hz), 4.54–4.7 (m, 1H), 4.10–3.96 (m, 1H), 3.94–3.83 (m, 1H), 3.70–3.46 (m, 2H), 3.39 (s, 3H), 3.06 (s, 2H), 3.04 (s, 1H), 2.98–2.72 (m, 1H), 2.47–2.13 (m, 2H), 1.96–1.84 (m, 1H). Anal. Calc. for C$_{13}$H$_{20}$N$_2$O$_2$.1.8 HCl: C, 51.71; H, 7.28; N, 9.28; Found C, 51.70; H, 7.14; N, 9.17.

EXAMPLE 50

3-((trans-4-cyanomethyl-1-methyl-2-(S)-pyrrolidinyl)methoxy)pyridine dihydrochloride 50a. 3-((trans-4-methanesulfonyloxymethyl-1-methyl-2-(S)-pyrrolidinyl)methoxy)pyridine To a 386 mg (1.84 mmol) sample of 3-(trans-1-methyl-4-hydroxymethyl-2(S)-pyrrolidinylmethoxy)pyridine (from Example 48a above) dissolved in 12 mL of methylene chloride were added 262 μL (3.38 mmol) of methanesulfonyl chloride, 470 μL of triethylamine and a catalytic amount of DMAP, and the reaction mixture was stirred for 5 hours at room temperature. The reaction was quenched with water, the product extracted from the mixture, the solvent removed, and the product purified by column chromatography on silica gel, eluting with 20:1 chloroform:methanol to afford 320 mg of the title compound.

50b. 3-(trans-4-cyanomethyl-1-methyl-2-(S)-pyrrolidinyl)methoxy)pyridine

A 132 mg sample of the compound from step 50a above was dissolved 4 mL of a 6:1 solution of DMF:H$_2$O, 240 mg of NaCN was added, and the reaction mixture was stirred at 95° C. for 16 hours. The solvent was removed, and the residue was purified by column chromatography on silica gel, eluting with 10:1 chloroform:methanol to afford 62 mg of the title compound. MS (DCI/NH$_3$) m/e: 232 (M+H)$^+$. $^1$H NMR (CDCl$_3$, 300 MHz) δ: 8.34 (m, 1H), 8.28 (m, 1H), 7.30–7.20 (m, 2H), 4.28–4.06 (m, 2H), 3.05–2.72 (m, 5H), 2.65–2.52 (br s, 3H), 2.42–2.25 (m, 1H), 2.23–2.0 (m, 2H).

50c. 3-((trans-4-cyanomethyl-1-methyl-2-(S)-pyrrolidinyl)methoxy)pyridine dihydrochloride The compound from step 50b was treated with HCl in ether according to Example 14c to afford the title compound. mp 203–205° C. MS (DCI/NH$_3$) m/e: 232 (M+H)$^+$. $^1$H NMR (D$_2$O, 300 MHz) δ: 8.48 (d, 1H, J=3 Hz), 8.38 (dd, 1H, J=1.0, 5.2 Hz), 7.96 (m, 1H), 7.80 (dd, 1H, J=5.1, 8.8 Hz), 4.64 (dd, 1H, J=2.9, 11.4 Hz), 4.49 (dd, 1H, J=5.2, 11.1 Hz), 4.24–4.10 (m, 1H), 4.05–3.91 (m, 1H), 3.09 (s, 3H), 3.25–3.02 (m, 2H), 3.0–2.8 (m, 2H), 2.53–2.40 (m, 1H), 2.38–2.23 (m, 1H). Anal. Calc. for C$_{13}$H$_{17}$N3O.1.7 HCl: C, 53.24; H, 6.43; N, 14.33; Found C, 53.21; H, 6.07; N, 14.36.

EXAMPLE 51

3-((1-methyl-2-(R)-pyrrolidinyl)methoxy-6-chloropyridine dihydrochloride 51a. 3-((1-methyl-2-(R)-pyrrolidinyl)methoxy)-6-chloropyridine A 376 mg (1.2 mmol) sample of 3-((1-t-butoxycarbonyl-2-(R)-pyrrolidinyl)methoxy)-6-chloropyridine, prepared from (R)-1-t-butoxycarbonyl-2-pyrrolidinemethanol by the procedure described in Example 45a above, was treated with paraformaldehyde and formic acid for 2 hours as described in Example 16a above. The crude material was purified by column chromatography on silica gel, eluting with 20:1 chloroform:methanol to afford 219 mg of the title compound. MS (DCI/NH$_3$) m/e: 225/227 (M+H)$^+$. $^1$H NMR (CDCl$_3$, 300 MHz) δ: 8.07 (s, 1H), 7.25–7.18 (m, 2H), 4.02 (dd, J=9.1, 5.4 Hz, 1H), 3.93 (dd, J=9.1, 5.4 Hz, 1H), 3.17–3.11 (m, 1H), 2.71–2.67 (m, 1H), 2.49 (s, 3H), 2.38–2.29 (m, 1H), 2.10–1.98 (m, 1H), 1.91–1.68 (m, 3H). [α]$^{25}$$_D$=+64.5° (c=1.1, CHCl$_3$).

51b. 3-((1-methyl-2-(S)-pyrrolidinylmethoxy)-6-chloropyridine hydrochloride

The compound from step 51a was treated with HCl in ether according to Example 14c to afford the title compound. mp 120–122° C. MS (DCI/NH$_3$) m/e: 225/227 (M+H)$^+$. $^1$H NMR (D$_2$O, 300 MHz) d: 8.13 (d, J=8.8 Hz, 1H), 7.54 (dd, J=8.8, 3.0 Hz, 1H), 7.47 (d, J=8.8 Hz, 1H), 4.52 (dd, J=11.4, 3.2 Hz, 1H), 4.35 (dd, J=11.4, 5.9 Hz, 1H), 3.98–3.90 (m, 1H), 3.78–3.70 (m, 1H)(, 3.33–32.4 (m, 1H), 3.03 (s, 3H), 2.42–2.37 (m, 1H), 2.25–2.07 (m, 3H). Anal. Calc. for C$_{11}$H$_{16}$N$_2$OCl$_2$: C, 50.20; H, 6.13; N, 10.64; Found C, 50.01; H, 6.19; N, 10.55.

EXAMPLE 52

3-(2-(S)-azetidinylmethoxy)-6-chloropyridine dihydrochloride 52a. 3-((1-t-Butyloxycarbonyl-2-(S)-azetidinyl)methoxy)-6-chloropyridine A 950 mg (5.1 mmol) sample of 1-t-butyloxycarbonyl-2-(S)-azetidinemethanol, prepared as in Example 7b above, and 550 mg (4.25 mmol) of 2-chloro-5-hydroxypyridine were reacted with triphenylphosphine and DEAD (5.1 mmol each) in 20 mL of THF according to the procedure of Example 14a, to give 1.09 g of the title compound. MS (DCI/NH$_3$) m/e: 299/301 (M+H)$^+$. $^1$H NMR (DMSO-d$_6$, 300 MHz) δ: 8.14 (d, J=3.3 Hz, 1H), 7.48 (dd, J=8.8, 3.3 Hz, 1H), 7.37 (d, J=8.8 Hz, 1H), 4.47–4.42 (m, 1H), 4.36 (dd, J=11.0, 4.4 Hz, 1H), 4.20 (dd, J=11.0, 3.3 Hz, 1H), 3.77 (t, J=7.7 Hz, 2H), 2.36–2.29 (m, 1H), 2.19–2.12 (m, 1H), 1.36 (s, 9H). [α]$_D^{25}$=−67.3° (c=1.1, CHCl$_3$).

52b. 3-(2-(S)-azetidinylmethoxy)-6-hloropyridine dihydrochloride

A 1.02 g sample of the compound from step 52a was stirred with 10 mL of 4.5 N HCl at room temperature for 30 minutes. The solvent was removed, and the residue was recrystallized from methanol/ether, to yield after drying 340 mg of the title compound. mp 113–115° C. MS (DCI/NH$_3$) m/e: 299/301 (M+H)$^+$. $^1$H NMR (D$_2$O, 300 MHz) δ: 8.15 (d, J=3.0 Hz, 1H), 7.57 (dd, J=8.9, 3.0 Hz, 1H), 7.47 (d, J=8.9 Hz, 1H), 4.98–4.89 (m, 1H), 4.42 (d, J=4.4 Hz, 2H), 4.19–402 (m, 2H), 2.68 (q, J=8.5 Hz, 2H). Anal. Calc. for C$_9$H$_{13}$N$_2$OCl$_3$: C, 39.80; H, 4.82; N, 10.32; Found C, 40.12; H, 4.84; N, 10.35.

EXAMPLE 53

2-methyl-3-(1-methyl-2-(S)-pyrrolidinylmethoxy) pyridine dihydrochloride

To a 658 mg (2.25 mmol) sample of 2-methyl-3-((1-t-butoxycarbonyl-2-(S)-pyrrolidinyl)methoxy)pyridine, from Example 17a above, was added 3 mL of a solution of formic acid and formaldehyde (1:2), and the reaction mixture was stirred at 80° C. for 3 hours. The reaction was quenched with water and sat. K$_2$CO$_3$, and the mixture was extracted with methylene chloride. The extract was dried over MgSO$_4$, reduced in volume, and the residue was purified by chromatography on silica gel, eluting with 5% to 10% methanol in chloroform. Removal of the solvent, and conversion of the residue into the salt with HCl in ehter gave the title compound. mp 202–205° C. MS (DCI/NH$_3$) m/e: 193 (M+H)$^+$. $^1$H NMR (D$_2$O, 300 MHz) δ: 2.08–2.27 (m, 3H), 2.43–2.48 (m, 1H), 2.55 (s, 3H), 3.09 (s, 3H), 3.31 (br s, 1H), 3.76 (br s, 1H), 4.04 (br s, 1H), 4.36 (dd, 1H, J=7, 11 Hz), 4.58 (dd, 1H, J=3. 11 Hz), 7.50 (dd, 1H, J=5, 8.5 Hz), 7.65 (dd, 1H, J=1, 5 Hz), 8.12 (d, 1H, J=1, 5 Hz). Anal. Calc. for C$_{12}$H$_{18}$N$_2$O.2.00.HCl: C, 51.62; H, 7.22; N, 10.03; Found C, 51.47; H, 7.35; N, 9.80. [α]$_D^{25}$=+6.38° (c=0.02, MeOH).

EXAMPLE 54

3-((1-methyl-2-(R)-pyrrolidinyl)methoxy-5-trifluoromethylpyridine hydrochloride 54a. 3-((1-methyl-2-(R)-pyrrolidinyl)methoxy)-5-trifluoromethylpyridine (R)-1-methyl-2-pyrrolidinemethanol (Aldrich Chemical Co.) was dissolved in 8 mL of DMF and stirred under N$_2$, then 240 mg of NaH (80% dispersion in mineral oil) was added. The reaction mixture was stirred fifteen minutes, and 363 mg of 3-chloro-5-trifluoromethylpyridine (2.0 mmol) was added. The reaction mixture was stirred at 50° C. for 16 hours. The volatiles were removed under vacuum, and the residue was purified by chromatography on silica gel, eluting with 2:1 ethyl acetate:hexane to give 336 mg of the title product. MS (DCI/NH$_3$) m/e: 261 (M+H)$^+$. $^1$H NMR (CDCl$_3$, 300 MHz) δ: 8.50 (d, J=0.6 Hz, 1H), 8.49 (d, J=3.0 Hz, 1H), 7.41 (dd, J=0.6, 3.0 Hz, 1H), 4.12–3.96 (m, 2H), 3.21–3.10 (m, 1H), 2.80–2.65 (m, 1H), 2.51 (s, 3H), 2.44–2.30 (m, 1H), 2.13–1.73 (m, 4H).

54b. 3-((1-methyl-2-(R)-pyrrolidinyl)methoxy)-5-trifluoromethylpyridine hydrochloride The compound from step 54b was treated with HCl in ether according to Example 14c to afford 282 mg of the title compound. mp 246–248° C. MS (DCI/NH$_3$) m/e: 261 (M+H)$^+$. $^1$H NMR (D$_2$O, 300 MHz) δ: 8.58 (d, J=0.6 Hz, 1H), 8.56 (d, J=3.0 Hz, 1H), 7.83 (dd, J=0.6, 3.0 Hz, 1H), 4.60 (dd, J=11.0, 2.9 Hz, 1H), 4.33 (dd, J=10.6, 6.2 Hz, 1H), 4.05–3.93 (m, 1H), 3.82–3.72 (m, 1H), 3.37–3.22 (m, 1H), 3.06 (s, 3H), 2.49–2.05 (m, 4H). Anal. Calc. for C$_{12}$H$_{16}$N$_2$OF$_3$Cl: C, 47.99; H, 5.50; N, 9.29; Found C, 48.07; H, 5.40; N, 9.29. [α]$_D^{25}$=+5.0° (c=1.00, methanol).

EXAMPLE 55

6-chloro-3-((1-methyl-2-(S)-pyrrolidinyl)methoxy) pyridine dihydrochloride 55a. 6-chloro-3-((1-methyl-2-(S)-pyrrolidinyl)methoxy) pyridine A 625 mg sample of 3-((1-t-butoxycarbonyl-2-(S)-pyrrolidinyl)methoxy)-6-chloropyridine, prepared as in Example 45a, was treated with 2 mL of 37% parafornaldehyde and 1 mL of formic acid at reflux for 16 hours. The volatiles were removed by evaporation, and the residue was dissolved in 1 mL of 20% NaOH. The solution was extracted with CH$_2$Cl$_2$ (3×), then the organic layer was dried (Na$_2$SO$_4$) and concentrated. The crude product was purified by chromatography over silica gel, eluting with 100:1 chloroform:methanol to afford 439 mg of the title compound. MS (DCI/NH$_3$) m/e: 227/229 (M+H)$^+$. $^1$H NMR (CDCl$_3$, 300 MHz) δ: 8.09 (dd, J=2.1, 2.1 Hz, 1H), 7.24–7.21 (m, 2H), 4.02 (dd, J=11.0, 3.0 Hz, 1H), 3.93 (d, J=11.0, 5.8 Hz, 1H), 3.21–3.10 (m, 1H), 2.76–2.64 (m, 1H), 2.51 (s, 3H), 2.40–2.28 (m, 1H), 2.12–1.98 (m, 1H), 1.97–1.68 (m, 4H).

55b. 6-chloro-3-((1-methyl-2-(S)-pyrrolidinyl)methoxy) pyridine dihydrochloride

The compound from step 55b was treated with HCl in ether according to Example 14c to afford 312 mg of the title compound. mp 98–98° C. MS (DCI/NH$_3$) m/e: 227/229 (M+H)$^+$. $^1$H NMR (D$_2$O, 300 MHz) δ: 8.10 (d, J+3.0 Hz, 1H), 7.54 (dd, J=8.8, 3.0 Hz, 1H), 7.45 (d, J=8.8 Hz, 1H), 4.50 (dd, J=11.0, 3.0 Hz, 1H), 4.33 (dd, J=11.0, 5.8 Hz, 1H), 3.96–3.87 (m, 1H), 3.80–3.69 (m, 1H), 3.30–3.18 (m, 1H), 3.03 (s, 3H), 2.45–2.00 (m, 4H). Anal. Calc. for C$_{11}$H$_{15}$N$_2$OCl$_2$.0.5 H$_2$O: C, 48.49; H, 6.16; N, 10.29; Found C, 48.54; H, 6.30; N, 10. [α]$^{25}_D$=−3.9° (c=1.05, MeOH).

EXAMPLE 56

5-bromo-3-((1-methyl-2-(R)-pyrrolidinyl)methoxy) pyridine hydrochloride 56a. 5-bromo-3-((1-methyl-2-(R)-pyrrolidinyl)methoxy) pyridine (R)-1-methyl-2-pyrrolidinemethanol (430 mg, 13.74 mmol, Aldrich Chemical Co.) was dissolved in 14 mL of DMF and stirred under N$_2$, then 123.4 mg of NaH (80% dispersion in mineral oil) was added. The reaction mixture was stirred fifteen minutes, and 897.4 mg of 3,5- dibromomethylpyridine was added. The reaction mixture was stirred at 50° C. for 16 hours. The volatiles were removed under vacuum, and the residue was purified by chromatography on silica gel to give 484 mg of the title product MS (DCI/NH$_3$) m/e: 271/273 (M+H)$^+$. $^1$H NMR (CDCl$_3$, 300 MHz) δ: 8.37 (d, J=1.8, Hz, 1H), 8.26 (d, J=2.7 Hz), 1H, 7.39 (dd, J=1.8, 2.7 Hz, 1H), 4.01 (dd, J=3.3, 11.0 Hz, 1H), 3.93 (dd, J=6.9, 11.1, Hz, 1H), 3.20–3.10 (m, 1H), 3.93 (dd, J=6.9, 11.1 Hz, 1H), 3.20–3.10 (m, 1H), 2.76–2.64 (m, 1H), 2.49 (s, 3H), 2.40–2.28 (m, 1H), 2.44–2.00 (m, 4H).

56b. 5-bromo-3-(1-methyl-2-(R)-pyrrolidinyl)methoxy) pyridine hydrochloride

The compound from step 55b was treated with HCl in ether according to Example 14c to afford 362 mg of the title compound. mp 205° C. (dec). MS (DCI/NH$_3$) m/e: 271/273 (M+H)$^+$. $^1$H NMR (D$_2$O, 300 MHz) δ: 8.45 (d, J=1.5 Hz, 1H), 8.38 (d, J=2.7 Hz, 1H), 8.01 (dd, J=1.5, 2.7 Hz, 1H), 4.56 (dd, J=3.0, 11.4 Hz, 1H), 4.40 (dd, J=6.3, 11.4 Hz, 1H), 3.98–3.86 (m, 1H), 3.80–3.72 (m, 1H), 3.30–3.20 (m, 1H), 3.03 (s, 3H), 2.44–2.00 (m, 4H). Anal. Calc. for C$_{12}$H$_{16}$N$_2$OBrCl.0.18 HCl: C, 39.23; H, 5.03; N, 8.32; Found C, 39.11; H, 4.90; N, 8.32. [α]$^{25}_D$=−3.9° (c=1.05, methanol).

EXAMPLE 57

3-(1-allyl-2-(S)-pyrrolidinyl)methoxy)-5-bromopnridine dihydrochloride 57a. 1-allyl-2-(S)-pyrrolidinemethanol (S)-1-methyl-2-pyrrolidinemethanol (5.10 g, 50 mmol, Aldrich Chemical Co.) was dissolved in 50 mL of CHCl$_3$, then 5.25 mL of allyl bromide and 8.34 mL of triethylamine were added. The reaction mixture was stirred at room temperature for 2 hours, then the volatiles were removed under reduced pressure. The residue was purified by chromatography on silica gel to give 63 g of the title product. MS (DCI/NH$_3$) m/e: 142 (M+H)$^+$. $^1$H NMR (CDCl$_3$, 300 MHz) δ: 6.05–5.90 (m, 1H), 5.33–5.17 (m, 2H), 3.77–3.68 (m, 1H), 3.58–3.47 (m, 2H), 3.32–3.20 (m, 1H), 3.16–3.05 (m, 1H), 2.90–2.78 (m, 1H), 2.53–2.40 (m, 1H), 2.02–1.73 (m, 4H).

57b. 3-((1-allyl-2-(S)-pyrrolidinyl)methoxy)-5-bromopyridine

A 230 mg sample of 1-allyl-2-(S)-pyrrolidinemethanol, from step 57a above, was dissolved in 8 mL of DMF and stirred under N$_2$, then 104 mg of NaH (80% dispersion in mineral oil) was added. The reaction mixture was stirred fifteen minutes, and 489.8 mg of 3,5-dibromomethylpyridine was added. The reaction mixture was stirred at 60° C. for 4 hours. The volatiles were removed under vacuum, and the residue was purified by chromatography on silica gel to give 230 mg of the title product. MS (DCI/NH$_3$) m/e: 297/299 (M+H)$^+$. $^1$H NMR (CDCl$_3$, 300 MHz) δ: 8.28 (d, J=1.8 Hz, 1H), 8.24 (d, J+2.6 Hz, 1H), 7.48 (dd, J=1.8, 2.6 Hz, 1H), 6.02–5.88 (m, 1H), 5.30–5.12 (m, 2H), 4.15–3.90 (m, 1H), 3.96–3.82 (m, 1H), 3.60–3.43 (m, 1H), 3.23–3.05 (m, 2H), 3.03–2.90 (m, 1H), 2.45–2.32 (m, 1H), 2.10–1.95 (m, 1)H, 1.90–1.70 (m, 3H).

57c. 3-((1-allyl-2-(S)-pyrrolidinyl)methoxy)-5-bromopyridine dihydrochloride

The compound from step 57b was treated with HCl in ether according to Example 14c to afford 198 mg of the title compound. mp 183–185° C. MS (DCI/NH$_3$) m/e: 297/299 (M+H)$^+$. $^1$H NMR (D$_2$O, 300 MHz) δ: 8.43 (d, J=1.8 Hz, 1H), 8.36 (d, J=2.6 Hz), 7.94 (dd, J=1.8, 2.6 Hz, 1H), 6.04–5.92 (m, 1H), 5.64–5.57 (m, 2H), 4.58–4.48 (m, 1H), 4.42–4.36 (m, 1H), 4.12–4.02 (m, 2H), 3.94–3.88 (m, 1H), 3.76–3.64 (m, 1H), 3.36–3.25 (m, 1H), 2.43–2.31 (m, 1H), 2.22–2.00 (m, 3H). Anal. Calc. for C$_{13}$H$_{19}$N$_2$OBrCl$_2$: C, 42.19; H, 5.17; N, 7.57; Found C, 42.32; H, 5.10; N, 7.79. [α]$^{25}_D$=−14.7° (c=1.01, methanol).

EXAMPLE 58

3-(2-(R)-pyrrolidinylmethoxy)-6-chloropridine hydrochloride

Following the procedures described in Example 45 steps a–c, substituting (R)-1-t-butoxycarbonyl-2-pyrrolidinemethanol for the (S)-1-t-butoxycarbonyl-2-pyrrolidinemethanol of step 45a thereof, the title compound was prepared. mp 157–159° C. MS (DCI/NH$_3$) m/e: 213/215 (M+H)$^+$ and 230/232 (M+NH$_4$)$^+$. $^1$H NMR (D$_2$O, 300 MHz) d: 8.10 (d, J=3.0 Hz, 1H), 7.53–7.43 (m, 2H), 4.45 (dd, J=10.7, 7.7 Hz, 1H), 4.15–4.08 (m, 1H), 3.41 (t, J=7.2 Hz, 2H), 2.34–1.88 (m, 4H). Anal. Calc. for C$_{10}$H$_{14}$Cl$_2$N$_2$O.0.3 HCl: C, 46.18; H, 5.54; N, 10.77; Found C, 46.35; H, 5.51; N, 10.66.

EXAMPLE 59

3-((1-methyl-2-(S)-azetidinyl)methoxy)-6-methylpyridine dihydrochloride 59a. 3-((1-BOC-2-(S)-azetidinyl)methoxy)-6-methylpyridine A 3.74 g (20 mmol) sample of 1-t-butyloxycarbonyl-2-(S)-azetidinemethanol, prepared as in Example 7b above, and 3.27 g (30 mmol) of 2-methyl-5-hydroxypyridine were reacted with triphenylphosphine and DEAD (30 mmol each) in 100 mL of THF according to the procedure of Example 14a, to give the title compound.

59b. 3-((1-methyl-2-(S)-azetidinyl)methoxy)-6-methylpyridine dihydrochloride

A 1.3 g sample of the compound from step 59a above was dissolved in 6 mL of methylene chloride, the solution was cooled to 0° C., and 4 mL of TFA was added. The reaction mixture was stirred at 0° C. for 3 hours, then poured into a satd solution of K$_2$CO$_3$. The organic layer was separated, the aqueous layer extracted with additional methylene chloride, the organics combined, and the solvent removed. The residue was dissolved in ethanol, the solution was cooled to 0° C., and excess NaCNBH$_3$ was added. Two mL of HCHO were added, the pH was adjusted with acetic acid, using bromocresol as an indicator, and the reaction mixture was stirred for 16 hours. The reaction was quenched by pouring it into satd K$_2$CO$_3$ solution. The mixture was extracted with methylene chloride, the extract was dried over MgSO$_4$, and the solvent was removed. The residual oil was purified by chromatography on silica gel, eluting with 100:1 to 95:5 CHCl$_3$:methanol containing 0.5% NH$_4$OH. This compound was treated with HCl in ether according to Example 14c to afford 362 mg of the title compound. MS (DCI/NH$_3$) m/e: 193 (M+H)$^+$. $^1$H NMR (D$_2$O, 300 MHz) δ: 8.33 (d, J=2.2 Hz, 1H), 7.92 (dd, J=2.6, 8.8 Hz, 1H), 7.66 (d, J=8.8 Hz, 1H), 7.66 (d, J=8.8 Hz, 1H), 4.87–4.77 (m, 1H), 4.57–4.44 (m, 2H), 4.33–4.23 (m, 1H), 4.01 (q, J=9.6 Hz, 1H), 3.00 (s, 3H), 2.73–2.61 (m, 2H), 2.64 (s, 3H). Anal. Calc. for $C_{11}H_{16}N_2O$.2 HCl.0.4 $H_2O$: C, 49.88; H, 6.84; N, 10.56; Found C, 48.25; H, 6.96; N, 10.28.

EXAMPLE 60

3-((cis-1-methyl-3-propyl-2-pyrrolidinyl)methoxy) pyridine dihydrochloride 60a. cis-1-BOC-3-propyl-2-pyrrolidinemethanol A 400 mg (1.6 mmol) sample of 1-BOC-3-propyl-2-carboxylic acid methyl ester (prepared according to Chung et al., *J. Org. Chem.*, 55:270–275 (1990)) was dissolved in 12 mL of THF and cooled to 0° C. To this solution was added 3.0 mL of 1M LAH, and the reaction was stirred at 0° C. for 30 minutes. The reaction was quenched by sequential addition of 0.11 mL of $H_2O$, 0.11 mL of 40% NaOH and 3.00 mL of H2O, and the mixture was stirred for 30 minutes. The mixture was filtered, and the filtrate was concentrated. The residue was purified by chromatography on silica gel to give 240 mg of the title compound.

60b. 3-((cis-1-BOC-3-propyl-2-pyrrolidinyl)methoxy) pyrindine

A 220 mg (0.96 mmol) sample of cis-1-BOC-3-propyl-2-pyrrolidinemethanol, prepared as in Example 60a above, and 137 g (1.44 mmol) of 3-hydroxypyridine were reacted with triphenylphosphine and DEAD (1.44 mmol each) in 10 mL of THF according to the procedure of Example 14a, to give 190 mg of the title compound. MS (DCI/$NH_3$) m/e: 321 (M+H)$^+$. $^1$H NMR (CDCl$_3$, 300 MHz) δ: 8.29 (s, 1H), 8.19 (m, 1H), 7.27 (m, 1H), 7.21 (m, 1H), 4.33 (q, 1H), 4.18–3.80 (m, 2H), 3.52–3.2 (m, 2H), 2.32–2.20 (m, 1H), 2.05–1.94 (m, 1H), 1.80–1.73 (m, 1H), 1.58–1.23 (m, 4H), 1.48 (s, 9H), 0.92 (m, 3H).

60c. 3-((cis-1-methyl-3-propyl-2-p rrolidinyl)methoxy pyridine

A 100 mg (0.31 mmol) sample of 3-(cis-1-BOC-3-propyl-2-pyrrolidinylmethoxy)pyridine, from step 60b above, was treated with 1.9 mL of formic acid and 3.83 mL of 37% HCHO at 67° C. for 16 hr. The reaction was quenched by pouring it into satd $K_2CO_3$ solution. The mixture was extracted with methylene chloride, the extract was dried over MgSO$_4$, and the solvent was removed to give 70 mg of the title compound. MS (DCI/NH$_3$) m/e: 235 (M+H)$^+$. $^1$H NMR (CDCl$_3$, 300 MHz) d: 8.34 (m, 1H), 8.22 (m, 1H), 7.21 (m, 2H), 4.50 (m, 1H), 3.95 (m, 1H), 3.12 (m, 1H), 2.82–2.72 (m, 1H), 2.52 (s, 3H), 2.38–2.22 (m, 2H), 2.02–1.91 (m, 1H), 1.60–1.35 (m, 4H), 1.30–1.23 (m, 3H), 0.82 (t, 3H).

60d. 3-((cis-1-methyl-3-propyl-2-pyrrolidinyl)methoxy) pyridine dihydrochloride

The compound from step 60c was treated with HCl in ether according to Example 14c to afford the title compound. MS (DCI/NH$_3$) m/e: 235 (M+H)$^+$. $^1$H NMR (D$_2$O, 300 MHz) δ: 8.51 (d, J=2.9 Hz, 1H), 8.42 (d, J=5.5 Hz, 1H), 4.63 (m, 1H), 4.50 (m, 1H), 2.04 (m, 1H), 3.83 (m, 1H), 3.18 (m, 1H), 3.07 (s, 3H), 2.78 (m, 1H), 2.42–2.30 (m, 1H), 1.58–1.28 (m, 4H), 0.9 (t, J=7.0, 3H). Anal. Calc. for $C_{14}H_{22}N_2O$.2 HCl.1 $H_2O$: C, 51.69; H, 8.06; N, 8.61; Found C, 51.67; H, 7.79; N, 8.19. $[α]^{25}_D$=+16.5° (c=1.01, methanol).

EXAMPLE 61

3-((cis-3-propyl-2-pyrrolidinyl)methoxy)pyridine dihydrochloride 61a. 3-((cis-3-propyl-2-pyrrolidinyl)methoxy)pyridine A 160 mg (0.5 mmol) sample of 3-(cis-1-BOC-3-propyl-2-pyrrolidinylmethoxy)pyridine, from step 60b above, was dissolved in 2 mL of methylene chloride and stirred with 1 mL of TFA for 16 hours at room temperature. The solvent was removed under vacuum, and the residue was adjusted to pH 8 with NaHCO$_3$. The mixture was extracted with methylene chloride, and the extract was dried over MgSO$_4$ The residue was purified by chromatography on silica gel, eluting with 10:2:0.2 CHCl$_3$.methanol:ammonium hydroxide, to give 60 mg of the title product. MS (DCI/NH$_3$) m/e: 221 (M+H)$^+$. $^1$H NMR (CDCl$_3$, 300 MHz) δ: 8.33 (m, 1H), 8.24 (m, 1H), 7.22 (m, 2H), 4.10 (m, 1H), 4.00 (m, 1H), 3.69 (m, 1H), 3.24 (m, 1H), 3.07 (m, 1H), 2.33 (m, 1H), 2.07 (m, 1H), 1.65 (m, 1H), 1.39 (m, 4H), 0.92 (m, 3H).

61a. 3-((cis-3-propyl-2-pyrrolidinyl)methoxy)pyridine dihydrochloride

A 120 mg sample of the compound from step 61a was treated with HCl in ether according to Example 14c to afford 120 mg of the title compound. mp 183–185° C. MS (DCI/NH$_3$) m/e: 221 (M+H)$^+$. $^1$H NMR (D$_2$O, 300 MHz) δ: 8.34 (s,1H), 8.25 (d, J=4.04, 1H), 7.61 (m, 1H), 7.52 (m, 1H), 4.45 (dd, J=3.7, 10.7 Hz, 1H), 4.27 (m, 1H), 4.16 (m, 1H), 3.54 (m, 1H), 3.35 (m, 1H), 2.55 (m, 1H), 2.30 (m, 1H), 1.92 (m, 1H), 1.57–1.3 (m, 4H), 0.92 (t, J=6.9 Hz, 3H). Anal. Calc. for $C_{13}H_{20}N_2O$.1.6 HCl.0.3 $H_2O$: C, 54.97; H, 7.88; N, 9.85; Found C, 55.37; H, 7.48; N, 9.43.

EXAMPLE 62

3-(2-(R)-azetidinylmethoxy)pyridine dihydrochloride 62a. 1-BOC-azetidine-2-(R)-carboxylic acid A 4.98 g (19.50 mmol) sample of the 1-(p-toluenesulfonyl)azetidine-2-(R)-carboxylic acid (prepared according to the procedure of Miyoshi et al., *Chem. Lett.*, 1973:5) was suspended in 100 mL of liq. NH$_3$ at −78° C., and sodium metal was added over a period of 1 hour until a blue color persisted. The reaction mixture was stirred for 16 hours, slowly allowing the reaction mixture to rise to room temperature. Excess K$_2$CO$_3$ was added (3.23 g), followed by 250 mL of THF and 10 mL of isopropanol. To this solution was added 25 mL of H$_2$O and 538 mL (23.9 mmol) of di-t-butyl dicarbonate, and the reaction mixture was stirred for 18 hours. The reaction was quenched by addition of 100 mL of 10% NaOH, and the mixture was extracted with ether. The aqueous layer was acidified to pH 1 with 10% HCl, and this solution-was extracted with methylene chloride. The methylene chloride extract was dried over MgSO$_4$ and concentrated to afford 1.92 g of the title compound as an oil.

62b. 1-BOC-2-(R)-azetidinemethanol

To an ice-cooled solution of the product of Example 62a (1.9 g, 9.44 mmol) in tetrahydrofuran (100 ml) was added boranelTHF complex (1 M, 42.5 mL, 42.5 mmol) under nitrogen. The eaction was gradually warmed to room temperature and stirred for 18 hours, then quenched by addition of 75 mL of 10% NH$_4$Cl. The mixture was extracted with methylene chloride, which was washed with 10% HCl and brine, dried over and concentrated to afford 1.18 g of the title product as an oil.

62c. 1-BOC-2-(R)-azetidinylmethoxy)pyridine

A 1.10 g (5.87 mmol) sample of 1-BOC-2-(R)-azetidinemethanol, prepared in step 62b above, and 588 g (5.87 mmol) of 3-hydroxypyridine were reacted with triphenylphosphine and DEAD (7.05 mmol each) in 100 mL of THF according to the procedure of Example 14a, to give the title compound.

62d. 2-(R)-azetidinylmethoxy)pyridine

The compound from step 62c above (147 mg) was treated with 5 mL of hydrogen chloride saturated ethanol for 4 hours. The solvents were removed under vacuum to give the title compound. MS (DCI/NH$_3$) m/e 165 (M+H)$^+$, 182 (M+NH$_4$)$^+$. $^1$NMR (DMSO, 300 MHz) δ: 2.36–2.64 (m, 2H), 3.84–4.02 (m, 2H), 4.37–4.53 (m, 2H), 4.69–4.81 (m, 1H), 7.54–7.62 (m, 1H), 7.65–7.73 (m, 1H), 8.34 (dd, 1H, 8.49 (d, 1H), 9.14 (m, 2H). Anal. calc. for C$_9$H$_{12}$N$_2$O.2.0 HCl.0.2 CH$_2$OH: C, 45.83; H, 6.22; N, 11.37. Found: C, 45.86; H, 6.12; N, 11.17.

EXAMPLE 63

3-((1-methyl-2-(R)-azetidinyl)methoxy)pyridine dihydrochloride

A 142 mg (0.537 mmol) sample of 1-BOC-2-(R)-azetidinylmethoxy)pyridine, from Example 62c above, was treated with 5 mL of formic acid and 5 mL of 37% HCHO at reflux for 14 hr. The reaction was quenched by addition of H$_2$O. The mixture was adjusted to pH 7 with NaHCO$_3$ and extracted with methylene chloride, the extract was dried over MgSO$_4$, and the solvent was removed to give the title compound, which was converted to the salt as in Example 62d above. MS (DCI/NH$_3$) m/e 179 (M+H)$^+$, 196 (M+NH$_4$)$^+$. $^1$NMR (DMSO, 300 MHz) δ: 2.33–2.48 (m, 2H), 2.87, 2.88 (two s, 3H), 3.79–3.96 (m, 1H), 3.99–4.13 (m, 1H), 4.44–4.67 (m, 2H), 4.67–4.81 (m, 1H), 7.67–7.73 (m, 1H), 7.81–7.89 (m, 1H), 8.41 (dd, 1H), 8.58 (d, 1H), 10.71 (br m, 1H). Anal. calc. for C$_9$H$_{12}$N$_2$.2.0 HCl.0.6 H$_2$O.0.2 CH$_2$OH: C, 46.87; H, 6.99; N, 10.12. Found: C, 46.77; H, 7.01; N, 9.93.

EXAMPLE 64

4methyl-3-(2-(S)-azetidinylmethoxy)pyridine dihydrochloride

A 0.82 g (4.4 mmol) sample of 1-BOC-2-(S)-azetidinemethanol, prepared as in Example 7b above, and 0.48 g (4.4 mmol) of 4methyl-3-hydroxypyridine, prepared as in Example 27b above, were reacted with triphenylphosphine and DEAD (5.28 mmol each) in 15 mL of THF according to the procedure of Example 14a. The BOC group was removed as in Example 14b to give the free base of the title compound. The base was converted to the salt as in Example 62d above. mp 149–152° C. MS (DCI/NH$_3$) m/e 179 (M+H)$^+$, 196 (M+NH$_4$)$^+$. $^1$NMR (D$_2$O, 300 MHz) δ: 8.28 (br s, 1H), 8.24 (m, 1H), 7.59 (d, J=5.2 Hz, 1H), 4.98 (m, 1H), 4.53 (m, 2H), 4.16 (m, 2H), 2.75 (d, J=8.4 Hz, 2H), 2.46 (s, 3H). Anal. calc. for C$_{10}$H$_{16}$Cl$_2$N$_2$O.0.3 HCl: C, 45.83; H, 6.27; N, 10.69. Found: C, 45.90; H, 6.45; N, 10.34.

EXAMPLE 65

5-bromo-3-(2-(S)-pyrrolidinylmethoxy)pyridine dihydrochloride 65a. 5-bromo-3-methoxypyridine To a suspension of 12 g of 3,5-dibromopyridine and 40 g of 60% NaH in DMF was added 4.05 mL of methanol, and the reaction mixture was stirred for 4 hours at room temperature and 1 hour at 60° C. The DMF was removed under reduced pressure, and the residue was taken directly to the next step. MS (DCI/NH$_3$) m/e 188/190 (M+H)$^+$, 205/207 (M+NH$_4$)$^+$. $^1$H NMR (CDCl$_3$, 300 MHz) δ: 8.32 (d, J=1.8 Hz, 1H, 8.27 (d, J=2.6 Hz, 1H), 7.42 (dd, J=1.8, 2.6 Hz, 1H), 3.88 (s, 3H).

65b. 5-bromo-3-hydroxypyridine

The compound from the previous step was heated at relux with 60 mL of HBr for 16 hours. The reaction was quenched with excess NaHCO3, and the basic mixture was extracted with ethyl acetate, and the extract was dried over Na2SO4. The solvent was removed, and the residue was chromatographed on silica gel, eluting with 10% methanol in chloroform. MS (DCI/NH$_3$) m/e 174/176 (M+H)$^+$, 191/193 (M+NH$_4$)$^+$. $^1$H NMR (CDCl$_3$, 300 MHz) δ: 8.27 (d, J=1.8 Hz, 1H), 8.23 (d, J=2.6 Hz, 1H), 7.44 (dd, J=1.8, 2.6 Hz).

65c. 5-bromo-3-(1-BOC-2-(S)-pyrrolidinylmethoxy) pyridine

A 332 mg (1.2 mmol) sample of 1-BOC-2-(S)-azetidinemethanol, prepared as in Example 7b above, and 240 mg (1.38 mmol) of 5-bromo-3-hydroxypyridine, prepared as in Example 65b above, were reacted with triphenylphosphine and DEAD (1.2 mmol each) in 5 mL of THF according to the procedure of Example 14a, to give 355 mg of the tide compound. MS (DCI/NH$_3$) m/e 357/359 (M+H)$^+$, 374/376 (M+NH$_4$)$^+$. $^1$H NMR (CDCl$_3$, 300 MHz) δ: 8.28 (d, J=1.8 Hz, 1H), 8.24 (d, J=2.6 Hz, 1H), 7.44 (dd, J=1.8, 2.6 Hz, 1H), 8.24 (d, J=2.6 Hz, 1H), 7.44 (dd, J=1.8, 2.6 Hz, 1H, 4.21–4.05 (m, 2H), 4.03–3.92 (m, 1H, 3.48–3.82 (m, 2H), 2.10–1.80 (m, 4H), 1.47 (s, 9H).

65d. 5-bromo-3-(2-(S)-pyrrolidinylmethoxy)pyridine dihydrochloride

The BOC group was removed from the compound of 65c as in Example 14b to give the free base of the title compound. The base was converted to the salt as in Example 62d above. mp 168–170° C. MS (DCI/NH$_3$) m/e 257/259 (M+H)$^+$, 274/276 (M+NH$_4$)$^+$. $^1$H NMR (D$_2$O, 300 MHz) δ: 8.39 (d, J=1.8 Hz, 1H), 8.32 (d, J=2.6 Hz, 1H), 7.90 (dd, J=1.8, 2.6 Hz, 11H), 4.50 (dd, J=11, 3.6 Hz, 1H), 4.28 (dd, J=11, 7.7 Hz, 1H), 4.16–4.08 (m, 1H), 3.41 (t, J=7.2 Hz, 2H). Anal. Calc. for C$_{10}$H$_{14}$N$_2$OBrCl.0.9 HCl: C, 36.80; H, 4.60; N, 8.58; Found C, 36.93; H, 4.52; N, 8.58. [α]$^{25}_D$=+8.65° (c=1.04, methanol).

EXAMPLE 66

3-(2-(S)-pyrrolidinylmethox)-5-trifluoromethylpridine dihydrochloride 66a. 3-benzyloxy-5-trifluoromethylpyridine To a 3.63 g (20 mmol) sample of 3-chloro-5-trifluoromethylpyridine dissolved in 15 mL of DMF and cooled to 0° C. was added 960 mg of NaH (60%), 2.07 mL of benzyl alcohol was added slowly. The reaction mixture was stirred for 2 hours at 40° C. The solvent was then evaporated in vacuo and the mixture diluted with chloroform, washed with saturated NaHCO$_3$ and a brine solution. The organic layer was then dried over MgSO$_4$. The resulting crude material was purified by flash chromatography on silica gel to give the title product. MS (DCI/NH$_3$) m/e 154 (M+H)$^+$. $^1$H NMR (CDCl$_3$, 300 MHz) d: 8.56 (d, J=1.8 Hz, 1H), 8.47 (d, J=0.9 Hz, 1H), 7.51 (dd, J=1, 0.9 Hz, 1H).

66b. 3-hydroxy-5-trifluoromethylpyridine

The product from step a above (1.95 g) was dissolved in 10 mL of methanol and hydrogenated over Pd/C (5%, 97.5 mg) at 1 atm H2 for 16 hours. The catalyst was removed, and the solvent was evaporated. The residue was purified by flash chromatography on silica gel to give the title compound. MS (DCI/NH$_3$) m/e 163 (M+H)$^+$, 181 (M+NH$_4$)$^+$. $^1$H NMR (CDCl$_3$, 300 MHz) δ: 8.57 (d, J=1.8 Hz, 1H), 8.51 (d, J=0.9 Hz, 1H), 7.4–7.25 (m, 6h), 5.17 (s, 2H).

66c. 3((1-BOC-2-(S)-pyrrolidinyl)methoxy)-5-trifluoromethylpyridine

A 333 mg (1.20 mmol) sample of 1-BOC-2-(S)-azetidinemethanol, prepared as in Example 7b above, and 230 mg (1.30 mmol) of 3-hydroxy-5-trifluoromethylpyridine, from step 66b above, were reacted with triphenylphosphine and DEAD (1.2 mmol each) in 5 mL of THF according to the procedure of Example 14a, to give 360 mg of the title compound. MS (DCI/NH$_3$) m/e 347 (M+H)$^+$. $^1$H NMR (CDCl$_3$, 300 MHz) δ: 8.50 (s, 1H), 8.48 (s, 1H), 7.46 (s, 1H), 4.28–3.90 (m, 3H), 3.48–3.84 (m, 2H), 2.12–1.87 (m, 4H).

66d. 3-(2-(S)-pyrrolidinylmethoxy)-5-trifluoromethylpyridine dihydrochloride

The BOC group was removed from the compound of 66c as in Example 14b to give the free base of the title compound. The base was converted to the salt as in Example 62d above. mp 158–161° C. MS (DCI/NH$_3$) m/e 247 (M+H)$^+$, 264 (M+NH$_4$)$^+$. $^1$H NMR (D$_2$O, 300 MHz) δ: 8.60 (d, J=0.6 Hz, 1H), 8.55 (d, J=3.0 Hz, 1H), 7.88 (dd, J=0.6, 3.0 Hz, 1H), 4.54 (dd, J=10.6, 3.7 Hz, 1H), 4.32 (dd, J=10.6, 7.7 Hz, 1H), 4.20–4.11 (m, 1H), 3.42 (t, J=6.9 Hz, 2H), 2.35–1.90 (m, 4H). Anal. Calc. for C$_{11}$H$_{14}$N$_2$OClF$_3$: C, 41.40; H, 4.74; N, 8.78; Found C, 41.38; H, 4.57; N, 8.77. [α]$^{25}_D$=+13.0° (c=0.50, methanol).

EXAMPLE 67

3-(2-(S)-azetidinylmethoxy)-5-bromopyridine dihydrochloride 67a 3-((1-BOC-2-(S)-azetidinyl)methoxy)-5-bromopyridine A 619.3 mg (3.31 mmol) sample of 1-BOC-2-(S)-azetidinemethanol, prepared as in Example 7b above, and 480 mg (2.76 mmol) of 5-bromo-3-hydroxypyridine, from Example 65b above, were reacted with triphenylphosphine and DEAD (3.31 mmol each) in 10 mL of THF according to the procedure of Example 14a, to give 887 mg of the title compound. MS (DCI/NH$_3$) m/e 243/246 (M+H)$^+$, 260/262 (M+NH$_4$)$^+$. $^1$H NMR (CDCl$_3$, 300 MHz) δ: 8.35–8.25 (br, 2H), 7.44 (s, 1H), 4.55–4.47 (m, 1H), 4.39–4.29 (m, 1H), 4.16–4.10 (m, 1H), 3.98–3.85 (m, 2H), 2.42–2.33 (m, 2H), 1.42 (s, 9H).

67b. 3-(2-(S)-azetidinylmethoxy)-5-bromopyridine dihydrochloride

The BOC group was removed from the compound of 67a by hydrolysis with 4M HCl in dioxane to give the free base of the title compound. The base was converted to the salt as in Example 62d above, followed by recrystallization from methanol/ether. mp 163–165° C. MS (DCI/NH$_3$) m/e 243/246 (M+H)$^+$, 260/262 (M+NH$_4$)$^+$. $^1$H NMR (D$_2$O, 300 MHz) δ: 8.36 (d, J=1.8 Hz, 1H), 8.32 (d, J=2.6 Hz, 1H), 7.84 (dd, J=1.8, 2.6 Hz, 1H), 4.98–4.90 (m, 1H), 4.43 (d, J=4.0 Hz, 2H), 4.20–4.02 (m, 2H), 2.67 (q, J=8.5 Hz, 2H). Anal. calc. for C$_9$H$_{13}$N$_2$OBrCl$_2$: C, 34.21; H, 4.15; N, 8.86. Found: C, 34.18; H, 4.17; N, 8.89. [α]$^{25}_D$=−5.1° (c=0.57, methanol).

EXAMPLE 68

3-((1-methyl-2-(S)-azetidinyl)methoxy)-5-bromopyridine dihydrochloride 68a. 3-((1-methyl-2-(S)-azetidinyl)methoxy)-5-bromopyridine A 480 mg sample of the free base of 3-(2-(S)-azetidinylmethoxy)-5-bromopyridine, from Example 67 above, was dissolved in 4 mL of acetic acid treated with 1 mL of 37% HCHO and 500 mg of NaBH$_3$CN at 0° C. for 4 hr. The solvents were removed under reduced pressure. The residue was basified with NaHCO$_3$ solution. The mixture was extracted with methylene chloride, the extract was dried over MgSO$_4$, and the solvent was removed. The residue was purified by chromatography on silica gel, eluting with 200:1 and 100:1 chloroform:methanol to give 68 mg of the title compound. MS (DCI/NH$_3$) m/e: 257/259 (M+H)$^+$. $^1$H NMR (CDCl$_3$, 300 MHz) δ: 8.28 (d, J=1.9 Hz, 1H), 8.26 (d, J=2.6 Hz, 1H), 7.38 (dd, J=1.9, 2.6 Hz, 1H), 4.02 (d, J=6.3 Hz, 2H), 3.51–3.44 (m, 1H), 3.43–3.37 (m, 1H), 2.93–2.84 (m, 1H), 2.41 (s, 3H), 2.13–2.03 (m, 2H).

68b. 3-((1-methyl-2-(S)-azetidinyl)methoxy)-5-bromopyridine dihdrochloride

The compound from step 60c was treated with HCl in ether according to Example 14c to afford the title compound. mp 160–162° C. MS (DCI/NH$_3$) m/e: 257/259 (M+H)$^+$. $^1$H NMR (D$_2$O, 300 MHz) δ: 8.34 (d, J=1.9 Hz, 1H), 8.31 (d, J=2.6 Hz, 1H), 7.78 (dd, J=1.9, 2.6 Hz, 1H), 4.85–4.74 (m, 1H), 4.49 (dd, J=11.8, 2.9 Hz), 4.40 (dd, J=11.0, 7.4 Hz, 1H), 4.27 (m, 1H), 4.00 (q, J=10.3 Hz, 1H), 2.99 (s, 3H), 2.74–2.55 (m, 2H). Anal. Calc. for C$_{10}$H$_{15}$N$_2$OBrCl$_2$: C, 36.39; H, 4.58; N, 8.49; Found C, 36.48; H, 4.56; N, 8.70. [α]$^{25}_D$=−16.8° (c=0.51, methanol).

EXAMPLE 69

3-(2-(R)-pyrrolidinylmethoxy)-5-trifluoromethylpyridine dihydrochloride 69a. 3-(1-BOC-2-(R)-pyrrolidinylmethoxy)-5-trifluoromethylpyridine A 332.9. mg (1.56 mmol) sample of (R)-1-t-butoxycarbonyl- 2-pyrrolidinemethanol and 224.9 mg (1.30 mmol) of 3-hydroxy-5-trifluoromethylpyridine were reacted with triphenylphosphine and DEAD (1.56 mmol each) in 5 mL of THF according to the procedure of Example 14a, to give 386 mg of the title compound. MS (DCI/NH$_3$) m/e 347 (M+H)$^+$. $^1$H NMR (CDCl$_3$, 300 MHz) δ: 8.50 (s, 1H), 8.48 (s, 1H), 7.46 (s, 1H), 4.28–3.90 (m, 3H), 3.48–3.84 (m, 2H), 2.12–1.87 (m, 4H), 1.47 (s, 9H).

69a. 3-(2-(R)-pyrrolidinylmethoxy-5-trifluoromethylpyridine dihydrochloride

A 380 mg sample of the compound from step 69a above was dissolved in 5 mL of dioxane and treated with 4 M HCl in dioxane. The salt was collected, washed and dried, to afford 129 mg of the title compound. mp 169–171° C. MS (DCI/NH$_3$) m/e 347 (M+H)$^+$. $^1$H NMR (D$_2$O, 300 MHz) δ: 8.60 (d, J=0.6 Hz, 1H), 8.55 (d, J=3.0 Hz, 1H), 7.88 (dd, J=0.6, 3.0 Hz, 1H), 4.54 (dd, J=10.6, 3.7 Hz, 1H), 4.32 (dd, J=10.6, 7.7 Hz, 1H), 4.20–4.11 (m, 1H), 3.42 (t, J=6.9 Hz, 2H), 2.35–1.90 (m, 4H). Anal. Calc. for C$_{11}$H$_{14}$N$_2$OF$_3$Cl.0.7 HCl: C, 42.87; H, 4.81; N, 9.09; Found C, 42.96; H, 4.55; N, 9.05. [α]$^{25}$$_D$=−9.2° (c=0.52, MeOH).

EXAMPLE 70

3-(2-(S)-azetidinylmethoxy)-5-trifluoromethylpyridine dihydrochloride 70a. 3-((1-BOC-2-(S)-azetidinyl)methoxy)-5-trifluoromethylpyridine A 771.9.3 mg (4.13 mmol) sample of 1-t-BOC-2-(S)-azetidinemethanol, prepared as in Example 7b above, and 560 mg (3.44 mmol) of 3-hydroxy-5-trifluoromethylpyridine, from Example 66b above, were reacted with triphenylphosphine and DEAD (4.13 mmol each) in 15 mL of THF according to the procedure of Example 14a, to give 683 mg of the title compound. MS (DCI/NH$_3$) m/e 333 (M+H)$^+$. $^1$H NMR (CDCl$_3$, 300 MHz) δ: 8.54 (d, 1.8 Hz, 1H), 8.51 (d, J=0.9 Hz, 1H), 7.93 (dd, J=0.9, 1.8 Hz, 1H), 4.59–4.50 (m, 1H), 4.94–4.86 (m, 1H), 4.22–4.17 (m, 1H), 3.90 (t, J=7.3 Hz, 2H), 2.43–2.27 (m, 2H), 1.43 (s, 9H).

70b. 3-(2-(S)-azetidinylmethoxy)-5-trifluoromethylpyridine dihydrochloride

A 680 mg sample of the compound from step 69a above was dissolved in 5 mL of dioxane and treated with 1.13 mL of 4M HCl in HCl in dioxane at 0° C. for 1.5 hours. The salt was collected, washed and dried, to afford 60 mg of the title compound. mp 154–156° C. MS (DCI/NH$_3$) m/e 233 (M+H)$^+$, 250 (M+NH$_4$)$^+$. $^1$H NMR (D$_2$O, 300 MHz) δ: 8.61 (d, 0.9 Hz, 1H), 8.60 (d, J=1.8 Hz, 1H), 7.93 (dd, J=0.9, 1.8 Hz, 1H), 5.04–4.95 (m, 1H), 4.51 (d, J=4.1 Hz, 2H), 4.22–4.04 (m, 2H), 2.70 (q, J=8.4 Hz, 2H). Anal. Calc. for C$_{10}$H$_{11}$N$_2$OF$_3$.1.8 HCl: C, 40.33; H, 4.33; N, 9.41; Found C, 40.09; H, 4.37; N, 9.35. [α]$^{25}$$_D$=−3.3° (c=0.52, MeOH).

EXAMPLE 71

5-n-butyl-3-((1-methyl-2-(S)-pyrrolidinyl)methoxy) pyridine dihydrochloride

To a 1.08 g (4 mmol) sample of 5-bromo-3-((1-methyl-2-(S)-pyrrolidinyl)methoxy)pyridine, prepared as in Example 56a above, dissolved in 40 mL of dry ether and cooled to 0° C. was added 6.0 mL of n-butylmagnesium chloride and 13.0 mg of Ni(dppp)Cl, and the reaction mixture was stirred for 5 hours at room temperature. The reaction was quenched by addition of satd NH$_4$Cl, and the mixture was extracted with chloroform. The solvent was dried over MgSO4 and removed under vacuum, and the residue was purified of a column of silica gel, eluting with 100:1.25:0.025 chloroform:methanol:ammonium hydroxide. The product was converted into the title compound by treatment with HCl in ether according to Example 14c. MS (DCI/NH$_3$) m/e: 259 (M+H)$^+$. $^1$H NMR (D$_2$O, 300 MHz) δ: 8.28 (d, J=3.0 Hz, 1H), 8.24 (s, 1H), 7.80 (m, 1H), 4.58 (dd, J=11.0, 3.0 Hz, 1H), 4.42 (dd, J=11.4, 5.5 Hz, 1H), 3.96 (m, 1H), 3.77 (m, 1H), 3.32–3.23 (m, 1H), 3.05 (s, 3H), 2.78 (t, J=7.3, 2H), 2.43–2.38 (m, 1H), 2.26–2.06 (m, 3H), 1.70–1.60 (m, 2H), 1.40–1.27 (m, 2H), 0.91 (t, J=7.4 Hz, 3H). Anal. Calc. for C$_{15}$H$_{24}$N$_2$O.2 HCl.0.2 ether C, 56.46; H, 8.40; N, 8.33; Found C, 56.85; H, 8.73; N, 7.99. [α]$^{25}$$_D$=−7.30° (methanol).

EXAMPLE 72

3-((trans-4-hydroxy-2-(S)-pyrrolidinyl)methoxy) pyridine dihydrochloride

72a. CBZ-L-proline, methyl ester

A 12.5 g (47.4 mmol) sample of CBZ-L-proline (Aldrich) was dissolved in 250 mL of methanol and 1.7 mL of acetyl chloride was added. The reaction mixture was stirred at room temperature for 16 hours. The solvents were removed, the residue was dissolved in CHCl$_3$, and this solution was washed with NaHCO$_3$ solution, dried, filtered and concentrated. The residue was purified on a silica gel column, eluting with 1:1 ethyl acetate:hexane to give 14 g of the title compound.

72b. O-t-butyldimethylsilyl-CBZ-proline, methyl ester.

A 7.5 g sample of the compound from step 72a was dissolved in 140 mL of DMF and 2.2 g of imidazole was added. The solution was cooled to −23° C., and 4.84 g of t-butyldimethylsilyl chloride was added and stirred for 1 hour. The volatiles were removed under vacuum, and the residue was purified on a silica gel column, eluting with 1:2 ethyl acetate:hexane to give 8.05 g of the title compound.

72c. trans-1-CBZ-4-(t-butyldimethylsilyloxy) pyrrolidinemethanol

A 3 g sample of the compound from step 72b above was dissolved in 40 mL of THF, and cooled to 0° C. To this solution was added 18.1 mL of DIBAL, and the reaction mixture was warmed to room temperature while stirring for 3 hours. The reaction was quenched by addition of 10% H$_2$SO$_4$, and the mixture was extracted with chloroform. The extract was dried, filtered and concentrated. The residue was purified o a silica gel column, eluting with 1:2 ethyl acetate:hexane to give 3 g of the title compound.

72d. trans-3-((1-CBZ4-(t-butyldimethylsilyloxy)-2-(S)-pyrrolidinyl)methoxy)pyridine A 2.8 g (10.6 mmol) sample of 1-CBZ-4-(t-butyldimethylsilyloxy)pyrrolidinemethanol, from step 72c above, and 1.5 g (15.8 mmol) of 3-hydroxypyridine were reacted with triphenylphosphine and DEAD (15.8 mmol each) in 75 mL of THF according to the procedure of Example 14a, to give 1.35 g of the title compound.

72e. 3-((trans-4-hydroxy-2-(S)-pyrrolidinyl)methoxy) pyridine

A 1.35 g sample of the compound from step 72d above was dissolved in 9 mL of THF and 9.3 mL of tetra-(t-butyl) ammonium fluoride was added. The reaction mixture was stirred at room temperature for 16 hours, and the volatiles were removed under vacuum. The residue was purified on silica gel, eluting with 3:1 ethyl acetate:hexane, to give the title compound.

72f. 3-((trans-4-hydroxy-2-(S)-pyrrolidinyl)methoxy) pyridine dihydrochloride

A 350 mg sample of the compound from step 72e above was dissolved in 6 mL of ethanol, 35 mg of 10% Pd/C was added, and the reaction mixture was shaken under 4 atm of H$_2$ for 15 hours. The catalyst was removed by filtration, the solvent removed, and the residue was purified by chromatography on silica gel, eluting with 20:1 chloroform:methanol, to give the free base. This compound was treated with HCl in ether according to Example 14c to afford the title compound. MS (DCI/NH$_3$) m/e: 195 (M+H)$^+$, 212 (M+NH$_4$)$^+$. $^1$H NMR (D$_2$O, 300 MHz) δ: 8.46 (d, 1H, J=2.5 Hz), 8.37 (d, 1H, J=5.1 Hz), 7.93 (m, 1H), 7.90 (dd, 1H, J=5.5, 8.4 Hz), 4.60 (m, 1H), 4.41 (m, 2H), 3.52 (dd, 1H, J=3.7, 2.9 Hz), 3.43 (m, 1H), 2.15–2.35 (m, 2H). Anal. Calc. for C$_{10}$H$_{14}$N$_2$O$_2$.2.7 HCl: C, 41.04; H, 5.75; N, 9.57; Found C, 40.90; H, 5.43; N, 9.48.

EXAMPLE 73

5-methyl-3-(1-methyl-2-(S)-pyrrolidinylmethoxy) pyridine dihydrochloride 73a. 5-methyl-3-(1-methyl-2-(S)-pyrrolidinylmethoxy) pyridine A 270 mg (1 mmol) sample of 5-bromo-3-(1-methyl-2-(S)-pyrrolidinylmethoxy)-pyridine, from Example 28 above, was dissolved in 10 mL of THF, 3.25 mg of Ni(dppp)Cl was added, and the mixture was cooled to 0° C. To this solution was added 0.47 mL of methylmagnesium bromide, then the mixture was stirred at reflux for 20 hours. Another 0.2 mL of methylmagnesium bromide was added, and the reaction mixture was stirred for 2 hours. The reaction was quenched by addition of NH$_4$Cl solution, and the mixture was evaporated to dryness. The residue was partitioned between H$_2$O and CHCl$_3$, and the organic extract was dried and concentrated. The residue was purified by chromatography on silica gel, eluting with 5:1 chloroform:methanol, to give 120 mg of the title compound. MS (DCI/NH$_3$) m/e: 207 (M+H)$^+$. $^1$H NMR (CDCl$_3$, 300 MHz) δ: 8.13 (d, J=2.7 Hz, 1H), 8.05 (s, 1H), 7.03 (m, 'H), 4.04–3.89 (m, 2H), 2.66 (m, 1H), 2.48 (s, 3H), 2.32 (s, 3H), 2.35–2.26 (m, 1H), 2.09–1.98 (m, 1H), 1.92–1.68 (m, 3H).

73b. 5-methyl-3-(1-methyl-2-(S)-pyrrolidinylmethox) pyridine dihydrochloride

The compound from step 73 b above was treated with HCl in ether according to Example 14c to afford the title compound. MS (DCI/NH$_3$) m/e: 207 (M+H)$^+$. $^1$H NMR (D$_2$O, 300 MHz) δ: 8.34 (d, J=2.6 Hz, 1H), 8.28 (s, 1H), 4.62 (dd, J=11.0, 2.9 Hz, 1H), 4.46 (dd, J=11.4, 5.9 Hz, 1H), 3.98 (m, 1H), 3.76 (m, 1H), 3.27 (m, 1H), 3.05 (s, 3H), 2.50 (s, 3H), 2.41 (ni, 1H), 2.28–2.05 (m, 3H). Anal. Calc. for C$_{12}$H$_{18}$N$_2$O.2 HCl: C, 51.62; H, 7.22; N, 10.03; Found C, 51.54; H, 7.16; N, 9.79.

EXAMPLE 74

3-((trans-4-methoxy-2-(S)-pyrrolidinyl)methoxy) pyridine dihydrochloride 74a. 3-((trans-1-CBZ-4-hydroxy-2-(S)-pyrrolidinyl) methoxy)pyridine A 700 mg (1.6 mmol) sample of 3-(1-CBZ-(t-butyldimethylsilyloxy)-2-(S)-pyrrolidinylmethoxy) pyridine, prepared as in Example 72d above, was dissolved in 10 mL of THF and 5.0 mL (4.8 mmol) of 1 M tetra-n-butylammonium fluoride was added. The reaction mixture was stirred at room temperature for 2 hours, and the solvent was removed. The residue was purified on a column of silica gel, eluting with 3:1 ethyl acetate:hexane to give 466 mg of the title compound. MS (DCI/NH$_3$) m/e: 328 (M+H)$^+$. $^1$H NMR (CDCl$_{3,300}$ MHz) δ: 8.28 (s, 1H), 8.21 (m, 1H), 7.33 (s, 5H), 7.27 (m, 1H), 7.20 (m, 1H), 5.13 (s, 2H), 4.59 (m, 1H), 4.37 (m, 1H), 3.62 (m, 2H), 3.59 (m, 1H), 3.20 (m, 1H), 2.18 (m, 1H).

74b. 3-((trans-1-CBZ-4-methoxy-2-(S)-pyrrolidinylmethoxy)pyridine

A 450 mg (1.4 mmol) sample of the compound from step 74a above was dissolved in 20 mL of THF, and 168 mg (4.2 mmol) of NaH, 180 mg (0.49 mmol) of tetra-n-butylammonium iodide and 0.173 mL of methyl iodide were added. The reaction mixture was stirred at room temperature for 16 hours, and the solvent was removed. The residue was purified on a column of silica gel, eluting with 1:1 to 3:1 ethyl acetate:hexane to give 210 mg of the title compound.

74c. 3-((trans-4-methoxy-2-(S)-pyrrolidinyl)methoxy-2-pyridine dihydrochloride

A 158 mg sample of the compound from step 74b above was dissolved in methanol and hydrogenated in the presence of 15 mg of 5% Pd/C catalyst at 1 atm of H$_2$ for 16 hours. The catalyst was removed by filtration, and the solvent was removed under pressure to leave 60 mg of free base. This compound was treated with HCl in ether according to Example 14c to afford 45 mg of the title compound. MS (DCI/NH$_3$) m/e: 209 (M+H)$^+$. $^1$H NMR (D$_2$O, 300 MHz) δ: 8.52 (d, J=2.6 Hz, 1H), 8.43 (d, J=5.2 Hz, 1H), 8.13 (dd, J=8.9, 1.9 Hz, 1H), 7.94 (dd, J=8.9, 5.5, 1H), 4.64 (dd, J=10.7, 2.9 Hz, 1H), 4.46–4.30 (m, 3H), 3.62–3.48 (m, 2H), 3.38 (s, 3H), 2.46 (dd, J=14.3, 6.8, 1H), 2.21–2.11 (m, 1H). Calc. for C$_{11}$H$_{16}$N$_2$O$_2$.2 HCl: C, 46.99; H, 6.45; N, 9.96; Found C, 47.06; H, 6.34; N, 9.81. [α]$^{25}_D$+32.9° (c=1.0, MeOH).

EXAMPLE 75

5-ethyl-3-(1-methyl-2-(S)-pyrrolidinylmethoxy) pyridine dihydrochloride 75a. 5-ethyl-3-(1-methyl-2-(S)-pyrrolidinylmethoxy) pyridine A 542 mg (2 mmol) sample of 5-bromo-3-(1-methyl-2-(S)-pyrrolidinylmethoxy)-pyridine, from Example 28 above, was dissolved in 10 mL of THF, 6.6 mg of Ni(dppp)Cl was added, and the mixture was cooled to 0° C. To this solution was added 0.6 mL of methylmagnesium bromide, then the mixture was stirred at room temperature for 5 hours. The reaction was quenched by addition of NH$_4$Cl solution, and the mixture was extracted with CHCl$_3$. The organic extract was dried and concentrated. The residue was purified by chromatography on silica gel, eluting with 100:1.25:0.025 chloroform: methanol:ammonium hydroxide, to give 40 mg of the title compound. MS (DCI/NH$_3$) m/e: 221 (M+H)$^+$. $^1$H NMR (CDCl$_3$,300 MHz) δ: 8.16 (d, J=2.4 Hz, 1H), 8.08 (d, J=1.2 Hz, 1H), 7.06 (t, J=2.4 Hz, 1H), 4.02 (dd, J=9.3, 5.4 Hz, 1H), 3.92 (dd, J=9.0, 6.0 Hz, 1H), 3.12 (m, 1H), 2.70–2.59 (m, 3H), 2.49 (s, 3H), 2.32 (m, 1H), 2.04 (m, 1H), 1.93–1.68 (m, 3H), 1.25 (t, J=7.80, 3H).

75b. 5-ethyl-3-(2-(S)-pyrrolidinylmethoxy)pyridine dihydrochloride

The compound from step 75b above was treated with HCl in ether according to Example 14c to afford the title compound. MS (DCI/NH$_3$) m/e: 221 (M+H)$^+$. $^1$H NMR (D$_2$O, 300 MHz) d: 8.22 (d, J=6.0, 2H), 7.65 (s, 1H), 4.48 (dd, J=12.0, 3.0, 1H), 4.21 (m, 1H), 3.94 (m, 1H), 3.77 (m, 1H), 3.28 (m, 1H), 3.05 (s, 3H), 2.76 (q, 2H), 2.45 (m, 1H), 2.28–2.03 (m, 3H), 1.24 (t, J=4.5 Hz, 3H).

Anal. Calc. for $C_{13}H_{20}N_2O \cdot 2$ HCl: C, 53.24; H, 7.56; N, 9.55; Found C, 53.53; H, 7.77; N, 9.20.

EXAMPLE 76

Compound of Use 3-(2-(R)-pyrrolidinylmethoxy)quinoline dihydrochloride 76a 3-((1-BOC-2-(R)-pyrrolidinyl)methoxy)quinoline A 2.77 g sample of (R)-1-t-butoxycarbonyl-2-pyrrolidinemethanol and 3 g of 3-hydroxyquinoline were reacted with triphenylphosphine and DEAD in 100 mL of THF according to the procedure of Example 14a, to give 2.5 g of the title compound. MS (DCI/NH$_3$) m/e 329 (M+H)$^+$. $^1$H NMR (CDCl$_3$, 300 MHz) δ: 8.67 (d, J=3 Hz 1H), 8.4 (d, J=7 Hz, 1H), 7.72 (dd, J=7, 1 Hz 1H), 7.56–7.40 (m, 3H), 4.24–3.94 (m, 3 H), 3.42 (bs 2H), 2.11–1.94 (m 3H), 1.92–1.48 (m 1H), (s 9H).

76b. 3-(2-(R)-pyrrolidinylmethoxy)quinoline dihydrochloride

A 2.5 g sample of the compound from step 76a above was dissolved in 8 mL of methylene chloride and cooled in an ice bath. To this solution was added 8 mL of trifluoracetic acid, and the reaction mixture was stirred for 1 hour. Water was added, and the layers were separated. The organic layer was extracted with 2 M HCl. The aqueous layers were combined and extracted with ether. The aqueous solution was then adjusted to pH 10 with K$_2$CO$_3$ and extracted with methylene chloride. The solvent was removed, and the residue was purified by chromatography on silica gel. The compound was treated with HCl in ether according to Example 14c to afford the title compound. MS (DCI/NH$_3$) m/e 229 (M+H)$^+$, 246 (M+NH$_4$)$^+$. $^1$H NMR (D$_2$O, 300 MHz) δ: 8.94(d J=3 Hz, 1H), 8.47 (d J=3 Hz, 1H), 8.14 (dd J=8, 1 Hz 2H), 7.98–7.84 (m, 2H), 4.69 (dd, J=11, 4 Hz 11H), 4.48 (dd, J=11, 7 Hz 1H), 4.23 (m, 1H), 3.46 (t, J=7, 2H), 2.40–2.30 (m, 1H), 2.28–1.97 (m, 3H). Anal. Calc. for $C_{14}H_{16}N_2O \cdot 2$ HCl: C, 55.82; H, 6.02; N, 9.30; Found C, 55.63; H, 6.08; N, 9.07.

EXAMPLE 77

5-n-propyl-3-((1-methyl-2-(S)-pyrrolidinyl)methoxy)pyridine dihydrochloride

To a 1.08 g (4 mmol) sample of 5-bromo-3-((1-methyl-2-(S)-pyrrolidinyl)methoxy)pyridine, prepared as in Example 56a above, dissolved in 30 mL of dry THF and cooled to 0° C. was added 6.0 mL of n-propylmagnesium chloride and 13.0 mg of Ni(dppp)Cl, and the reaction mixture was stirred for 5 hours at room temperature. The reaction was quenched by addition of satd NH$_4$Cl, and the mixture was extracted with chloroform. The solvent was dried over MgSO$_4$ and removed under vacuum, and the residue was purified of a column of silica gel, eluting with 100:1.25:0.025 chloroform:methanol:ammonium hydroxide. The product was converted into the title compound by treatment with HCl in ether according to Example 14c. MS (DCI/NH$_3$) m/e: 235 (M+H)$^+$. $^1$H NMR (D$_2$O, 300 MHz) δ: 8.28 (s, 1H), 8.23 (s, 1H), 7.78 (m, 1H), 4.58 (dd, J=11.4, 3.7 Hz, 1H), 4.42 (dd, J=11.1, 5.9 Hz, 1H), 3.95 (m, 1H), 3.77 (m, 1H), 3.31–3.25 (m, 1H), 3.05 (s, 3H), 2.74 (t, J=7.3 Hz, 2H), 2.48–2.36 (m, 1H), 2.25–2.06 (m, 3H), 1.68 (m, 2H), 0.91 (t, J=7.4 Hz, 3H). Anal. Calc. for $C_{14}H_{22}N_2O \cdot 1.9$ HCl.0.3 ether: C, 56.03; H, 8.22; N, 8.60; Found C, 56.35; H, 8.48; N, 8.73. $[\alpha]^{25}_D$=−3.05° (methanol).

EXAMPLE 78

3-((cis-4-fluoro1-methyl-2-(S)-pyrrolidinyl)methoxy)pyridine dihydrochloride 78a. 3-((cis-4-fluoro-1-methyl-2-(S)-pyrrolidinyl)methoxy)pyridine A 100 mg (0.5 mmol) sample of 3-((trans-1-methyl-4-hydroxy-2(S)-pyrrolidinyl)methoxy)pyridine, from Example 23 above, above was dissolved in 10 mL of methylene chloride and cooled to −78° C. To this was added 0.165 mL (1.25 mmol) of DAST, and the mixture was stirred for 4 hours while allowing the reaction mixture to warm to room temperature. The reaction was quenched by addition of satd NaHCO$_3$ solution, and the mixture was extracted with chloroform. The solvent was removed, and the residue was purified by chromatography on silica gel, eluting with 20:1 CHCl$_3$:methanol, to give 30 mg of title compound.

78b. 3-((cis-4-fluoro-1-methyl-2-(S)-pyrrolidinyl)methoxy)pyridine dihydrochloride The compound from step 78a above was treated with HCl in ether according to Example 14c to afford 20 mg of the title compound. MS (DCI/NH$_3$) m/e: 211 (M+H)$^+$. $^1$H NMR (CD$_3$OD, 300 MHz) δ: 8.77 (d, J=2.6 Hz, 1H), 8.57 (d, J=5.5 Hz, 1H), 8.37 (m, 1H), 8.08 (m, 1H, 5.60–5.40 (m, 1H), 4.72 (m, 1H), 4.58 (m, 1H), 4.21 (m, 1H), 4.04 (m, 1H), 3.65–3.47 (m, 1H), 3.19 (s, 3H), 3.02–2.80 (m, 1H), 2.43–2.28 (m, 1H). Anal. Calc. for $C_{11}H_{15}N_2OF \cdot 2.4$ HCl.0.2 H$_2$O: C, 43.84; H, 5.95; N, 9.29; Found C, 43.47; H, 5.88; N, 8.98.

EXAMPLE 79

3-((1-methyl-2-(S)-pyrroidinyl)methoxy)pyridazine dihydrochloride

A 92.8 mg (0.27 mmol) sample of 3-((1-methyl-2-(S)-pyrrolidinyl)methoxy)-6-chloropyridazine fumarate, from Example 12 above, was dissolved in 10 mL of a 4:1 mixture of ethyl acetate:ethanol, and 0.124 mL (0.89 mmol) of triethylamine and 5 mg of 10% Pd/C were added. The mixture was hydrogenated under 1 atm of H$_2$ for 30 minutes, then the catalyst was removed by filtration. The solvents were removed under vacuum, to the residue was added 20 mL of satd NaHCO3 solution, and the mixture was extracted with methylene chloride. The solution was dried over MgSO4 and taken to dryness, the residue was azeotroped with ethanol several times to remove residual triethylamine. The residue was treated with HCl in ether according to Example 14c to afford 40 mg of the title compound. mp 176–177° C. MS (DCI/NH$_3$) m/e: 194 (M+H)$^+$. $^1$H NMR (D$_2$O, 300 MHz) δ: 8.89 (dd, 1H, J=4.6, 1.3 Hz), 7.75 (dd, 1H, J=9.0, 4.6 Hz), 7.38 (dd, 1H, J=9.0, 1.3 Hz), 4.84 (dd, 1H, J=12.3, 3.1 Hz), 4.67 (dd, 1H, J=12.3, 6.1 Hz), 3.98 (m, 1H), 3.76 (m, 1H), 3.26 (m, 1H), 3.04 (s, 3H), 2.41 (m, 1H), 2.23 (m, 1H). Anal. Calc. for $C_{10}H_{17}Cl_2N_3O \cdot 0.3$ HCl: C, 43.34; H, 6.29; N, 15.11; Found C, 43.23; H, 6.19; N, 14.78.

EXAMPLE 80

5-chloro-3-((1-methyl-2-(S)-azetidinyl)methoxy) pyridine dihydrochloride 80a. 5-chloro-3-((1-methyl-2-(S)-azetidinyl)methoxy) pyridine A 500 mg sample of 5-chloro-3-(N-t-butoxycarbonyl-2-(S)-azetidinylmethoxy)pyridine, prepared as in Example 39a above, was dissolved in 3 mL of 37% HCHO and 1.5 mL of HCOOH, and the reaction mixture was stirred at 100° C. for 40 minutes. The reaction was quenched by addition of $H_2O$. The mixture was adjusted to pH 7 with $NaHCO_3$ and extracted with methylene chloride, the extract was dried over $MgSO_4$, and the solvent was removed to give the title compound (181 mg). MS (DCI/$NH_3$) m/e: 213/215 (M+H)$^+$. $^1$H NMR (CDCl$_3$, 300MHz) δ: 8.22 (d, J=2.5 Hz, 1H), 8.17 (d, J=1.9 Hz, 1H), 7.23 (dd, J=2.5, 1.9 Hz, 1H), 4.01 (d, J=5.1 Hz, 2H), 3.52–3.44 (m, 1H), 3.45–3.35 (m, 1H), 2.94–2.83 (m, 1H), 2.41 (s, 3H), 2.15–2.04 (m, 2H).

80b. 5chloro-3-((1-methyl-2-(S)-azetidinyl)methoxy) pyridine dihdrochloride

The compound of step 80a was treated with HCl in ether according to Example 14c to afford 78 mg of the title compound mp 176–177° C. MS (DCI/$NH_3$) m/e: 213/215 (M+H)$^+$. $^1$H NMR ($D_2O$, 300 MHz) δ: 8.28 (d, J=2.5 Hz, 1H), 8.25 (d, J=1.9 Hz, 1H), 7.63 (dd, J=2.5, 1.9 Hz, 1H), 4.90–4.60 (m, 2H), 4.55–438 (m, 1H), 4.35–4.22 (m, 1H), 4.06–3.95 (m, 1H), 2.99 (s, 3H), 2.75–2.55 (m, 2H). Anal. Calc. for $C_{10}H_{14}Cl_2N_2O\cdot 0.7$ HCl$\cdot 0.5$ $H_2O$: C, 42.34; H, 5.58; N, 9.88; Found C, 42.46; H, 5.62; N, 9.93. $[\alpha]^{25}_D = -20.0°$ (c=0.35, methanol).

EXAMPLE 81

2-methyl-3-(2-(R)-azetidinylmethoxy)pyridine dihydrochloride

Replacing the 1-BOC-2-(S)-azetidinemethanol of Example 29a with 1-BOC-2-R)-azetidinemethanol, from Example 62b, and carrying the reactions forward as in Example 29, except using di-t-butyl dicarbonate in place of DEAD, the free base of the title compound was prepared as a hygroscopic oil. This compound was treated with HCl in ether according to Example 14c to afford the title compound. MS (DCI/$NH_3$) m/e: 179 (M+H)$^+$. $^1$H NMR ($D_2O$, 300 MHz) δ: 8.16 (d, J=5.5 Hz, 1H), 7.79 (d, J=8.5, 1H), 7.62 (dd, J=8.5, 5.5 Hz, 1H), 5.00 (m, 1H), 4.57–4.47 (m, 2H), 4.24 (m, 2H), 4.24–4.12 (m, 2H), 2.78–2.71 (m, 2H). Anal. Calc. for $C_{10}H_{16}Cl_2N_2O\cdot 0.5$ $H_2O$: C, 46.17; H, 6.59; N, 10.77; Found C, 45.93; H, 6.61; N, 10.63. $[\alpha]^{23}_D = -5.85°$ (c=0.21, methanol).

EXAMPLE 82

3-((1-allyl-2-(S)-pyrrolidinyl)methoxy)pyridine dihydrochloride 82a. 3-((1-allyl-2-oxo-5-(S)-pyrrolidinyl)methoxy)pyridine To a solution of 3-((2-oxo-5-(S)-pyrrolidinyl)methoxy) pyridine, from Example 22a (450 mg, 2.34 mmol), in 10 mL of anhydrous THF at 0° C. was added NaH (80% dispersion, 186 mg, 2.68 mmol) was added, and the reaction mixture was stirred for 20 minutes at this temperature. The reaction was then warmed to room temperature, and allyl bromide (425 mg, 3.51 mmol) was added via syringe. After starting material was consumed, water was added to quench the reaction. The desired compound was extracted from the aqueous phase with ethyl acetate and chloroform. The organic layer was dried over $MgSO_4$, then taken to dryness. The residue was purified by silica gel flash chromatography (5% MeOH/CHCl$_3$) to give 450 mg of the title compound. MS (DCI/$NH_3$) m/e: 233 (M+H)$^+$. $^1$H NMR ($D_2O$, 300 MHz) δ: 8.37–8.26 (m, 2H), 7.38–7.29 (m, 2H), 5.83–5.69 (m, 1H), 5.26–5.13 (m, 2H), 4.35–4.24 (m, 1H), 4.16–3.96 (m, 3H), 3.77–3.67 (m, 1H), 2.68–2.54 (m, 1H), 2.50–2.38 (m, 1H), 2.36–2.20 (m, 1H), 2.09–1.96 (m, 1H), 82b. 3-((1-allyl-2-(S)-pyrrolidinyl)methoxy)pyridine dihydrochloride To a solution of 120 mg of the compound from step 82a above in 2 mL of THF was added 0.52 mL of LAH in ether, and the mixture was stirred at room temperature for 3 hours. Quenching with $H_2O$, 40% NaOH and $H_2O$, in that order, was followed by stirring for 1 hour. The mixture was filtered, and the solvent was evaporated. The residue was purified by chromatography on silica gel, eluting with 10.1 chloroform:methanol. The compound of step 81b was treated with HCl in ether according to Example 14c to afford the title compound. $^1$H NMR ($D_2O$, 300 MHz) δ: 8.54 (d, J=2.6 Hz, 1H), 8.45 (d, J=5.5, 1H), 8.17 (m, 1H, 7.97 (dd, J=8.8, 5.6 Hz, 1H, 6.07–5.93 (m, 1H, 5.98–5.93 (m, 2H), 4.64 (dd, J=3.3, 11 Hz, 1H, 4.49 (dd, 1H, J=6.3, 11 Hz), 4.20–4.06 (m, 2H), 3.86 (dd, J=7.4, 13 Hz, 1H, 3.79–3.69 (m, 1H), 3.42–3.25 (m, 1H, 2.50–2.34 (m, 1H, 2.28–2.02 (m, 3H). Anal. Calc. for $C_{13}H_{20}Cl_2N_2O\cdot 0.5$ $H_2O$: C, 52.01; H, 7.05; N, 9.33; Found C, 52.00; H, 7.19; N, 9.49.

EXAMPLE 83

3-((trans-4-hydroxymethyl-1-methyl-2-(S)-pyrrolidinyl)methoxy)pyridine dihydrochloride 83a. 3-((trans-4-hydroxymethyl-1-methyl-2-(S)-pyrrolidinyl)methoxy)pyridine A 1.0 g (4.2 mmol) sample of 3-((-1-methylhydroxymethyl-5-oxo-2-(S)-pyrrolidinyl)methoxy) pyridine, from step 48a above, was dissolved in 15 mL of anhydrous THF, 12.7 mL of $BH_3$ was added, and the mixture was heated at reflux for 2.5 hours. The reaction was quenched with methanol, the solvent was evaporated, and the residue was dissolved in anhydrous ethanol. Cesium fluoride was added, and the resultant solution was stirred under reflux for 16 hr. Evaporation of the solvent and purification of the residue on a silica gel column, eluting with 100:8 to 10.1 chloroform:methanol gave 600 mg of the title compound as a mixture of cis and trans product.

83b. 3-((trans-4-hydroxymethyl-1-methyl-2-(S)-pyrrolidinyl)methoxy)pyridine dihydrochloride The trans-compound from step 83a was treated with HCl in ether according to Example 14c to afford the title compound. mp 151–154° C. MS (DCI/$NH_3$) m/e: 223 (M+H)$^+$. $^1$H NMR ($D_2O$, 300 MHz) δ: 8.49 (d, 1H, J=3 Hz), 8.39 (dd, 1H, J=1, 5 Hz), 8.0 (m, 1H), 7.82 (dd, 1H, J=5, 8 Hz), 4.68–4.60 (m, 1H, 4.54–4.43 (m, 1H), 4.10–3.95 (m, 1H), 3.76–3.60 (m, 2H), 3.50–3.40 (m, 1H), 3.40 (s, 3H), 2.90–2.77 (m, 1H), 2.60–2.46 (m, 1H), 2.35–2.13 (m, 1H), 1.98–1.85 (m, 1H). Anal. Calc. for $C_{12}H_2N_2O_2Cl_2$: C, 48.82; H, 6.82; N, 9.49; Found C, 48.82; H, 6.68; N, 9.26.

EXAMPLE 84

5-(1-methyl-2-(S)-pyrrolidinylmethoxy)pyrimidine dihydrochloride

To a sample of 1-methyl-2-(S)-pyrrolidineimethanol (Aldrich, 16.81 mmol) in 2 mL of DMF was added 0.74 g of NaH (60% dispersion in oil, 18.49 mmol) and 2.68 g (16.81 mmol) of 5-bromopyrimidine. The reaction mixture was stirred at 60° C. for 18 hours, then poured onto ice. The mixture was diluted with brine, and extracted with methylene chloride. The extract was dried over $MgSO_4$, and the solvent was removed. The residue was chromatographed on silica gel, eluting with 20:1 chloroform: methanol. The compound was then taken up in methylene chloride, HCl in ether was added, and the volatiles removed under vacuum. The salt was recrystallized from acetonitrile/ether to afford 822 mg of the title compound. mp>160° C. (dec). MS (DCI/$NH_3$) m/e: 194 (M+H)$^+$. $^1$H NMR ($D_2O$, 300 MHz) δ: 8.88 (s, 1H), 8.65 (s, 2H), 4.64 (dd, J=11.2, 3.1 Hz, 1H), 4.47 (m, 1H), 3.95 (m, 1H), 3.77 (m, 1H), 3.29 (m, 1H), 3.05 (s, 3H), 2.43 (m, 1H), 2.24 (m, 1H), 2.11 (m, 2H). Anal. Calc. for $C_{10}H_{15}N_3OCl_2$: C, 45.13; H, 6.44; N, 15.79; Found C, 45.13; H, 6.74; N, 15.69. $[\alpha]^{25}{}_D$=−2.6° (c=0.57, methanol).

EXAMPLE 85

3-(2-(S)-azetidinylmethoxy)-6-chloropyridazine hydrochloride

A 811 mg sample of 3-(1-BOC-2(S)-azetidinylmethoxy)-6-chloropyridazine, prepared as in Example 13a above, was dissolved in 10 mL of satd HCl in ethanol cooled to 0° C., and the reaction was stirred at room temperature for 16 hours. The solvent was removed under vacuum, and the oily residue was dried under high vacuum for 4 hours to provide a solid. The solid was triturated with ether, collected, and recrystallized three times from ethanol/ether to give 118 mg of the title compound. mp 150–151° C. MS (DCI/$NH_3$) m/e: 200 (M+H)$^+$. $^1$H NMR (DMS-$d_6$, 300 MHz) δ: 9.31 (br s, 1H), 7.87 (d, J=9.2 Hz, 1H, 7.44 (d, J=9.2 Hz, 1H), 4.84–4.63 (m, 3H), 3.98–3.83 (m, 2H), 2.59–2.36 (m, 2H). Anal. Calc. for $C_8H_{11}N_3OCl_2$: C, 40.70; H, 4.70; N, 17.80; Found C, 40.58; H, 4.59; N, 17.58.

EXAMPLE 86

3-((1-methyl-2-(S)-azetidinyl)methoxy)-6-chloropyridine hydrochloride

A 628 mg (2.67 mmol) sample of 5-(2-(S)-azetidinylmethoxy)-2-chloropyridine dihydrochloride, prepared as in Example 52 above, was dissolved in 4 mL of water, and 1 mL of acetic acid, 2 mL of 37% HCHO, and 500 mg of $NaCNBH_4$ were added. The reaction was stirred until the reaction was complete, with addition of acetic acid as necessary to maintain the acidity at approximately pH 5. Then 2 mL of 2 N HCl was added, and the mixture was extracted with ethyl acetate. The aqueous fraction was made basic with $K_2CO_3$ and extracted with chloroform. The extract was dried over $MgSO_4$, concentrated, and the residue was purified by chromatography on silica gel, eluting with 2% to 5% methanol in chloroform to give 210 mg of base. This compound was converted to the salt by treatment with HCl in ethanol, to give 222 mg of the title compound. mp 108–110° C. MS (DCI/$NH_3$) m/e: 213 (M+H)$^+$. $^1$H NMR ($D_2O$, 300 MHz) δ: 8.16 (d, J=3.3 Hz, 1H), 7.56 (dd, J=8.8, 3.3 Hz, 1H), 7.48 (d, J=8.8 Hz, 1H), 4.84–4.73 (m, 1H, 4.52–4.39 (m, 2H), 4.27–4.19 (m, 1H), 4.05–3.96 (m, 1H), 2.97 (s, 3H), 2.73–2.55 (m, 2H). Anal. Calc. for $C_{10}H_{14}N_2OCl_2$).2 HCl: C, 46.84; H, 5.58; N, 10.92; Found C, 47.09; H, 5.66; N, 10.91.

EXAMPLE 87

3-((trans-4-methanesulfonyloxy-1-methyl-2(S)-pyrrolidinyl)methoxy)pyridine dihydrochloride 88a. 3-((trans-1-methyl4-methanesulfonyloxy-5-oxo-2(S)-pyrrolidinyl)methoxy)pyridine A 570 mg (2.6 mmol) sample of 3-((trans-1-methylhydroxy-5-oxo-2(S)-pyrrolidinyl)methoxy)pyridine, prepared as in Example 23a, was dissolved in 17 mL of methylene chloride, and 0.72 ML (5.2 mmol) of triethylamine, a catalytic amount of DMAP and 0.302 mL (3.9 mmol) of methanesulfonyl chloride were added. The reaction mixture was stirred at room temperature for 16 hours then quenched by the addition of $H_2O$. The solvent was stripped from the mixture under vacuum, $NaHCO_3$ was added, and the mixture was extracted with chloroform. The solvent was removed, and the residue was purified by chromatography on silica gel to give 780 mg of title compound.

88b. 3-((trans-1-methyl-4-hydroxy-5-oxo-2(S)-pyrrolidinyl)methoxy pyridine dihydrochloride A sample of the compound from step 88a was reacted with borane in THF according to the method of Example 23b, followed by treatment of the intermediate with cesium fluoride in ethanol for 16 hours at room temperature. Evaporation of the solvent provided a residue which was purified on a silica gel column to give 50 mg of base. This compound was converted to the salt by treatment with HCl in ethanol. mp 65–67° C. MS (DCI/$NH_3$) m/e: 287 (M+H)$^+$. $^1$H NMR ($D_2O$, 300 MHz) δ: 8.44 (d, J=2.6 Hz, 1H), 8.34 (m, 1H), 7.84 (m, 1H), 7.70 (dd, J=8.9, 5.2 Hz, 1H), 5.62 (m, 1H), 4.69 (dd, J=11.8, 2.9 Hz, 1H), 4.52 (m, 1H), 4.41–4.33 (m, 1H), 4.19 (dd, J=14.0, 4.8 Hz, 1H), 3.76 (m, $1H_{1, 3.33}$ (s, 3H), 3.17 (s, 3H), 2.80–2.59 (m, 2H). Anal. Calc. for $C_{12}H_{18}N_2O4$.1.5 HCl: C, 42.26; H, 5.76; N, 8.24; Found C, 42.59; H, 5.60; N, 8.10.

EXAMPLE 88

6-hydroxymethyl-3-((1-methyl-2-(S)-pyrrolidinyl)methoxy)pyridine dihydrochloride 88a. 6-acetloxymethyl-3-((1-BOC-2-(S)-pyrrolidinylmethoxy)pyridine A sample of (S)-1-t-butoxycarbonyl-2-pyrrolidinemethanol (1.64 g, 8.18 mmol, prepared as in Example 15a above) and 1.05 g (6.29 mmol) of 6-acetyloxymethyl-3-hydroxypyridine, prepared as described by Deady and Dayhe, *Aust. J. Chem.*, 2565:36 (1983), were reacted with triphenylphosphine and DEAD (8.18 mmol each) in 25 mL of THF according to the procedure of Example 14a. Workup gave 1.90 g of title compound. MS (DCI/$NH_3$) m/e: 309 (M+H)$^+$. $^1$H NMR ($CDCl_3$, 300 MHz) δ: 8.32–8.28 (m, 1H), 7.33–7.25 (m, 2H), 5.15 (s, 2H), 4.30–3.90 (m, 2H), 3.65–3.25 (m, 3H), 2.13 (s, 3H), 2.10–1.80 (m, 3H), 1.49 (s, 9H).

88b. 6-hydroxymethyl-3-((1-BOC-2-(S)-pyrrolidinyl)methoxy)pyridine

To a solution of 1.0 g of the compound from step 88b in methanol was added a solution of 342 mg of KOH in 1 mL of methanol while cooling in a water bath. The reaction mixture was stirred at room temperature for 30 minutes, then neutralized an concentrated. The residue was purified by chromatography on silica gel, eluting with 1:1 ether hexane and ethyl acetate to give 1.22 g of title compound. MS (DCI/NH$_3$) m/e: 351 (M+H)$^+$. $^1$H NMR (CDCl$_3$, 300 MHz) δ:8.27 (d, J=3.0 Hz, 1H), 7.28 (dd, J=9.3, 3.0 Hz, 1H), 7.16 (d, J=9.3 Hz, 1H), 4.70 (s, 2H), 4.25–3.80 (m, 3H), 3.48–3.30 (m, 3H), 2.10–1.83 (m, 3H), 1.49 (s, 9H).

88c. 6-hdroxymethyl-3-((1-methyl-2-(S)-pyrrolidinyl) methoxy)pyridine

A 669 mg sample of the compound of step 88b above was stirred with 2 mL of 37% HCHO and 1 mL of HCOOH, and the reaction mixture was stirred at 100° C. for 40 minutes. The reaction was quenched by addition of H$_2$O. The mixture was adjusted to pH 7 with NaHCO$_3$ and extracted with methylene chloride, the extract was dried over MgSO$_4$, and the solvent was removed to give the title compound. MS (DCI/NH$_3$) m/e: 223 (M+H)$^+$. $^1$H NMR (CDCl$_3$, 300 MHz) d: 8.28 (d, J=3.0 Hz, 1H), 7.24 (dd, J=9.3, 3.0 Hz, 1H), 7.17 (d, J=9.3 Hz, 1H), 4.71 (s, 2H), 4.05–3.98 (m, 1H), 3.97–3.91 (m, 1H), 3.17–3.08 (m, 1H), 2.73–2.63 (m, 1H), 2.51 (s, 3H), 2.38–2.27 (m, 1H), 2.11–1.68 (m, 4H).

88d. 6-hydroxymethyl-3-((1-methyl-2-(S)-pyrrolidinyl) methoxy)pyridine dihydrochloride A 60 mg sample of the compound of compound from step 88c was treated with HCl in ether according to Example 14c to afford 66 mg of the title compound. MS (DCI/NH$_3$) m/e: 223 (M+H)$^+$. $^1$H NMR (D$_2$O, 300 MHz) δ: 8.38 (d, J=3.0 Hz, 1H), 7.92 (dd, J=9.3, 3.0 Hz, 1H), 7.74 (d, J=9.3 Hz, 1H), 4.85 (s, 2H), 4.63–4.55 (m, 1H), 4.01–3.90 (m, 1H), 3.82–3.73 (m, 1H), 3.32–3.21 (m, 1H), 3.04 (s, 3H), 2.47–2.03 (m, 4H). Anal. Calc. for C$_{12}$H$_{20}$Cl$_2$N$_3$O.0.4 H$_2$O: C, 47.66; H, 6.93; N, 9.26; Found C, 47.58; H, 7.05; N, 9.23. [α]$^{25}_D$4.4° (c=0.50, methanol).

EXAMPLE 89

3-((trans-1,5-dimethyl-2-(S)-pyrrolidinyl)methoxy) pyridine hydrochloride 89a. 3-((1,5-dimethyl-2-(S)-pyrrolidinyl)methoxy)pyridine A 1.24 g (6.0 mmol) sample of 3-(1-methyl-2-oxo-5-(S)-pyrrolidinylmethoxy)-pyridine, prepared as in Example 22b above, was dissolved in 50 mL of ether and cooled to −78° C. To this solution was added 4.71 mL (6.6 mmol) of methyl lithium, and the solution was warmed to room temperature and stirred for 2 hours. The solution was cooled to 0° C., 66 mL of a 1 M solution of LAlH$_4$ was added, and the reaction mixture was stirred for 2 hours at room temperature. The reaction was quenched by addition of 1 mL of methanol, the solvents removed, and the residue purified by chromatography on silica gel, eluting with 200:1 to 100:1 chloroform-:methanol. MS (DCI/NH$_3$) m/e: 207 (M+H)$^+$. $^1$H NMR (CDCl$_3$, 300 MHz) δ: 83.4–8.30 (m, 1H), 8.24–8.17 (m, 1H), 7.25–7.27 (m, 2H), 4.08–4.03 (m, 1H), 3.93–3.87 (m, 1H, 2.83–2.73 (m, 1H), 2.43 (s, 3H), 2.43–2.35 (m, 1H), 2.03–1.82 (m, 2H), 1.70–1.40 (m, 2H), 1.13 (d, J=6.7 Hz, 3H).

89b. 3-((trans-1-dimethyl-2-(S)-pyrrolidinyl)methoxy) pyridine hydrochloride

A 25 mg-sample of the compound of compound from step 89a was treated with HCl in ether according to Example 14c to afford 37 mg of the title compound. MS (DCI/NH$_3$) m/e: 207 (M+H)$^+$. $^1$H NMR (D$_2$O, 300 MHz) δ: 8.42–8.38 (m, 1H), 8.34–8.28 (m, 1H), 7.80–7.76 (m, 1H), 7.67–7.63 (m, 1H), 4.60–4.54 (m, 1H), 4.47–4.41 (m, 1H), 4.03–3.95 (m, 1H), 3.62–3.52 (m, 1H), 3.03 (s, 3H), 2.40–2.30 (m, 2H), 2.13–2.03 (m, 1H), 1.93–1.80 (m, 1H), 1.47 (d, J=6.7 Hz, 3H). [α]$^{25}_D$=+15.4° (c=0.50, methanol). Anal. Caic. for C$_{12}$H$_{18}$N$_2$O.0.40 HCl: C, 49.06; H, 7.00; N, 9.54; Found: C, 49.22; H, 6.47; N, 9.69.

EXAMPLE 90

3-((cis-4-cyano-1-methyl-2(S)-pyrrolidinyl) methoxy)pyridine dihydrochlorde 90a 3-((cis-4-cyano-1-methyl-2(S)-pyrrolidinyl)methoxy)pyridine To a solution of 300 mg (1.05 mmol) of 3-((trans-1-methyl-4-methanesulfonyloxy-5-oxo-2(S)-pyrrolidinyl)-methoxy)pyridine, prepared as in Exanmple 88a above, dissolved in 7 mL of 6:1 DMF:H$_2$O was added 0.51 g (10.5 mmol) of NaCN, and the reaction mixture was heated at 100° C. for 5 hours. The reaction mixture was cooled, diluted with water, and extracted with chloroform. The extract was dried over MgSO4 and concentrated. The residue was purified on a silica gel column, eluting with 100:2 chloroform:methanol, to give 80 mg of the title compound.

90b 3-((cis-4-cyano-1-methyl-2(S)-pyrrolidinyl)methoxy) pyridine dihydrochloride The compound of compound from step 90a was treated with HCl in ether according to Example 14c to afford 75 mg of the title compound. mp 220–222° C. MS (DCI/NH$_3$) m/e: 218 (M+H)$^+$. $^1$H NMR (D$_2$O, 300 MHz) δ: 8.46 (d, J=2.9 Hz, 1H), 8.34 (m, 1H), 7.86 (m, 1H), 7.70 (m, 1H), 4.62 (m, 1H), 4.49 (m, 1H), 4.04 (m, 2H), 3.85 (m, 1H), 3.66 (m, 1H, 3.05 (s, 3H), 2.91 (m, 1H), 2.55 (m, 1H). [α]$^{25}_D$=+15.14° (c=0.50, methanol). Anal. Calc. for C$_{12}$H$_{15}$N$_3$O.2 HCl.0.6 H$_2$O: C, 47.88; H, 6.09; N, 13.96; Found C, 47.70; H, 5.95; N, 14.14.

EXAMPLE 91

3-((cis-5-n-butyl-1-methyl-2-(S)-pyrrolidinyl) methoxy)pyridine dihydrochloride 91a. 3-((cis-5n-butyl-1-methyl-2-(S)-pyrrolidinyl)methoxy) pyridine A 1.24 g (6.0 mmol) sample of 3-(1-methyl-2-oxo-5-(S)-pyrrolidinylmethoxy)-pyridine, prepared as in Example 22b above, was dissolved in mL of THF and cooled to −78° C. To this solution was added 6.0 mL (12 mmol) of 2 M methyl lithium, and the solution was warmed to room temperature, then stirred for 44 hours. Two mL of methanol were added, and the mixture concentrated under vacuum. Another 10 mL of methanol was added, followed by 65.6 mg of NaBCNH$_3$ and a trace of bromocresol green indicator. HCl (4M) was added slowly until the solution remained a yellow color, then the reaction mixture was stirred for 1 hour. The mixture was then adjusted to basic pH with satd NaHCO$_3$, concentrated, and extracted with ethyl acetate. The extract was dried, concentrated and chromatographed on silica gel to give 86 mg of title compound. MS (DCI/NH$_3$) m/e: 248 (M+H)$^+$. $^1$H NMR (CDCl$_3$, 300 MHz) δ: 8.33–8.31 (m, 1H), 8.23–8.19 (m, 1H), 7.23–7.19 (m, 2H), 4.11–4.04 (m, 1H), 3.93–3.86 (m, 1H), 2.87–2.77 (m, 1H, 2.46 (s, 3H), 2.40–2.27 (m, 1H), 2.05–1.20 (m, 10H), 0.92 (t, J=6.0 Hz, 3H).

91b. 3-((cis-5-n-butyl-1-methyl-2-(S)-pyrrolidinyl) methoxy)pyridine

The compound from step 91a was treated with HCl in ether according to Example 14c to afford 106 mg of the title compound. MS (DCI/NH$_3$) m/e: 248 (M+H)$^+$. $^1$H NMR (D$_2$O, 300 MHz) δ: 8.37–8.33 (m, 1H), 8.27–8.24 (m, 1H, 7.67–7.61 (m, 1H, 7.57–7.67 (m, 1H, 4.57–4.52 (m, 1H, 4.44–4.37 (m, 1H), 4.03–3.93 (m, 1H), 3.53–3.42 (m, 1H), 3.05 (s, 3H), 2.50–30 (m, 1H, 2.05–1.20 (m, 10H), 0.91 (t, J=6.0 Hz, 3H). [α]$^{25}_D$=+24.8° (c=0.60, methanol).

EXAMPLE 92

3-((cis-4-fluoromethyl-1-methyl-2-(S)-pyrrolidinyl) methoxy)pyridine dihydrochloride 92a.3-((cis-4-fluoromethyl-1-methyl-2-(S)-pyrrolidinyl) methoxy)pyridine A 1.57 g (7.1 mmol) sample of 3-((4-hydroxymethyl-1-methyl-2-(S)-pyrrolidinyl)methoxy)pyridine, prepared as described in Example 48b above, was dissolved in 40 mL of methylene chloride, and the solution was cooled to −78° C. To this solution was added 2.80 mL (21.2 mmol) of DAST, then the solution was stirred at −35° C. for 1.5 hours. The reaction mixture was warmed to room temperature, and the reaction was quenched by the addition of satd NaHCO$_3$. The mixture was extracted with chloroform, the solvent was removed, and the residue was purified on a silica gel column, eluting with 100:2 chloroform:methanol to 10:1:0.02 chloroform:methanol:ammonia, to give 120 mg of the title compound.

92a 3-((cis-4-fluoromethyl-1-methyl-2-(S)-pyrrolidinyl) methoxy)pyridine dihydrochloride The compound from step 92a was treated with HCl in ether according to Example 14c to afford the title compound. MS (DCI/NH$_3$) m/e: 225 (M+H)$^+$. $^1$H NMR (D$_2$O, 300 MHz) δ: 8.63 (d, J=0.9 Hz, 1H, 8.44 (m, 1H, 7.97 (m, 1H), 4.64–4.43 (m, 5H), 3.49 (m, 1H), 3.31 (m, 1H), 2.92 (s, 3H), 2.90 (m, 1H), 2.41 (m, 1H), 1.63 (m, 1H). 2D NOE data are consitent with the cis configuration. Anal. Calc. for C$_{12}$H$_{17}$N$_2$OF.2 HCl: C, 48.50; H, 6.44; N, 9.43; Found C, 48.22; H, 6.65; N, 9.26. [α]$^{25}_D$+5.83° (methanol).

EXAMPLE 93

3-((1-methyl-2-(S)-pyrrolidinyl)methoxy)-5-nitro-pyridine dihydrochloride 93a. 3,5-dinitropyridine A sample of 2-chloro-3,5-dinitropyridine is dissolved in methanol, hydrazine is added, and the reaction mixture is stirred for 16 hours. The solvent is removed, the residue is dissolved in water, silver acetate is added, and the mixture is heated at reflux for 3 hours. The solution is adjusted to a basic pH, and product is extracted with CHCl$_3$.

93b. 3-((1-methyl-2-(S)-pyrrolidinyl)methoxy)-5-nitro-pyridine dihydrochloride

A sample of 3,5-dinitro pyridine from step 93a above is reacted with (S)-(-)-1-methyl-2-pyrrolidinemethanol according to the procedure of Example 3a, and the product is converted into the title compound by treatment with HCl in ether according to Example 14c.

EXAMPLE 94

5Amino-3-(1-methyl-2(S)-pyrrolidinylmethoxy) pyridine hydrochloride 94a. 5-Amino-3-(1-methyl-2(S)-pyrrolidinylmethyloxy) pyridine To a solution of the compound of example 28a (3 g, 11.1 mmol) in methanol (125 mL) was added CuBr (1.38 g). The resultant mixture was allowed to stir with ammonia at 130° C. for 24 hours. The excess ammonia was evaporated, methanol was removed, and the resultant residue was dissolved in water. The aqueous solution was then extracted with chloroform (3×50 mL). The combined organic layers were dried over anhydrous MgSO$_4$ and filtered. The mixture was concentrated in vacuo and the residue was purified on silica gel to give 2.0 g (86%) of the title compound. MS (DCI/NH$_3$) m/e: 208 (M+H)$^+$. $^1$H NMR (CDCl$_3$,300 MHz) δ: 7.77 (d, 1H, J=3.0 Hz)), 7.72 (d, 1H, J=3.0 Hz), 6.54 (t, 1H, J=3.0 Hz), 4.00–3.85 (m, 2H), 3.62–3.69 (m, 1H), 3.07–3.14(m, 1H), 2.58–2.70 (m, 1H), 2.47 (s, 3H), 2.24–2.35 (m, 1H), 1.95–2.09 (m, 1H), 1.54–1.90 (m, 2H).

94b. 5-Amino-3-(1-methyl-2(S)-pyrrolidinylmethoxy) pyridine hydrochloride

The compound from step 94a was treated with HCl in ether, then again with HCl in dioxane, and the precipitate was collected. The salt was triturated with ether and dried under vacuum to give the title compound. MS (DCI/NH$_3$) m/e: 208 (M+H)$^+$. $^1$H NMR (CDCl$_3$, 300 MHz) δ: 7.77–7.80 (m, 2H), 7.09 (t, 1H, J=2.4 Hz), 4.50 (dd, 1H, J=3.4, 11 Hz), 4.34 (dd, 1H, J=5.8, 11 Hz), 3.87–4.00 (m, 1H), 3.69–3.83 (m, 1H), 3.18–3.34 (m, 1H), 3.03 (s, 3H), 2.31–2.46 (m, 1H, 2.00–2.30 (m, 1H. Anal. calcd for C$_{11}$H$_{17}$N$_3$O.1.6 HCl.1.0 H$_2$O: C, 46.58 H, 7.32 N, 14.82. Found: C, 46.84, H, 7.46 N, 14.42.

EXAMPLE 95

3-((1-methyl-2-(S)-pyrrolidinyl)methoxy)-5-methylamino-pyridine trihydrochloride The 3-((1-methyl-2-(S)-pyrrolidinyl)methoxy)-5-amino-pyridine from is Example 94 is reacted with HCOOH and HCHO according to the method of Example 16a The product is purified by chromatography on silica gel and converted into the title compound by treatment with HCl in ether according to Example 14c.

EXAMPLE 96

3-((1-methyl-2-(S)-pyrrolidinyl)methoxy)-5-methylamino-pyridine trihydrochloride The 3-((1-methyl-2-(S)-pyrrolidinyl)methoxy)-5-amino-pyridine from Example 94 is dissolved in THF and reacted with ethyl iodide according to standard procedures. The product is purified by chromatography on silica gel and converted into the title compound by treatment with HCl in ether according to Example 14c.

EXAMPLE 97

3-((1-methyl-2-(S)-pyrrolidinyl)methoxy)-5-acetlaminypyridine dihydrochloride

The 3-((1-methyl-2-(S)-pyrrolidinyl)methoxy)-5-amino-pyridine from Example 94 is dissolved in THF and reacted with acetyl chloride according to standard procedures. The product is purified by chromatography on silica gel and converted into the title compound by treatment with HCl in ether according to Example 14c.

EXAMPLE 98

3-((1-methyl-2-(S)-pyrrolidinyl)methoxy)-5-methoxy-pyridine dihydrochloride 98a. 3-((1-methyl-2-(S)-pyrrolidinyl)methoxy)-5-bromo-pyridine-N-oxide A sample of 3,5-dibromopyridine-N-oxide (prepared according to the method of Y. Tamura et al., *Heterocycles*, 15:871–874 (1981)) is reacted with (S)-(−)-1-methyl-2-pyrrolidinemethanol according to the procedure of Example 3a, and the product is purified by chromatography on silica gel.

98b. 3-((1-methyl-2-(S)-pyrrolidinyl)methoxy)-5-methoxy) pyridine-N-oxide

A sample of the compound from step 98a above is reacted with sodium methoxide in methanol according to standard procedures. The reaction is quenched with water, the product is extracted, then purified by chromatography on silica gel.

98c. 3-((1-methyl-2-(S)-pyrrolidinyl)methoxy)-methoxy-pyridine dihydrochloride

A sample of the compound from step 98b above is reacted with hydrogen in the presence of Raney nickel according to the method of Y. Tamura et al., *Heterocycles*, 15:871–874 (1981). The product is purified by chromatography on silica gel and converted into the title compound by treatment with HCl in ether according to Example 14c.

EXAMPLE 99

3-((1-methyl-2-(S)-pyrrolidinyl)methoxy)-5-cyano-pyridine dihydrochloride 99a 3-((1-methyl-2-(S)-pyrrolidinyl)methoxy)-5methoxy-pyridine-N-oxide A sample of 3-((1-methyl-2-(S)-pyrrolidinyl)methoxy)-5bromo-pyridine-N-oxide, from Example 98a above, is reacted with sodium cyanide in DMF and water according to standard procedures. The solvents are removed, and the product is extracted, then purified by chromatography on silica gel.

99b. 3-((1-methyl-2-(S)-pyrrolidinyl)methoxy)-5-methoxy-pyridine dihydrochloride A sample of the compound from step 99a above is reacted with hydrogen in the presence of Raney nickel according to the method of Y. Tamura et al., *Heterocycles*, 15:871–874 (1981). The product is purified by chromatography on silica gel and converted into the title compound by treatment with HCl in ether according to Example 14c.

EXAMPLE 100

3-((1-methyl-2-(S)-pyrrolidinyl)methoxy)pyridine-5-carboxylic acid, ethyl ester, dihydrochloride 100a. 3-((1-methyl-2-(S)-pyrrolidinyl)methoxy)-5-bromo-pyridine A sample of 3-((1-methyl-2-(S)-pyrrolidinyl)methoxy)-5-bromo-pyridine-N-oxide, from Example 98a above, is reacted with hydrogen in the presence of Raney nickel according to the method of Y. Tamura et al., *Heterocycles*, 15:871–874 (1981). The solvents are removed, and the product is extracted, then purified by chromatography on silica gel.

100b. 3-((1-methyl-2-(S)-pyrrolidinyl)methoxy)pyridine-5-carboxylic acid, ethyl ester, dihydrochloride A sample of the compound from step 100a above is reacted with palladium triphenylphosphine dichloride and CO in the presence of ethanol and tripropylamide (according to the method of R.A. Head et al., *Tetr. Lett.*, 25:5939–5942 (1984)). The product is purified by chromatography on silica gel and converted into the title compound by treatment with HCl in ether according to Example 14c.

EXAMPLE 101

3-((1-methyl-2-(S)-pyrrolidinyl)methoxy)pyridine-5-carboxylic acid dihydrochloride A sample of the compound from Example 100 above is hydrolyzed with 1N NaOH according to standard methods. The product is purified by chromatography on silica gel and converted into the title compound by treatment with HCl in ether according to Example 14c.

EXAMPLE 102

3-(2-(2-(S)-pyrrolidinyl)ethoxy)pyridine dihydrochloride 102a. 1-BOC-2-(S)-pyrrolidineethanol To a solution of 1-BOC-2-(S)-pyrrolidineethanal (6.80 g, 26.5 mmol) in anhydrous toluene (100 mL), cooled to −78° C. was added a 1M solution of diisobutylaluminum hydride in toluene (132.5 mL, 132.5 mmol). The reaction was stirred at −78° C. for 2 hours, and diisobutylaluminum hydride solution (26.50 mL, 26.5 mmol) was added. The mixture was stirred for 2 hours, then the reaction was quenched at −78° C. with methanol (150 mL). The mixture was poured into 1M Rochelle salt (500 mL), and the emulsified solution was extracted with ethyl acetate (200 mL). The organic layer was washed with brine, dried over $MgSO_4$, and concentrated. The residue was purified on silica gel, eluting with methanol/methylene chloride (5:95) to yield a colorless oil (3.82 g, 67%). MS (DCI/NH3) m/e: 216 $(M+H)^+$. $^1$HNMR (CDCl3, 300 MHz) δ: 1.47 (q, 9H), 1.58–1.76 (m, 2H), 1.82–2.05 (m, 3H), 3.31 (t, J=6.0 Hz, 2H), 3.50–3.69 (m, 2H), 4.10–4.21 (m, 1H), 4.43 (dd, J=4.0, 7.0 Hz, 1H).

102b. 3-(2-(1-BOC-2-(S)-pyrrolidinyl)ethoxy)pyridine

To a solution of triphenylphosphine (3.39 g, 12.9 mmol) in THF (10 mL) was added DEAD (2.03 mL, 15.5 mmol), and the mixture was stirred at room temperature for 20 minutes. Then 3-hydroxypyridine (1.23 g, 15.5 mmol) in 10 mL of THF was added, and the reaction was stirred at room temperature for 10 minutes. The alcohol from step 102a above (2.31 g, 10.80 mmol) in 10 mL of THF was then added, and the mixture was stirred for 16 hours and concentrated in vacuo. The residue was triturated with hexane, then the filtrate was concentrated and purified on silica gel, eluting with ethyl acetate/hexane (1:1) to afford an oil (2.58 g, 84%). MS(DCI/$NH_3$) m/e: 293 $(M+H)^+$. 1H NMR ($CDCl_3$, 300 MHz) δ: 1.49 (s, 9H), 1.74–2.06 (m, 5H), 2.13–2.31 (m, 1H), 3.37–3.40 (m ,2H), 3.95–4.12 (m, 3H), 7.18–7.21 (m, 1H), 8.21 (d, J=8.0 Hz, 1H), 8.29–8.31 (m, 1H).

102c. 3-(2-(2-(S)-pyrrolidinyl)ethoxy)pyridine dihydrochloride

To a solution of the compound from step 102b above (60 mg, 0.20 mmol) in 3 mL of ethanol at 0° C. was added saturated HCl in ethanol (10 mL), and the reaction mixture was stirred for 30 minutes at 0° C. The volatiles were removed under vacuum, and the residue was purified on a column of silica gel, eluting with methanol/methylene chloride (5:95). The product was treated with a saturated solution of HCl/EtOH and held under vacuum for 24 hours to afford a white solid. MS (DCI/$NH_3$) m/e: 193 $(M+H)^+$, 210 $(M+NH_4)^+$. $^1$H NMR ($D_2O$, 300 MHz) δ: 1.69–1.86 (m, 1H), 1.91–2.20 (m, 3H), 2.26–2.43 (m, 2H), 3.28–3.47 (m, 2H), 3.70–3.85 (m, 1H), 4.27–4.45 (m, 2H), 7.82 (dd, J=8.5, 5.0 Hz, 1H), 7.98 (dd, J=9.0, 4.0 Hz, 1H), 8.35 (d, J=6.0 Hz, 1H), 8.45 (d, J=2.0 Hz, 1H). Anal. Calc. for $C_{11}H_{16}N_2O.2.3$ HCl: C, 47.84; H, 6.68; N, 10.14; Found C, 47.48; H, 6.92; N, 9.94. $[\alpha]^{25}_D$=+41.62° (c=0.41, methanol).

EXAMPLE 103

3-(2-(1-methyl-2-(S)-pyrrolidinyl)ethoxy)pyridine dihydrochloride

A 400 mg sample of 3-(2-(2-(S)-pyrrolidinyl)ethoxy) pyridine dihydrochloride, from Example 102 above, was dissolved in 14 mL of 37% HCHO, 14 mL of HCOOH was added, and the reaction mixture was stirred at reflux for 2.5 hours. The solution was washed with ether, adjusted to basic pH with $K_2CO_3$ and extracted with methylene chloride. The extract was dried over $MgSO_4$ and concentrated. The residue was purified on a column of-silica gel, eluting with 10% methanol in methylene chloride. The compound was converted to the salt by the HCl in ether according to Example 14c to afford the title compound. MS ($DCI/NH_3$) m/e: 207 (M+H)$^+$. $^1$H NMR ($D_2O$, 300 MHz) δ: 1.71–1.98 (m, 1H, 2.00–2.23 (m, 3H), 2.37–2.45 (m, 1H, 2.50–2.63 (m, 1H), 2.98 (s, 3H), 3.13–3.25 (m, 1H, 3.53–3.67 (m, 1H), 3.68–3.78 (m, 1H), 4.31–4.48 (m, 2H), 8.00 (dd, J=11.0, 7.0 Hz, 1H), 8.20 (dd, J=10.5, 5.0 Hz, 1H), 8.42 (d, J=6.5 Hz, 1H), 8.50 (d, J=5.0 Hz, 1H). Anal. Calc. for $C_{12}H_{18}N_2OF.1.9$ HCl.1.1 $H_{20}$. C, 48.49; H, 7.46; N, 9.42; Found C, 48.51; H, 7.69; N, 9.61. $[\alpha]^{25}_D$+36.28° (c=0.5, $H_2O$).

EXAMPLE 104

3-(2-(2-(S)-pyrrolidinyl)ethoxy)-6-chloropyridine dihydrochloride 104a. 3-(2-(1-BOC-2-(S)-pyrrolidinyl)ethoxy)-6-chloropyridine To a solution of triphenylphosphine (5.90 mmol, 1.54 g) in THF (17 mL) was added DEAD (5.90 mmol, 1.03 g) and the mixture was stirred at room temperature for 10 minutes. To the mixture was added a solution of 2chloro-5-hydroxypyridine (5.90 mmmol, 0.7611 g) in THF (5.0 mL) and stirring was continued for 10 minutes. The alcohol (1.06 g, 4.90 mmol) from Example 102a in THF (10 mL) was added and the mixture was stirred at room temperature for 16 hours. The mixture was concentrated in vacuo, triturated with hexane, filtered and the volatiles removed. The residue was purified on silica gel, eluting with ethyl acetate/hexane (1:1) which afforded 1.57 g (98%) of a yellow oil. MS(DCI/$NH_3$) 327 (M+H)$^+$, 344 (M+$NH_4$)$^+$. 1H NMR(CDCL3, 300MHz) δ: 1.18–1.80 (m, 2H), 1.45 (s, 9H), 1.71–2.03 (m, 5H), 2.13–2.28 (bs, 1H), 3.28–3.46 (m, 1H), 3.96–4.10 (m, 2H), 7.14–7.25 (m, 2H), 8.01–8.07 (m, 1H).

104b. 3-(2-(2-(S)-pyrrolidinyl)ethoxy)-6-chloropyridine dihydrochloride

To a solution of 124 mg (0.40 mmol) of the compound from step 104a above in 3 mL of ethanol was added 10 mL of satd HCl in ethanol, and the reaction mixture was stirred for 1 hour at room temperature. The volatiles were removed under vacuum, and the residue was acidified and extracted with methylene chloride. The aqueous solution was made basic and extracted with methylene chloride. The extract was dried over MgSO4 and concentrated. The residue was purified on a column of silica gel, eluting with 10970 methanol in methylene chloride. The compound was converted to the salt by the HCl in ether according to Example 14c to afford the title compound. MS ($DCI/NH_3$) m/e: 227 (M+H)$^+$. $^1$H NMR ($D_2O$, 300MHz) δ: 1.69–1.85 (m, 1H), 1.91–2.18 (m, 2H), 2.21–2.37 (m, 3H), 3.23–3.43 (m, 2H), 3.67–3.81 (m, 1H), 4.15–4.46 (m, 2H), 7.47 (m, 2H), 8.06 (d, J=3.5 Hz, 1H). Anal. Calc. for $C_{11}H_{15}N_2OCl.2$ HCl: C, 45.09; H, 5.71; N, 9.34; Found C, 45.04; H, 6.01; N, 9.05. $[\alpha]^{25}_D$=+19.00° (c=0.15, $H_2O$).

EXAMPLE 105

3-(2-(1-methyl-2-(S)-pyrrolidinyl)ethoxy-6-chloropyridine dihydrochloride

A 565 mg sample of 3-(2-(2-(S)-pyrrolidinyl)ethoxy)-6-chloropyridine dihydrochloride, from Example 104 above, was dissolved in 27 mL of 37% HCHO, 27 mL of HCOOH was added, and the reaction mixture was stirred at reflux for 30 minutes. The solution was washed with ether, adjusted to basic pH with $K_2CO_3$ and extracted with methylene chloride and chloroform. The extract was dried over $MgSO_4$ and concentrated. The residue was purified on a column of silica gel, eluting with 10% methanol in methylene chloride. The compound was converted to the salt by the HCl in ether according to Example 14c to afford the title compound. MS ($DCI/NH_3$) m/e: 241 (M+H)$^+$. $^1$H NMR ($D_2O$, 300 MHz) δ: 1.82–1.97 (m, 1H), 2.01–2.20 (m, 3H), 2.38–2.54 (m, 2H), 2.98 (s, 3H), 3.05–3.25 (m, 1H), 3.50–3.63 (, 1H), 3.65–3.77 (m, 1H), 4.13–4.32 (m, 2H), 7.40 (d, J=10 Hz, 1H), 7.48 (dd, J=10.5, 4.0 Hz, 1H, 8.10 (d, J=3.0 Hz, 1H). Anal. Calc. for $C_{12}H_{17}N_2OCl.1.9$ HCl: C, 46.49; H, 6.14; N, 9.03; Found C, 46.70; H, 6.06; N, 9.04. $[\alpha]^{25}_D$=+21.00° (c=0.20, $H_2O$).

EXAMPLE 106

3-(2-(S)-pyrrolidinylmethylthioxy)pyridine dihydrochloride 106a. 3-(1-BOC-2-(S)-pyrrolidinylmethylthioxy)pyridine To a solution of triphenylphosphine (1.8 mmol, 0.472 g) in THF (8 mL) was added DEAD (1.8 mmol, 0.283 mL) and the mixture was stirred at )° C. for 20 minutes. To this mixture was added 166.5 mg (1.5 mmol) sample of 3-thiopyridine (prepared from 3-pyridinesulfonic acid according to the procedure of A. Albert and G. B. Barlin, *J. Chem. Soc.*, 1959, 2384) and 361.8 mg (1.8 mmol) of (S)-1-BOC-2-pyrrolidinemethanol (from Example 15a above). The reaction mixture was warmed to room temperature and stirred for 16 hours. The mixture was concentrated in vacuo. The residue was purified on silica gel to five 440 mg of the title compound. MS ($DCI/NH_3$) m/e: 295 (M+H)$^+$. $^1$H NMR ($CDCl_3$, 300 MHz) δ: 8.65–8.58 (m, 1H), 8.46–8.36 (m, 1H), 7.88–7.69 (m, 1H), 4.06–3.88 (m, 1H), 3.65–32.8 (m, 4H), 2.18–1.74 (m, 4H), 1.44 (s, 9H).

106b. 3-(2-(S)-pyrrolidinylmethylthioxy)pyridine dihydrochloride

The compound from step 106a was treated with HCl in ether, then again with HCl in dioxane, and the precipitate was collected. The salt was triturated with ether and dried under vacuum to give the title compound. MS ($DCI/NH_3$) m/e: 195 (M+H)$^+$. $^1$H NMR ($D_2O$, 300 MHz) δ: 8.91–8.84 (m, 1H), 8.64–8.57 (m, 1H), 8.48–8.40 (m, 1H), 7.88–7.82 (m, 1H), 3.86–3.72 (m, 1H), 3.66–3.57 (m, 1H), 3.44–3.28 (m, 3H), 2.36–2.23 (m, 1H), 2.18–1.97 (m, 2H), 1.88–1.76 (m, 1H).

EXAMPLE 107

3-(1-methyl-2-(S)-pyrrolidinylmethylthioxy)pyridine dihydrochloride

A 120 mg sample of 3-(2-(S)-pyrrolidinylmethylthioxy) pyridine dihydrochloride, from Example 106 above, was dissolved in 2 mL of 37% HCHO, 1 mL of HCOOH was added, and the reaction mixture was stirred at reflux for 30 minutes. The solution was washed with ether, adjusted to basic pH with $K_2CO_3$ and extracted with methylene chloride and chloroform. The extract was dried over $MgSO_4$ and concentrated The residue was purified on a column of silica gel, eluting with 10% methanol in methylene chloride. The compound was converted to the salt by the HCl in ether according to Example 14e to afford 84.5 mg of the title compound. MS (DCI/$NH_3$) m/e: 209 (M+H)$^+$. $^1$H NMR ($D_2O$, 300 MHz) δ: 8.69–8.65 (m, 1H), 8.53–8.48 (m, 1H), 8.13–8.09 (m, 1H), 7.60–7.54 (m, 1H), 3.77–3.68 (m, 1H), 3.61–3.48 (m, 2H), 3.42–3.34 (m, 1H), 3.22–3.12 (m, 1H), 2.93 (s, 3H), 2.46–2.33 (m, 1H), 2.18–1.97 (m, 2H), 1.94–1.80 (m, 1H).

EXAMPLE 108

5-Nitro-3-(1-methyl-2(S)-pyrrolidinylmethoxy) pyridine hydrochloride 108a. 3,5-Dinitro-2-pyridinylhydrazine Hydrazine (anhydrous, 0.75 ml, 23.9 mmol) was added to a solution of 2-chloro-3,5-dinitro-pyridine (3.42 g, 16.8 mmol) in methanol (25 mL). The resultant mixture was stirred at room temperature overnight. Solvent was evaporated, and the residue was washed with water and methanol several times to remove the impurities. A dark solid powder was obtained (3.0 g). MS (DCI/$NH_3$) m/e: 200 (M+1). $^1$H NMR (DMSO-$d_6$, 300MHz) d: 9.25 (m, 1H), 9.06 (m, 1H).

108b. 3,5-dinitro-pyridine

Silver acetate (2.0 g) was added to a solution of the crude 3,5-dinitro-pyridinyl-hydrazine (2.2 g) in a mixture of methanol:$H_2O$ (1:1, 6 ml), and the mixture was stirred at reflux overnight. Solvent was evaporated, then water and conc. $NH_4OH$ were added. The mixture was extracted with ethyl ether, the combined extracts were dried over $MgSO_4$, concentrated and purified by column chromatography (5:1 hexane: ethyl acetate) to give the title compound (400 mg) in 21.8% yield. MS (DCI/$NH_3$) m/e: 124 (M–46+1). $^1$H NMR (CDCl$_3$, 300 MHz) δ: 9.77 (m, 2H), 9.27 (m, 1H).

108c. 5-Nitro-3-(1-methyl-2(S)-pyrrolidinylmethoxy)pyridine

1-Methylpyrrolidinylmethanol (0.46 ml, 3.9 mmol) was added to a suspension of NaH in DMF at room temperature. After stirring at room temperature for 30 minutes, 3,5-dinitro-pyridine (0.34 g, 4 mmol) was added, and the mixture was allowed to stir at room temperature for 16 hours. The mixture was diluted with 1:1 water/brine, and the aqueous solution was extrated with ether. The combined ether layers were dried over $MgSO_4$, filtered and concentrated. The residue was chromatographed, eluting with $CH_2Cl_2$:methanol (10:0.5) to afford 70 mg of the title compound. MS (DCI/$NH_3$) m/e: 238 (M+1). $^1$H NMR (CDCl$_3$, 300MHz) δ: 9.06 (m, 1H), 8.62 (d, 1H), 7.97 (m, 1H), 4.07 (m, 2H), 3.50 (s, 3H), 3.13 (m, 1H), 2.73 (m, 1H), 2.35 (m, 1H), 2.05 (m, 1H), 1.82 (m, 3H).

108d. 5-Nitro-3-(1-methyl-2(S)-pyrrolidinylmethoxy)pyridine hydrochloride

The compound from step 108c was treated with HCl in ether (and a few drops of methanol). The precipitate was collected. The salt was triturated with ether and dried under vacuum to give the title compound. MS (DCI/$NH_3$) m/e: 238 (M+1). $^1$H NMR (CD$_3$OH, 300 MHz) δ: 9.09 (s, 1H), 8.76 (m, 1H), 8.29 (m, 1H), 4.64 (dd, J=3.4, 11.2 Hz, 1H), 4.50 (dd, J=6.5, 11.2 Hz, 1H), 3.97 (m, 1H, 3.78 (m, 1H), 3.26 (m, 1H), 3.10 (s, 3H), 2.44 (m, 1H), 2.29–2.06 (m, 3H). Anal. Calc. for $C_{11}H_{15}N_3O_3$.1.2 HCl.0.5 Methanol: C, 46.50; H, 6.18; N, 14.15. found: C, 46.52; H, 6.01; N, 13.93.

EXAMPLE 109

5,6-Dichloro-3-(2-(S)-azetidinylmethoxy)pyridine hydrochloride 109a. 5.6-Dichloro-3-hydroxypyridine The title compound was prepared following the procedures described by Koch and Schnatterer, *Synthesis*, 499, 1990, and Doyle and Bryker, *J. Org. Chem.*, 44,1572, 1979.

109b. 5,6-Dichloro-3-(1-t-butyloxycarbonyl-2-(S)-azetidinylmethoxy)pyridine

N-Boc-2-(S)-azetidinol from Example 7b (1.55 g, 8.28 mmol), triphenylphosphine (2.6 g, 9.94 mmol), DEAD (1.6 mL, 9.94 mmol), and 5,6-dichloro-3-hydroxypyridine (1.5 g, 9.10 mmol) were allowed to react as in Example 9. The crude product was chromatographed eluting with EtOAc:hexane (1:5) to give 1.08 g of a waxy solid, 39% yield. MS (CI) m/e 333 (M+H)$^+$. $^1$H NMR (CDCl$_3$, 300 MHz) δ: 7.97 (d, J=2.8 Hz, 1H), 7.41 (d, J=2.8 Hz, 1H), 4.56–4.48 (m, 1H), 4.40–4.30 (m, 1H), 4.12 (dd, J=10.1, 2.7 Hz, 1H), 3.95–3.82 (m, 2H), 2.42–2.2 (m, 2H), 1.42 (s, 9H).

109c. 5,6-Dichloro-3-(2-(S)-azetidinylmethoxy)pyridine

The compound of step 109b was dissolved in $CH_2Cl_2$ (10 mL) and TFA (10 mL) was added at 0° C. After 30 minutes of stirring the reaction was warmed to room temperature and stirred for an additional 45 minutes. Solvent was removed, and the residue was partitioned between sat'd $K_2CO_3$ solution and $CH_2Cl_2$. The aqueous layer was further extracted with $CH_2Cl_2$ (4×), and the combined organic extracts were dried over $MgSO_4$ and concentrated. The crude material was chromatographed eltuing with 10% methanol/CHCl$_3$ followed by 10% methanol/CHCl$_3$/0.5% $NH_4OH$ to give 475 mgs of a pale solid, 64% yield. m.p.=59–60° C. MS (CI) m/e 233 (M+H)$^+$. $^1$H NMR (CDCl$_3$, 300 MHz) δ: 8.01 (d, J=2.8 Hz, 1H), 7.37 (d, J=2.8 Hz, 1H), 4.33–4.24 (m, 1H), 4.08–3.98 (m, 2H), 3.73 (dd, J=15.8, 8.4 Hz, 1H), 3.49–3.41 (m, 1H), 2.44–2.21 (m, 2H).

109d. 5.6-Dichloro-3-(2-(S)-azetidinylmethoxy)pyridine hydrochloride

The compound from step 109c (338 mg, 1.45 mmol) was slurried in ether (15 mL), and ether saturated with HCl gas was added. Solvent was removed and the remaining white solid was recrystallized from methanol/$Et_2O$ to give 317 mg of short white needles, 81% yield. m.p.=181–182° C. MS (CI) m/e 233 (M+H)$^+$. $^1$H NMR ($D_2O$, 300 MHz) δ: 8.13 (d, J=2.9 Hz, 1H), 7.79 (d, J=2.9 Hz, 1H), 4.99–4.91 (m, 1H), 4.44 (d, J=4.4 Hz, 2H), 4.21–4.03 (m, 2H), 2.74–2.65 (m, 2H). Anal. calc. for $C_9H_{11}Cl_3N_2O$: C, 40.10; H, 4.11; N, 10.39; Found: C, 39.89; H, 4.08; N, 10.25.

EXAMPLE 110

5,6-Dichloro-3-(1-methyl-2-(S)-azetidinylmethoxy) pyridine hydrochloride 110a 5,6-Dichloro-3-(1-methyl-2-(S)-azetidinylmethyloxy) pyridine The compound of Example 109c (126 mg, 0.54 mmol) was slurried in water (4 mL) and acetic acid added (~3 mL) until the solution became homogeneous. An excess of formalin was added, followed by careful addition of sodium cyanoborohydride until the starting material was consumed. A small amount of 12 M HCl was added and the solution was washed with ether. The aqueous phase was then basified with solid $K_2CO_3$ and 15% NaOH soln and then extracted with $CH_2Cl_2$ (×3). The organic layers were combined, dried over $MgSO_4$, concentrated, and purified by flash chromatography using 5% methanol/$CHCl_3$ as the eluant to give 105 mg of a clear oil, 79% yield. MS (CI) m/e 247 (M +H)$^+$. $^1$H NMR (CDCl$_3$, 300 MHz) δ: 8.01 (d, J=2.7 Hz, 1H), 7.36 (d, J=2.7 Hz, 1H), 4.00 (d, J=4.8 Hz, 2H), 3.49–3.33 (m, 2H), 2.92–2.83 (m, 1H), 2.39 (s, 3H), 2.12–2.04 (m, 2H).

110b. 5,6-Dichloro-3-(1-methyl-2-(S)-azetidinylmethoxy) pyridine hydrochloride

The compound from step 110a (99.0 mg, 0.40 mmol) was dissolved in ether (5 mL) and ether saturated with HCl gas was added. Solvent was removed and the remaining white solid was recrystallized from methanoliether to give 75 mg of a white powder, 66% yield. m.p. 144–145° C. MS (CI) m/e 247 (M +H)$^+$. $^1$H NMR (D$_2$O, 300 MHz) d: 8.13 (d, J=2.7 Hz, 1H), 7.78 (d, J=2.7 Hz, 1H), 4.88–4.75 (m, 1H partially buried under solvent), 4.53–4.43 (m, 2H), 4.30–4.22 (m, 1H), 4.08–3.97 (m, 1H), 2.99 (s, 3H), 2.75–2.57 (m, 2H). Anal. calc. for $C_{10}H_{13}Cl_3N_2O.0.1$ HCl: C, 42.09; H, 4.66; N, 9.82; Found: C, 41.86; H, 4.57; N, 9.62.

What is claimed is:

1. A compound of the formula:

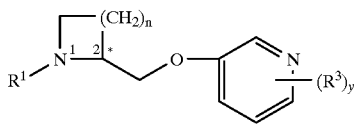

with n=1,2 or 3;

* is a chiral center;

$R^1$ is H or $C_1$–$C_6$ alkyl;

y=1 and $R^3$ is H or is substituted at the 2-, 4-, 5-, or 6-position with $C_1$–$C_3$alkyl or is substituted at the 4-, 5- or 6-position with Br, Cl or F with the proviso that when $R^3$ is at the 2-position and is methyl, $R^1$ must be H; or a pharmaceutically acceptable salt thereof.

2. A compound according to claim 1 wherein $R^1$ is H.

3. A compound according to claim 1 wherein $R^1$ is methyl.

4. A compound according to claim 1 wherein n is 1 selected from the group consisting of:

3-(2-(S)-Azetidinylmethyloxy)pyridine;
5-Chloro-3-(2-(S)-azetidinylmethyloxy)pyridine;
6-Methyl-3-(2-(S)-azetidinylmethyloxy)pyridine;
3-(2-(S)-azetidinylmethoxy)-6-chloropyridine;
3-((1-methyl-2-(S)-azetidinyl)methoxy)-6-methylpyridine;
3-(2-(R)-azetidinylmethoxy)pyridine;
3-((1-methyl-2-(R)-azetidinyl)methoxy)pyridine;
4-Methyl-3-(2-(S)-azetidinylmethyloxy)pyridine;
3-(2-(S)-azetidinylmethoxy)-5-bromopyridine;
3-((1-methyl-2-(S)-azetidinyl)methoxy)-5-bromopyridine;
5-chloro-3-((1-methyl-2-(S)-azetidinyl)methoxy) pyridine;
3-((1-methyl-2-(S)-azetidinyl)methoxy)-6-chloropyridine;
2-Methyl-3-(2-(S)-azetidinylmethyloxy)pyridine;
3-(1-Methyl-2-(S)-azetidinylmethyloxy)pyridine;
3-(2-(R)-azetidinylmethoxy)-6-chloropyridine;
3-(2-(R)-azetidinylmethoxy)-6-fluoropyridine; and
2-Methyl-3-(2-(R)-azetidinylmethyloxy)pyridine.

5. A compound according to claim 1 selected from the group consisting of:

3-((1-methyl-2-(R)-pyrrolidinyl)methoxy)pyridine;
3-(2-(R)-pyrrolidinylmethoxy)pyridine;
3-((1-methyl-2-(S)-pyrrolidinyl)methoxy)pyridine;
3-(2-(S)-azetidinylmethoxy)pyridine;
3-((1-methyl-2-(S)-azetidinyl)methoxy)pyridine;
3-(2-(S)-pyrrolidinylmethoxy)-pyridine;
5-chloro-3-(2-(S)-pyrrolidinylmethoxy)pyridine;
5-chloro-3-((1-methyl-2-(S)-pyrrolidinyl)methoxy) pyridine;
2-methyl-3-(2-(S)-pyrrolidinylmethoxy)pyridine;
6-methyl-3-(2-(S)-pyrrolidinylmethoxy)pyridine;
6-methyl-3-((1-methyl-2-(S)-pyrrolidinyl)methoxy) pyridine;
4-bromo-3-(2-(S)-pyrrolidinylmethoxy)pyridine;
4-bromo-3-((1-methyl-2-(S)-pyrrolidinyl)methoxy) pyridine;
3-((1-methyl-2-piperidinyl)methoxy)pyridine;
4-methyl-3-(2-(S)-pyrrolidinylmethoxy)pyridine;
5-bromo-3-((1-methyl-2-(S)-pyrrolidinyl)methoxy) pyridine;
2-methyl-3-(2-(S)-azetidinylmethoxy)pyridine;
5-chloro-3-(2-(R)-pyrrolidinylmethoxy)pyridine;
5-chloro-3-((1-methyl-2-(R)-pyrrolidinyl)methoxy) pyridine;
2-methyl-3-(2-(R)-pyrrolidinylmethoxy)pyridine;
6-methyl-3-((1-methyl-2-(R)-pyrrolidinyl)methoxy) pyridine;
6-methyl-3-(2-(R)-pyrrolidinylmethoxy)pyridine;
3-((1-ethyl-2(S)-pyrrolidinyl)methoxy)pyridine;
5-chloro-3-(2-(S)-azetidinylmethoxy)pyridine;
6-methyl-3-(2-(S)-azetidinylmethoxy)pyridine;
2-methyl-3-(2-(R)-azetidinylmethoxy)pyridine;
3-((1-methyl-2-(R)-piperidinyl)methoxy)pyridine;
3-(2-(S)-pyrrolidinylmethoxy)-6-chloropyridine;
4-methyl-3-((1-methyl-2-(S)-pyrrolidinyl)methoxy) pyridine;
3-((1-methyl-2-(R)-pyrrolidinyl)methoxy)-6-chloropyridine;
3-(2-(R)-azetidinylmethoxy)-6-chloropyridine;
3-(2-(R)-azetidinylmethoxy)-6-fluoropyridine;
6-chloro-3-((1-methyl-2-(S)-pyrrolidinyl)methoxy) pyridine;

5-bromo-3-((1-methyl-2-(R)-pyrrolidinyl)methoxy) pyridine;

3-(2-(R)-pyrrolidinylmethoxy)-6-chloropyridine;

3-((1-methyl-2-(S)-azetidinyl)methoxy)-6-methylpyridine;

3-(2-(R)-azetidinylmethoxy)pyridine;

3-((1-methyl-2-(R)-azetidinyl)methoxy)pyridine;

4-methyl-3-(2-(S)azetidinylmethoxy)pyridine;

5-bromo-3-(2-(S)-pyrrolidinylmethoxy)pyridine;

3-(2-(S)-azetidinylmethoxy)-5-bromopyridine;

3-((1-methyl-2-(S)-azetidinyl)methoxy)-5-bromopyridine;

5-methyl-3-(1-methyl-2-(S)-pyrrolidinylmethoxy) pyridine;

5-ethyl-3-(1-methyl-2-(S)-pyrrolidinylmethoxy)pyridine;

5-n-propyl-3-(1-methyl-2-(S)-pyrrolidinylmethoxy) pyridine;

5-chloro-3-((1-methyl-2-(S)-azetidinyl)methoxy) pyridine; and 3-((1-methyl-2-(S)-azetidinyl)methoxy)-6-chloropyridine.

6. A pharmaceutical composition comprising a pharmaceutically acceptable amount of a compound according to claim 1 and a pharmaceutically acceptable carrier.

7. A composition according to claim 6 for treating cognitive, neurological, and mental disorders charaterized by decreased cholinergic function comprising a pharmaceutically-acceptable carrier and a therapeutically-effective amount of a compound according to claim 1.

8. A method for selectively activating neuronal nicotinic acetycholine receptors comprising administering a pharmaceutically effective amount of a compound according to claim 1.

* * * * *